US010329329B2

(12) United States Patent
Stone et al.

(10) Patent No.: US 10,329,329 B2
(45) Date of Patent: Jun. 25, 2019

(54) FUSION PROTEINS FOR PROMOTING AN IMMUNE RESPONSE, NUCLEIC ACIDS ENCODING SAME, AND METHODS OF MAKING AND USE THEREOF

(71) Applicant: UNIVERSITY OF MIAMI, Miami, FL (US)

(72) Inventors: Geoffrey W. Stone, Coral Gables, FL (US); Sachin Gupta, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 16/115,171

(22) Filed: Aug. 28, 2018

(65) Prior Publication Data

US 2019/0062380 A1 Feb. 28, 2019

Related U.S. Application Data

(62) Division of application No. 14/424,562, filed as application No. PCT/US2013/058748 on Sep. 9, 2013, now Pat. No. 10,093,701.

(60) Provisional application No. 61/698,109, filed on Sep. 7, 2012.

(51) Int. Cl.

| | |
|---|---|
| ***C07K 14/435*** | (2006.01) |
| ***C07K 14/715*** | (2006.01) |
| ***C12Q 1/68*** | (2018.01) |
| ***A61K 38/00*** | (2006.01) |
| ***C12N 15/81*** | (2006.01) |
| ***C07K 14/005*** | (2006.01) |
| ***C12N 7/00*** | (2006.01) |
| ***C07K 14/47*** | (2006.01) |
| ***A61K 39/245*** | (2006.01) |
| ***C07K 14/72*** | (2006.01) |
| ***C07K 14/705*** | (2006.01) |
| ***C07K 14/735*** | (2006.01) |
| ***C07K 14/725*** | (2006.01) |
| *A61K 39/00* | (2006.01) |

(52) U.S. Cl.

CPC .......... *C07K 14/005* (2013.01); *A61K 39/245* (2013.01); *C07K 14/47* (2013.01); *C07K 14/705* (2013.01); *C07K 14/7051* (2013.01); *C07K 14/7056* (2013.01); *C07K 14/70535* (2013.01); *C07K 14/70546* (2013.01); *C07K 14/70578* (2013.01); *C07K 14/70596* (2013.01); *C07K 14/7156* (2013.01); *C07K 14/7158* (2013.01); *C07K 14/723* (2013.01); *C12N 7/00* (2013.01); *A61K 2039/53* (2013.01); *C07K 2319/00* (2013.01); *C07K 2319/02* (2013.01); *C07K 2319/03* (2013.01); *C12N 2710/16234* (2013.01)

(58) Field of Classification Search

CPC .... A61K 2300/00; A61K 35/15; A61K 38/00; A61K 38/162; A61K 38/191

See application file for complete search history.

(56) References Cited

U.S. PATENT DOCUMENTS

2010/0203067 A1 8/2010 Spencer et al.

FOREIGN PATENT DOCUMENTS

| | | | |
|---|---|---|---|
| CN | 103145849 | A | 6/2013 |
| WO | WO-2010/017248 | A2 | 2/2010 |
| WO | WO-2011/119628 | A2 | 9/2011 |
| WO | WO-2012/040101 | A1 | 3/2012 |

OTHER PUBLICATIONS

EP Search Report dated Jan. 7, 2016, in European Application No. EP13835331.

Gupta et al., "Design of vaccine adjuvants incorporating TNF superfamily ligands and TNF superfamily molecular mimics", Immunology Research (Nov. 7, 2013) 57: 303-310.

Hou et al., MAVS forms functional prion-like aggregates to activate and propagate antiviral innate immune response, Cell, 146:448-61 (2011).

Heldin, "Dimerization of Cell Surface Receptors in Signal Transduction," Cell 80:213-223 (1995).

Hutnick et al., "Selected approaches for increasing HIV DNA vaccine immunogenicity in vivo," Current Opinion in Virology, 1(4):233-240 (2011).

International Search Report and the Written Opinion of the ISA dated Jan. 3, 2014 in International Application No. PCT/US2013/058748. (11 pages).

*Primary Examiner* — Barry A Chestnut

(74) *Attorney, Agent, or Firm* — Marshall, Gerstein & Borun LLP

(57) ABSTRACT

Disclosed herein are compositions, cells, kits, and methods for inducing an immune response in a subject. The compositions can be used as vaccines or vaccine adjuvants against cancer (e.g., melanoma, glioma, prostate, breast) and infectious diseases (e.g., therapeutic and preventative vaccination for viruses), and can be used in cell-based therapies for preventing and treating disorders such as cancer and infection. The compositions, cells, kits and methods involve one or more nucleic acids that encode one or more LMPI fusion proteins (chimeric proteins), and in a typical embodiment, synergistic activation of immune responses by a combination of two or more LMPI fusion proteins.

23 Claims, 23 Drawing Sheets

Specification includes a Sequence Listing.

FUSION PROTEINS FOR PROMOTING AN IMMUNE RESPONSE, NUCLEIC ACIDS ENCODING SAME, AND METHODS OF MAKING AND USE THEREOF

CROSS REFERENCE TO RELATED APPLICATIONS

This application is a Divisional of U.S. application Ser. No. 14/424,562, filed Feb. 27, 2015, which is a U.S. National Stage of International Application No. PCT/US13/58748, filed Sep. 9, 2013, which claims the benefit of U.S. Provisional Application Ser. No. 61/698,109 filed on Sep. 7, 2012, which is hereby incorporated by reference in its entirety, for all purposes, herein.

STATEMENT OF GOVERNMENT INTEREST

This invention was made with government support under Grant Numbers AI 078834 and AI 093294 awarded by the National Institute of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 28, 2018, is named 50545A_Seqlisting.txt and is 72,563 bytes in size.

FIELD OF THE INVENTION

The invention relates generally to the field of immunology. More particularly, the invention relates to fusion proteins, nucleic acids encoding fusion proteins, and methods of use thereof for vaccines and cell therapy.

BACKGROUND

Some current vaccine and cell therapy technologies are associated with the problem of properly activating immune cells for vaccination or immune therapy of patients as a treatment for cancer or infectious disease. There is thus a significant need for improved immune stimulators that provide potent activation of the immune response in patients suffering from cancer or an infectious disease, or who are at risk thereof.

SUMMARY

Disclosed herein are compositions, cells, kits, and methods for inducing an immune response in a subject. The compositions can be used as immune stimulators to increase the response to a vaccine composition (in which case the immune stimulator is described as a vaccine adjuvant) or given to patients to improve ongoing immune responses such as those directed against cancer or an established infection. Representative cancers include melanoma, glioma, prostate, breast, and HPV-related cancers and representative infections include Human Immunodeficiency Virus (HIV), hepatitis C virus, human papilloma virus (HPV), malaria, biodefense related agents, and all other infectious agents that do not currently have effective safe vaccines. These compositions for immune stimulation can also be used in cell-based therapies (e.g. dendritic cell (DC) therapies) where cells are treated ex vivo and then delivered to the subject for preventing and treating disorders such as cancer and infection. The compositions, cells, kits and methods involve one or more nucleic acids that encode one or more LMP1 fusion proteins (also referred to as protein chimeras), and in a typical embodiment provide activation of immune responses by a combination of two or more LMP1 fusion proteins. By combining multiple fusion proteins composed of the LMP1 protein aggregation (transmembrane) domain and the cytoplasmic domain of toll-like receptors (TLR), proteins, Tumor Necrosis Factor Super-Family Receptors (TNFSFR) proteins, pattern recognition receptor (PRR) proteins, or adapter proteins that are involved in innate and/or adaptive immune signaling pathways, introduction of the fusion proteins into immune cells such as dendritic cells or other antigen presenting cells (APCs) results in higher levels of activation. This technology can be used for traditional prophylactic or therapeutic vaccines against cancer and infectious diseases, as well as cell-based therapies such as dendritic cell therapy. In the experiments described herein, combinations of fusion proteins markedly enhanced immune responses and protection from infection, and combinations of one or more TLR agonists and a stimulator of the TNFSFR protein CD40 also induced a synergistic immune activation that protected experimental mice from tumor challenge. Also in the experiments described herein, a surprising result was that LMP1-IPS1 is effective at restricting HIV-1 replication. LMP1-IPS1 inhibits wild-type HIV-1 replication in cell culture and in primary human CD4+ T cells. Bystander cells expressing LMP1-IPS1 can inhibit viral replication, suggesting that LMP1-IPS1 can be given as a therapy in HIV-infected patients. LMP1-IPS1 can be given as a viral vector (i.e. lentiviral vector) targeting sites of HIV-1 infection, thereby reducing HIV-1 replication in tissue reservoirs that are normally resistant to antiretroviral drugs. The compositions, cells, kits and methods described herein address the problem of properly activating and maturing APCs such as dendritic cells for vaccination or immune therapy of patients as a treatment for cancer or infectious disease, and can also be used to develop prophylactic vaccines and other immune therapies dependent on immune activation.

Unless otherwise defined, all technical terms used herein have the same meaning as commonly understood by one of ordinary skill in the art to which this invention belongs.

As used herein, a "nucleic acid" or a "nucleic acid molecule" means a chain of two or more nucleotides such as RNA (ribonucleic acid) or DNA (deoxyribonucleic acid), and chemically-modified nucleotides. The nucleic acid molecule may be purified. A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The terms include, e.g., a recombinant nucleic acid molecule incorporated into a vector, a plasmid, a virus, or a genome of a prokaryote or eukaryote. Examples of purified nucleic acid molecules include cDNAs, fragments of genomic nucleic acid molecules, nucleic acid molecules produced by polymerase chain reaction (PCR), nucleic acid molecules formed by restriction enzyme treatment of genomic nucleic acid molecules, recombinant nucleic acid molecules, and chemically synthesized nucleic acid molecules.

By the term "LMP1 gene," is meant a native Epstein Barr virus LMP1-encoding nucleic acid sequence, e.g., the native Epstein Barr virus LMP1 gene; a nucleic acid having sequences from which a LMP1 cDNA can be transcribed; and/or allelic variants and homologs of the foregoing. An exemplary nucleic acid sequence of LMP1 is GenBank Accession No. M58153.1. The term encompasses double-stranded DNA, single-stranded DNA, and RNA.

By the term "LMP1 protein," is meant an expression product of a LMP1 gene or a protein that shares at least 65% (but preferably 75, 80, 85, 90, 95, 96, 97, 98, or 99%) amino acid sequence identity with the foregoing and displays a functional activity of a native LMP1 protein. A "functional activity" of a protein is any activity associated with the physiological function of the protein. LMP1 consists of an N-terminal transmembrane region linked to a C-terminal cell signaling region that is analogous to the CD40 receptor on immune cells (see FIG. 1A). In addition to anchoring LMP1 into the membrane, the N-terminus of LMP1 self-aggregates and leads to clustering of LMP1 or any protein linked to the LMP1 N-terminal domain. The transmembrane (aggregation) domain of LMP1 protein is amino acids 1-190 of the amino acid sequence set forth in GenBank Accession No. AAA66330.1.

As used herein, "protein" and "polypeptide" are used synonymously to mean any peptide-linked chain of amino acids, regardless of length or post-translational modification, e.g., glycosylation or phosphorylation. The terms "fusion protein," "chimeric protein," and "chimera" are used interchangeably herein, and mean a protein made by translation of an artificial combination of two otherwise separated segments of sequence, e.g., by chemical synthesis or by the manipulation of isolated segments of nucleic acids by genetic engineering techniques.

When referring to a peptide, oligopeptide or protein, the terms "amino acid residue", "amino acid" and "residue" are used interchangably and, as used herein, mean an amino acid or amino acid mimetic joined covalently to at least one other amino acid or amino acid mimetic through an amide bond or amide bond mimetic.

When referring to a nucleic acid molecule, polypeptide, or infectious pathogen, the term "native" refers to a naturally-occurring (e.g., a wild-type (WT)) nucleic acid, polypeptide, or infectious pathogen.

As used herein, the term "antigen" or "immunogen" means a molecule that is specifically recognized and bound by an antibody.

The term "antibody" is meant to include polyclonal antibodies, monoclonal antibodies (mAbs), chimeric antibodies, humanized antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques.

As used herein the term "adjuvant" means any material which enhances the humoral and/or cellular immune response.

As used herein, an "immune cell" refers to dendritic cells, macrophages, lymphocytes, mast cells, endothelial cells, lymphatic vessel cells and the like which can, when properly stimulated, serve as an antigen-presenting cell (APC) to initiate an immune response or as an effector cell of an immune response.

As used herein, the terms "displayed", "presented", or "surface exposed" are considered to be synonyms, and refer to antigens or other molecules that are present (e.g., accessible to immune site recognition) at the external surface of a structure such as a cell.

As used herein, "vaccine" includes all prophylactic and therapeutic vaccines.

By the phrase "immune response" is meant induction of antibody and/or immune cell-mediated responses specific against an antigen or antigens or allergen(s) or drug or biologic. The induction of an immune response depends on many factors, including the immunogenic constitution of the challenged organism, the chemical composition and configuration of the antigen or allergen or drug or biologic, and the manner and period of administration of the antigen or allergen or drug or biologic. An immune response has many facets, some of which are exhibited by the cells of the immune system (e.g., B-lymphocytes, T-lymphocytes, macrophages, and plasma cells). Immune system cells may participate in the immune response through interaction with an antigen or allergen or other cells of the immune system, the release of cytokines and reactivity to those cytokines. Immune responses are generally divided into two main categories—humoral and cell-mediated. The humoral component of the immune response includes production of antibodies specific for an antigen or allergen or drug or biologic. The cell-mediated component includes the generation of delayed-type hypersensitivity and cytotoxic effector cells against the antigen or allergen.

As used herein, the term "treatment" is defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

As used herein, the phrase "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a composition of the present invention effective to yield the desired therapeutic response, for example, an amount effective to activate an immune response in an individual. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed.

The terms "patient" "subject" and "individual" are used interchangeably herein, and mean a mammalian subject (e.g., human, rodent, non-human primates, canine, bovine, ovine, equine, feline, etc.) who is to be treated, who has been treated, or who is being considered for treatment, and/or to obtain a biological sample from, with human patients being preferred. In some cases, the methods, kits, and compositions described herein find use in experimental animals, in veterinary applications for livestock, domesticated animals, and companion animals, and in the development of animal models for disease, including, but not limited to, rodents including mice, rats, and hamsters, as well as non-human primates.

Accordingly, described herein is a composition for inducing an immune response in a subject. The composition includes at least a first nucleic acid encoding at least a first fusion protein, the at least first fusion protein including a transmembrane domain of LMP1 to provide for clustering of the at least first fusion protein in cells without the need for any exogenous molecule and at least one signaling domain from at least one of: an immune activating receptor and/or an adaptor protein, the at least first nucleic acid in an amount sufficient to induce an immune response in a subject. The immune activating receptor can be, for example, a Toll-like receptor (TLR) or a TNF superfamily receptor (TNFSFR). The at least first fusion protein can include a signaling domain from a TLR and a signaling domain from a TNFSFR. In another embodiment, the at least first fusion protein can include a signaling domain from an immune activating receptor and/or a signaling domain from an adaptor protein. The immune activating receptor can be, for example, TNF Receptor SuperFamily (TNFRSF) proteins, preferably CD40, 4-1BB, RANK, TACI, OX40, CD27, GITR, LTβR, and BAFFR; Toll-Like Receptors (TLR) TLR1 to TLR13, preferably TLR7; integrins; FcγRIII; Dectin1; Dectin2; NOD1; NOD2; CD16; IL-2R; Type I/II interferon receptor; chemokine receptors such as CCR5 and CCR7; G-protein coupled receptors (GPCRs); TREM1; the B cell receptor (BCR) complex that includes CD79A, CD79B, and Ig-alpha, etc. The adaptor protein can be, for example, one of: IPS-1; MyD88; RIG-1; MDA5; CD3 zeta chain; MyD88ΔTIR; TRIF; TRAM; TIRAP; MAL; BTK; RTK; RAC1; SYK; NALP3 (NLRP3); NALP3ΔLRR; NALP1; CARD9; DAI; IPAG; STING; Zap70; and LAT. The at least first nucleic acid can further encode an antigen. The at least first nucleic acid can be included within a viral vector. The viral vector (including the nucleic acid sequence) can be within (encapsulated by) a recombinant virion. The composition can further include a second nucleic acid encoding a second fusion protein, the second fusion protein including a transmembrane domain of LMP1 and at least one signaling domain from at least one of: an immune activating receptor and an adaptor protein. The at least first and the second nucleic acid can be included within a viral vector. Typically, the at least first nucleic acid is an amount effective for activating and maturing immune cells (e.g., dendritic cells) when administered to a subject (e.g., a human). In a composition as described herein, the at least first nucleic acid can be in an amount effective for inducing expression of cytokines and protecting primary CD4+ T cells from infection by a virus (e.g., human immunodeficiency virus (HIV)) when administered to a subject (e.g., a human). The at least first fusion protein can include a transmembrane domain of LMP1 and a signaling domain from IPS-1.

Also described herein is a vaccine formulation for preventing or treating a disease or condition in a subject including a composition as described herein and a pharmaceutically acceptable excipient. The disease or condition can be, for example, cancer or infection.

Further described herein is a vaccine adjuvant for enhancing an immune response to a vaccine. Typically the vaccine adjuvant includes a composition as described herein and an antigen or a nucleic acid encoding an antigen in an amount effective for enhancing an immune response to a vaccine and a pharmaceutically acceptable excipient. In one embodiment, the at least first nucleic acid can further encode the antigen.

Still further described herein is an immune cell transduced with a composition as described herein. In a typical embodiment, the immune cell is a dendritic cell. The immune cell can be within a vaccine formulation for preventing or treating a disease or condition (e.g., cancer or infection) in a subject.

Additionally described herein is A method of inducing an immune response against cancer or infection in a subject. The method includes administering a composition as described herein to the subject in a therapeutically effective amount for inducing an immune response against the cancer or infection in the subject. Administering the composition to the subject vaccinates the subject against cancer or infection. Inducing an immune response against the cancer or the infection in the subject can include at least one of: activating and maturing dendritic cells, and inducing expression of at least one cytokine in the subject. The cancer can be, for example, melanoma, glioma, prostate cancer, breast cancer, and the infection is selected from the group consisting of: HIV infection, hepatitis C infection or human papilloma virus infection. In one embodiment, the subject has an HIV infection, and inducing an immune response against the infection includes induction of type I interferon and protection of primary CD4+ T cells in the subject. In another embodiment, the subject has a cancerous tumor, and the at least first fusion protein includes a transmembrane domain of LMP1 and a signaling domain from IPS-1 or a signaling domain from MyD88. In this embodiment, inducing an immune response results in a decrease in growth of the cancerous tumor.

Yet further described herein is a kit for preventing or treating a disease or condition in a subject. A kit includes a composition, vaccine formulation, or vaccine adjuvant as described herein; instructions for use; and packaging.

Also described herein is a composition for inducing an immune response in a subject including a nucleic acid encoding a fusion protein. In the composition, the fusion protein includes a transmembrane domain of LMP1 and an amino acid sequence including two or more signaling motifs from immune activating receptors and/or adaptor proteins. The nucleic acid is in an amount sufficient to induce an immune response in a subject.

Although compositions, cells, kits, and methods similar or equivalent to those described herein can be used in the practice or testing of the present invention, suitable compositions, cells, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Figure 1:
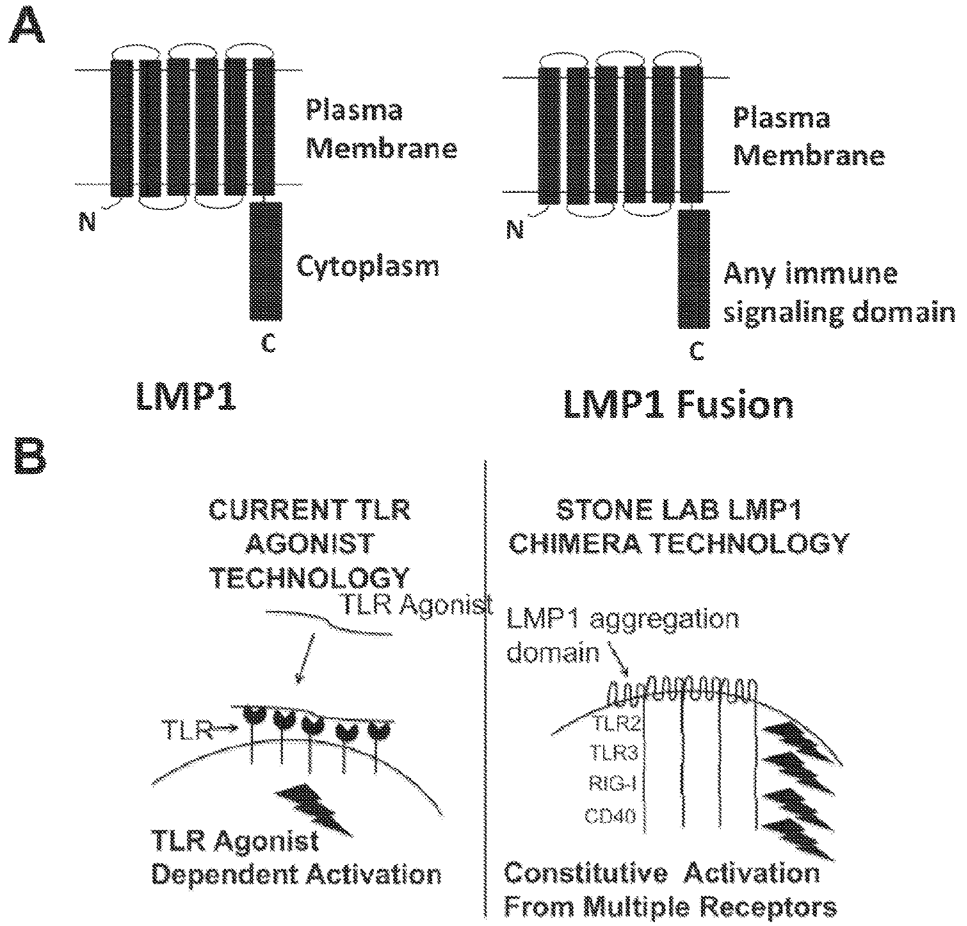
FIG. 1 is a model of LMP1 fusion protein technology as described herein.
Figure 1:
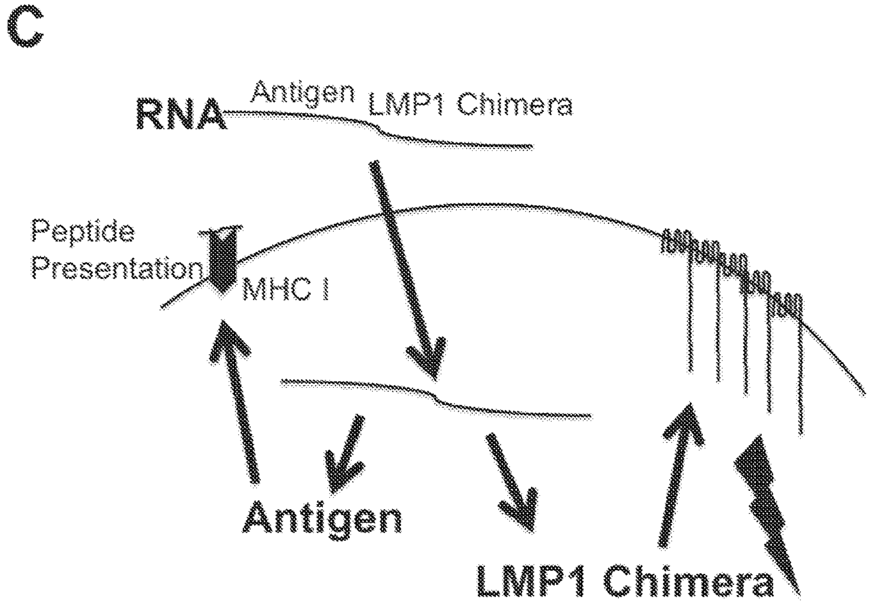

Described herein are LMP1 fusion proteins, nucleic acids encoding the fusion proteins, viral vectors containing the nucleic acids, and cells transduced with the nucleic acids for inducing an immune response in a subject. In our previous publications (S. Gupta et al., Journal of Leukocyte Biology 90:389-398, 2011; and S. Gupta et al., Retrovirology 8:39, 2011) and a prior application (R. S. Kornbluth and G. W. Stone, PCT WO 2011/119628, now US patent application pub. No. 2013/0039942 A1 and EP11760085.8), the invention of LMP1 fusion proteins is described. These were described as fusion proteins that combine an LMP1 transmembrane domain and a single (not more than one) signaling domain taken from protein receptors in the Tumor Necrosis Factor Receptor SuperFamily (TNFRSF). In the instant invention, LMP1 fusions are made with a plurality (two or more) of signaling domains. Additionally, the instant invention presents fusion proteins of LMP1 combined with a signaling domain that is not derived from a TNFRSF but instead is derived from other types of immune activating receptors such as Toll-Like Receptors (TLRs) and/or adaptor proteins that are not part of receptors at the cell surface but rather intracytoplasmic adaptor molecules that initiate signaling events downstream from cell surface receptors in the cell such as IPS-1. Collectively, the LMP1 fusion proteins of the instant invention contain signaling domains selected from the TNFRSFs, TLRs, and/or adaptor molecules such that two or more signaling domains are fused with portions of LMP1. As an exception, LMP1 itself has a C-terminal intracytoplasmic domain that is recognized as functionally similar to a TNFRSF signaling domain, specifically from the CD40 receptor, a member of the TNFRSFs. Consequently, fusion proteins of the instant invention are of the form LMP1 transmembrane domain (LMP1TM) operatively linked to signaling domain X and operatively linked to signaling domain Y to form LMP1TM-X-Y, where the linkage is normally provided by peptide bonds that make the fusion protein a single polypeptide strand. In cases where the entire LMP1 protein is used, the "X" portion is the signaling domain that naturally occurs in LMP1 followed by one or more "Y" signaling domains so that again the fusion proteins contains two or more signaling domains. In yet another embodiment, the instant invention describes LMP1 fusion proteins wherein a peptidic antigen (Ag) is included in the LMP fusion protein polypeptide. Such fusion proteins have the structure of Ag-LMP1TM-X-Y and may have sequences that include an internal ribosome entry site (IRES) between the sequence encoding the antigen and the sequence encoding the N-terminal transmembrane domain of LMP1. The unifying feature of all of these fusion proteins is the presence of the LMP1 N-terminal transmembrane domain which (1) anchors the fusion proteins into membranes and (2) aggregates them into clusters in the cell membrane. By clustering the signaling domains, LMP1 fusion proteins allow those signaling domains to engage downstream adaptor molecules that lead to altered gene expression in the nucleus. Prior to this invention, it was not known in the art that the same LMP1 transmembrane domain could activate more than one signaling domain when the LMP1 and two or more signaling domains are joined in tandem in a single polypeptide chain. As a modification of this concept, an LMP1 fusion protein was made using Interferon Promoter Stimulator-1 (IPS-1, also called MAVS, VISA, or Cardif). In this case, fusion to LMP1 provides for the aggregation of IPS-1 that is needed for cellular activation by the IPS-1 protein (F. Hou et al., Cell 146:448-461, 2011). This novel molecule, LMP1-IPS-1, has only one signaling domain but that signal domain is used in a way not previously known in the art.

Figure 3:
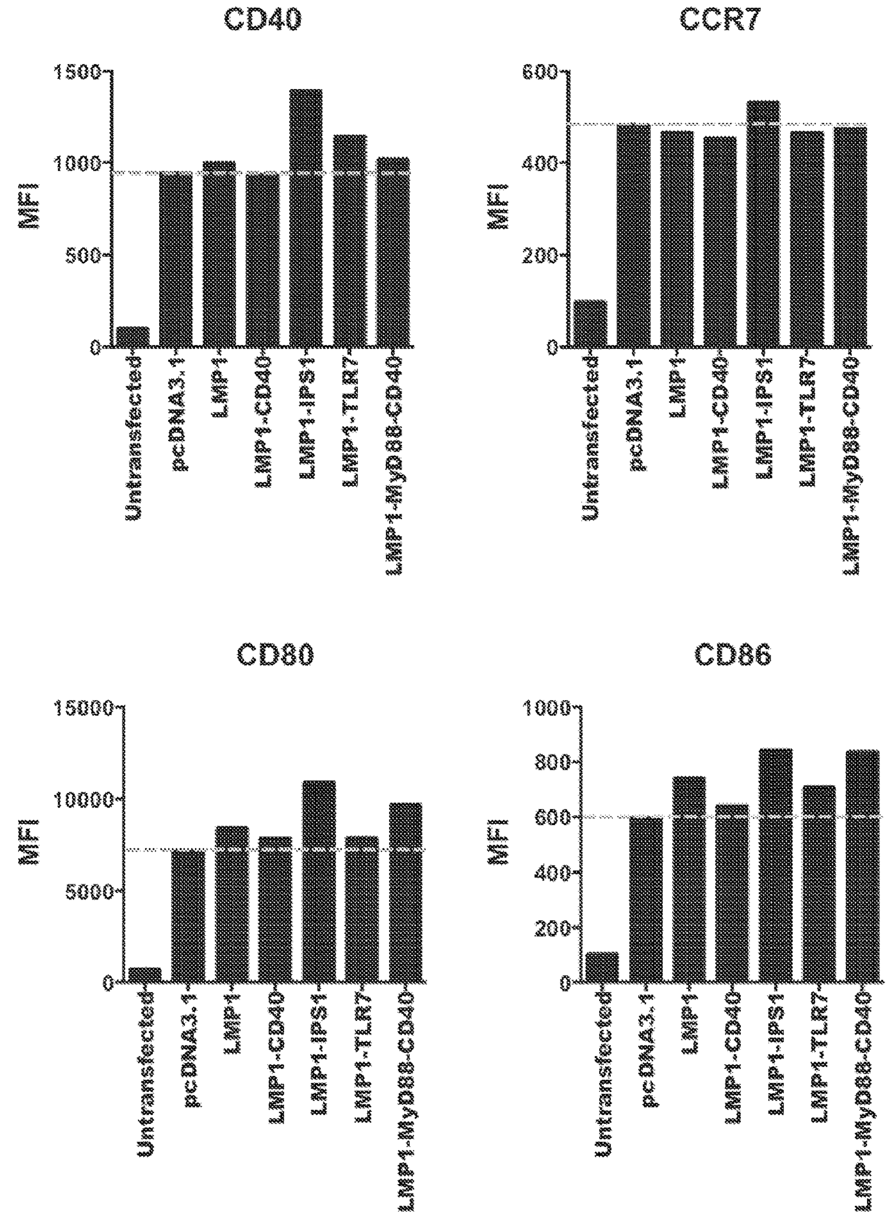
FIG. 3 is a series of graphs of results showing that LMP1 fusion proteins with IPS-1, TLR7, and MyD88-CD40 enhance activation and IL-6 cytokine secretion from a RAW 264.7 mouse macrophage cell line.
Figure 3:
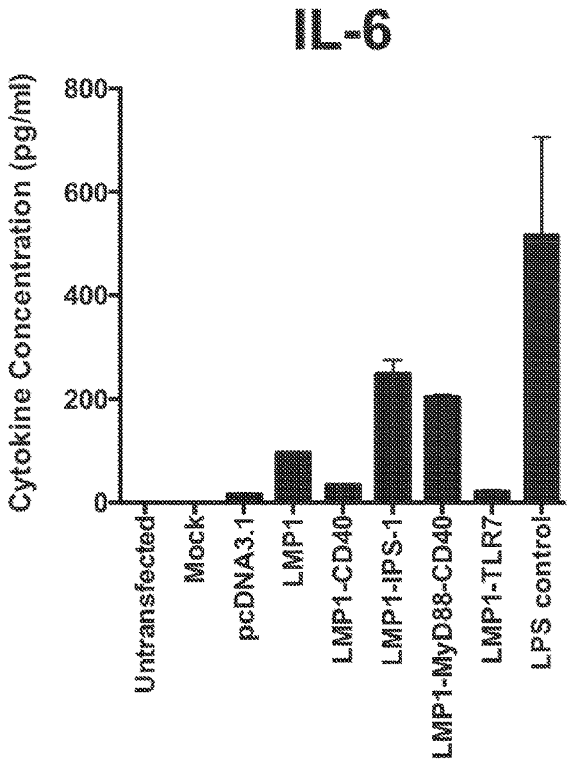
Figure 3:
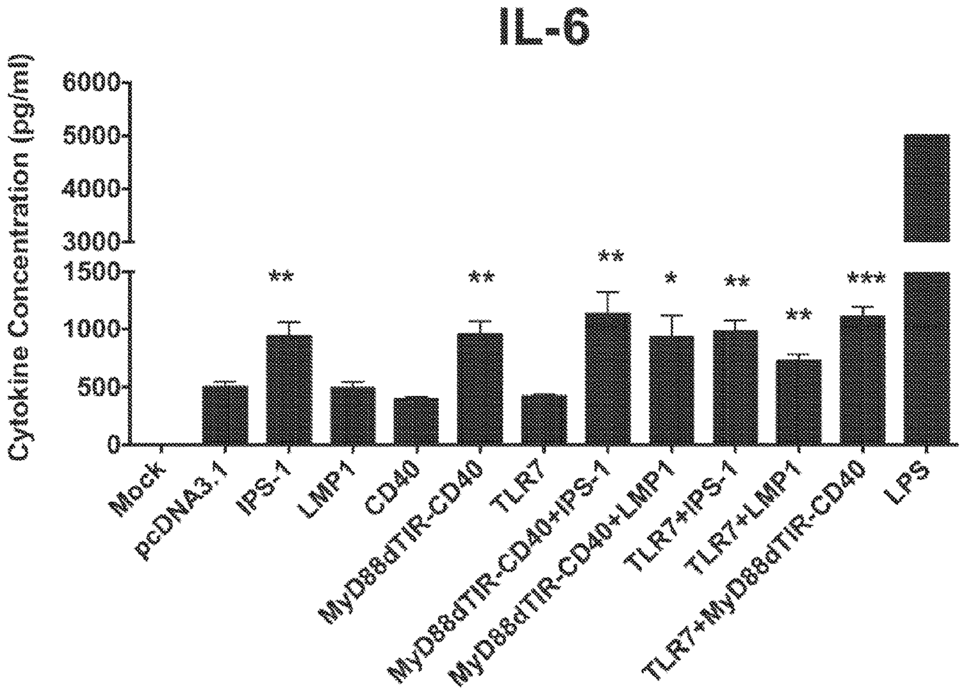

Latent membrane protein-1 (LMP1) is a gene in the Epstein-Barr Virus (EBV). As shown in FIG. 1, its N-terminus is composed of 6 contiguous transmembrane domains that anchor the protein into the membrane. The intracytoplasmic domain of LMP1 is analogous to the signaling domain of the CD40 receptor, a TNFRSF. The activation of CD40 requires that it become clustered in the membrane so that its cytoplasmic signaling domain forms a supramolecular signaling complex in concert with adaptor molecules in the TNF Receptor Activating Factor (TRAF) family, e.g., TRAF2, TRAF3, TRAF6), also referred to as a signalosome. The clustering of CD40 is initiated by either a multimeric form of its ligand (CD40 ligand or CD40L) or by anti-CD40 antibodies that must be arrayed on a nearby cell via binding to Fc receptors (as reviewed in R. S. Kornbluth, M. Stempniak, and G. W. Stone, International Review of Immunology 31:279-288, 2012). However, LMP1 needs no ligand or antibody to initiate signaling through its cytoplasmic domain since its N-terminal transmembrane domain spontaneously forms clusters in the cell membrane and thereby clusters the intracytoplasmic domain(s) that are connected to it via peptide bonds as a single polypeptide chain. In this sense, LMP1 is said to be "constitutively activated." Likewise, fusion proteins that link the N-terminal transmembrane domain to signaling domain(s) that require clustering in order to function can also be said to be "constitutively activated" and no longer need the ligand from the receptor from which they are taken. For example, TLR7 is normally activated by viral RNA as a ligand, but LMP1-TLR7 (a fusion protein formed by linking the LMP1 N-terminal transmembrane domain with the intracellular TLR7 signaling domain) is constitutively active and signals without a ligand (FIG. 3). Because LMP1 fusion proteins are constitutively active, they differ significantly from "inducible"

protein constructs (B. A. Hanks et al., Nature Medicine 11:130-137, 2005; D. Spencer, B. Hanks, and K. Slawin, U.S. Pat. No. 7,404,950 B2; D. Spencer and N. Lepteva, US 2011/0033383 A1; and D. Spencer and N. Priyadharshini, US 2010/0203067 A1). These inducible protein constructs rely upon a chemically inducible dimerization (CID) domain to produce clustering of the construct when a chemically induced dimerization agent is administered to the subject (e.g., AP20187). In marked constrast, the molecules of the instant invention spontaneously cluster in a controlled and reproducible manner by virtue of being linked to the LMP1 N-terminal transmembrane and do not require any exogenous molecule or chemical to function.

In making LMP1 fusion proteins, the signaling domains comprise one or more cytoplasmic signaling domains of immune activating receptors (e.g., TLR cytoplasmic domains and/or TNFSFR cytoplasmic domains) and/or adaptor proteins. The immune activating receptors being contemplated in this invention include, for example, TNFRSFs (e.g., CD40, 4-1BB, RANK, TAC1, OX40, CD27, GITR, LTβR, and BAFFR), TLR1 through TLR13 inclusive, integrins, FcγRIII, Dectin1, Dectin2, NOD1, NOD2, CD16, IL-2R, Type I/II interferon receptor, chemokine receptors such as CCR5 and CCR7, GPCRs, TREM1, and the B cell receptor (BCR) complex that includes CD79A, CD79B, Ig-alpha, and Ig-beta. The adaptor proteins being contemplated in this invention include, for example, IPS-1, RIG-1, MDA5, CD3 zeta chain, MyD88, MyD88ΔTIR, TRIF, TRAM, TIRAP, MAL, BTK, RTK, RAC1, SYK, NALP3 (NLRP3), NALP3ΔLRR, NALP1, CARD9, DAI, IPAG, STING, Zap70, and LAT. These LMP1 fusion proteins can be encoded within recombinant DNA, RNA, or viral vectors for the treatment of subjects. In some formulations, an antigen will be encoded within the same vector as the LMP1-fusion, inducing antigen-specific immune activation. Based on the protein binding motifs within each of these cytoplasmic domains, an artificial cytoplasmic domain can be constructed that incorporates signaling domains from one or more immune activating receptors and/or one or more adapter proteins in combinations that give the greatest immune response. This artificial signaling domain is anticipated to induce greater immune activation, and more effective vaccines or immune therapy, compared to the wild-type signaling domains. An artificial cytoplasmic domain composed of intracellular signaling motifs from multiple TLRs, TNFSFR, or adapter molecules can, as a single gene product, mimic the synergy induced by multiple but separate LMP1 fusion proteins. Such a super-activating LMP1 construct can be used as a vaccine adjuvant and immune stimulator.

Several of the signaling domains contemplated in this invention are part of the inflammasome pathway. These include IPS-1, NALP2, NLRP3, and AIM2. A key function of the inflammasome pathway is to activate the proteases (e.g., caspase-1) that cleave the inactive precursor of interleukin-1-beta (pro-IL-1beta) into the active form of this cytokine (IL-1beta). The precursor protein, pro-IL-1-beta, is not normally present in immune cells but instead the transcription of its gene and the production of the inactive protein is initiated by activating TLRs and downstream adaptor molecules for the TLR pathway. Thus, the induction of the inflammasome and cleavage of pro-IL-1beta to IL-1beta may be accomplished by induction of IL-1beta gene using LMP1-TLR2, LMP1-MyD88, etc, together with caspase inflammasome induction with LMP1 fused to domains of proteins such as NALP2, NLRP3, or AIM2 which are involved in inflammasome induction. The LMP1 fusions described herein would also be effective even in the context where the APC does not express the natural receptor for the TLR agonist or TNFSFR agonist, since the LMP1 fusions already encode the receptor in a constitutively active state.

The below described preferred embodiments illustrate adaptations of these compositions, cells, kits, and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., (2001); and Current Protocols in Molecular Biology, ed. Ausubel et al., Greene Publishing and Wiley-Interscience, New York, (1992) (with periodic updates). Immunology techniques are generally known in the art and are described in detail in methodology treatises such as Current Protocols in Immunology, ed. Coligan et al., Greene Publishing and Wiley-Interscience, New York, (1992) (with periodic updates); Advances in Immunology, volume 93, ed. Frederick W. Alt, Academic Press, Burlington, Mass., (2007); Making and Using Antibodies: A Practical Handbook, eds. Gary C. Howard and Matthew R. Kaser, CRC Press, Boca Raton, Fl, (2006); Medical Immunology, 6th ed., edited by Gabriel Virella, Informa Healthcare Press, London, England, (2007); and Harlow and Lane ANTIBODIES: A Laboratory Manual, Cold Spring Harbor Laboratory Press, Cold Spring Harbor, N.Y., (1988). Conventional methods of gene transfer and gene therapy may also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; Viral Vectors for Gene Therapy: Methods and Protocols, ed. Otto-Wilhelm Merten and Mohammed Al-Rubeai, Humana Press, 2011; and Non-viral Vectors for Gene Therapy: Methods and Protocols, ed. Mark A. Findeis, Humana Press, 2010.

Nucleic Acids and Compositions for Inducing an Immune Response in a Subject

Described herein are nucleic acids encoding LMP1 fusion proteins and compositions including such nucleic acids. The nucleic acids and compositions can be administered to a subject in order to induce an immune response in the subject (e.g., an immune response to a particular antigen) or to modulate an ongoing immune response in a subject (e.g., the naturally occurring but otherwise ineffective immune response to cancer). Nucleic acid molecules encoding LMP fusion proteins and antigens as described herein may be in the form of RNA (e.g., mRNA or synthetic chemically modified RNA) or in the form of DNA (e.g., cDNA, genomic DNA, and synthetic DNA). The DNA may be double-stranded or single-stranded, and if single-stranded, may be the coding (sense) strand or non-coding (anti-sense) template strand.

In one embodiment, a composition for inducing an immune response in a subject includes at least a first nucleic acid encoding at least a first fusion protein, the at least first fusion protein including a transmembrane domain of LMP1 and two or more signaling domains selected from the group of immune activating receptors and/or the group of adaptor proteins, the at least first nucleic acid in an amount sufficient to induce an immune response in a subject. Any suitable immune activating receptor can be used. For example, the immune activating receptor can be a TLR or a TNFSFR. Examples of immune activating receptors include: TLRs 1-13, RIG-1, MDA5, FcγRIII, Dectin1, Dectin2, NOD1, NOD2, CD16, IL-2R, TNFSFR (e.g., CD40, 4-1BB, RANK, TACI, OX40, CD27, GITR, LTβR, and BAFFR), Type I/II interferon receptor, TREM1, RTK, GPCR, Integrin, CCR7, CCR5, BCR (B cell receptor complex proteins). A fusion protein may include a signaling domain from a TLR and a signaling domain from a TNFSFR. Additionally or alternatively, a fusion protein may include a signaling domain from an immune activating receptor and a signaling domain from an adaptor protein. Any suitable adaptor protein may be used. Examples of adaptor proteins include CD3 zeta chain, MyD88, MyD88ΔTIR, IPS-1, TRIF, TRAM, TIRAP, MAL, BTK, RAC1, SYK, NALP3 (NLRP3), NALP3ΔLRR, NALP1, CARD9, DAI, IPAG, STING, Zap70, and LAT. The at least first nucleic acid may further encode an antigen.

Many vectors useful for introducing exogenous nucleic acids into target mammalian cells are available. The vectors may be episomal, e.g. plasmids, virus derived vectors such cytomegalovirus, adenovirus, adeno-associated virus (AAV), lentivirus etc., or may be integrated into the target cell genome, through homologous recombination or random integration, e.g. retrovirus derived vectors such MMLV, HIV-1, ALV, etc. In a typical embodiment, the at least first nucleic acid sequence is contained within a viral vector. In such an embodiment, recombinant virions (particles) containing the viral vector are administered to the subject. Viruses are naturally evolved vehicles which efficiently deliver their genes into host cells and therefore are desirable vector systems for the delivery of therapeutic nucleic acids. Preferred viral vectors exhibit low toxicity to the host cell and produce/deliver therapeutic quantities of the nucleic acid of interest (in some embodiments, in a tissue-specific manner). Retrovirus-based vectors, Lentivirus vectors, adenovirus based vectors, AAV-based vectors, rhabdovirus (e.g. VSV) vectors, poxvirus (e.g. vaccinia) vectors, alphavirus (e.g., Venezuelan equine encephalitis, Semliki Forest virus, Sindbis virus) vectors, and Herpesvirus (e.g., CMV) vectors are examples of viral vectors that may be used. Such recombinant virions may be pseudotyped.

In some embodiments, a composition can include a second nucleic acid encoding a second fusion protein as described herein. In such an embodiment, both the first and second nucleic acids can be contained within a single vector (e.g., a single viral vector) or multiple vectors (e.g., two, three, four, five, etc., viral vectors). A single composition can include two or more nucleic acids, each nucleic acid encoding a single LMP1 fusion protein, or can include two or more nucleic acids, one or more of which encodes multiple LMP1 fusion proteins.

Typically, the at least first nucleic acid (and the second nucleic acid if present) is in an amount effective for activating immune cells (e.g., dendritic cells) when administered to a subject. If a composition is being administered to a subject to prevent or treat a viral infection (e.g., HIV), the at least first nucleic acid (and the second nucleic acid if present) may be in an amount effective for inducing expression of cytokines and protecting primary CD4+ T cells from infection by a virus when administered to a subject. In one embodiment in which the composition is being used to prevent or treat HIV infection, the at least first fusion protein may include a transmembrane domain of LMP1 and a signaling domain from IPS-1. Similarly, if a composition is being administered to a subject to prevent or treat cancer, in one embodiment, the at least first fusion protein may include a transmembrane domain of LMP1 and a signaling domain from IPS-1, and is in an amount effective for preventing growth of a tumor or decreasing the size or growth of an existing tumor in a subject. In this embodiment of preventing or treating cancer, the composition may also include a nucleic acid encoding full-length LMP1 or a portion thereof (e.g., a composition including a nucleic acid encoding an LMP1 fusion protein and full-length LMP1, or a composition including a first nucleic acid encoding an LMP1 fusion protein and a second nucleic acid encoding full-length LMP1).

Also described herein is an LMP1 fusion protein that includes the LMP1 transmembrane domain fused to an amino acid sequence that acts as a cytoplasmic domain and that includes intracellular signaling motifs from two or more (e.g., 2, 3, 4, 5, 6, etc.) TLRs, TNFSFR, or adapter molecules, as well as nucleic acids encoding such fusion proteins. Such an artificial cytoplasmic domain composed of intracellular signaling motifs from multiple TLRs, TNFSFR, or adapter molecules can, as a single gene product, mimic the synergy induced by multiple LMP1 fusion proteins. Such a superactivating LMP1 construct (see FIG. 15, top right box) can be used as a vaccine adjuvant and immune stimulator. In one embodiment, a composition for inducing an immune response in a subject includes a nucleic acid encoding a fusion protein that includes a transmembrane domain of LMP1 and an amino acid sequence having two or more signaling motifs from immune activating receptors and/or adaptor proteins. In the composition, the nucleic acid is in an amount sufficient to induce an immune response in the subject (e.g., an immune response against HIV).

Vaccine formulations and vaccine adjuvants including nucleic acids encoding LMP1 fusion proteins are also described herein. A vaccine formulation for preventing or treating a disease or condition in a subject includes a pharmaceutically acceptable excipient and at least a first nucleic acid or protein encoded by such a nucleic acid for at least a first fusion protein that includes a transmembrane domain of LMP1 and at least one signaling domain from one or more of: an immune activating receptor and/or an adaptor protein. The at least first nucleic acid is in an amount sufficient to induce an immune response in a subject. In an embodiment in which the subject has a viral infection, typically, administration of the at least first nucleic acid induces anti-viral factors that directly reduce viral replication in an infected (e.g., chronically infected) subject. In one embodiment, the composition further includes a second nucleic acid encoding a second fusion protein that includes a transmembrane domain of LMP1 and at least one signaling domain from one or more of: an immune activating receptor and/or an adaptor protein. Typically, the vaccine formulation is administered to vaccinate a subject against cancer or infection. Similarly, a vaccine adjuvant for enhancing an immune response to a vaccine includes a pharmaceutically acceptable excipient and at least a first nucleic acid encoding at least a first fusion protein that includes a transmembrane domain of LMP1 and at least one signaling domain from one or more of: an immune activating receptor and/or an adaptor protein, plus an antigen, in an amount effective for enhancing an immune response to a vaccine (e.g., a conventional or currently available vaccine). Alternatively, the antigen may be encoded by a separate nucleic acid (a second or third nucleic acid). In such a vaccine adjuvant, a second nucleic acid encoding a second fusion protein may be included. In another embodiment, the antigen is administered to a subject in a separate composition. A vaccine formulation or adjuvant may include immune cells (e.g., dendritic cells) transduced with one or more nucleic acids encoding one or more LMP1 fusion protein as described herein.

Methods of Inducing an Immune Response in a Subject

Methods of inducing an immune response against cancer or infection in a subject are described herein. In one embodiment, the method includes administering a composition as described herein to the subject in a therapeutically effective amount for inducing an immune response against the cancer or infection in the subject. In another embodiment, the method includes administering immune cells transduced with one or more nucleic acids encoding one or more LMP1 fusion proteins as described herein to the subject in a therapeutically effective amount for inducing an immune response against the cancer or infection in the subject. In some embodiments, administering the composition to the subject vaccinates the subject against an infection or cancer or enhances the pre-existing immune response to cancer or an ongoing infection. Inducing an immune response against the cancer or the infection in the subject can include activating DCs, maturing DCs, and/or inducing expression of at least one cytokine in the subject. In a method of inducing an immune response against an HIV infection, administration of the composition induces type I interferon expression and/or activity, and protection of primary CD4+ T cells in the subject. In a method of inducing an immune response against cancer in a subject, administration of the composition prevents or decreases growth of cancer cells (e.g., a tumor, leukemia cells, etc.) in the subject. In methods of inducing an immune response against cancer and methods of inducing an immune response against an HIV infection, the at least first fusion protein may include a transmembrane domain of LMP1 and a signaling domain from IPS-1 or a signaling domain from MyD88. In such a method, the nucleic acid encoding the at least first fusion protein may also encode a full-length LMP1 protein.

An immune response may include the activation of immune cells such as dendritic cells (DCs). DCs are a part of the immune system that act as APCs. DCs process antigen material and present it on their cell surface using MHC molecules. Pattern recognition receptors, such as TLRs, assist the DCs in detecting viruses and bacteria. After a DC is activated, it migrates to the lymph nodes. DCs interact with other cells within the immune system such as T cells and B cells. Stimulated DCs produce IL-12. IL-12 helps naïve CD4+ T cells obtain a T helper cell type 1 (Th1) phenotype. Cytokines cause the development of T helper cell type 1 (Th1) and T helper cell type 2 (Th2) cells from naïve CD4+ T cells. The Th phenotypes each produce particular cytokines and can be identified by specific cell-surface markers.

An immune response may be mounted to an antigen or antigens from any pathogen as a result of vaccination against that antigen or antigens. In one embodiment, the antigen may be derived from, but not limited to, pathogenic bacterial, fungal, or viral organisms, including *Streptococcus* species, *Candida* species, *Brucella* species, *Salmonella* species, *Shigella* species, *Pseudomonas* species, *Bordetella* species, *Clostridium* species, Norwalk virus, *Bacillus anthracia, Mycobacterium tuberculosis*, HIV, *Chlamydia* species, human Papillomaviruses, Influenza virus, Parainfluenza viruses, Paramyxovirus species, Herpes virus, Cytomegalovirus, Varicella-Zoster virus, Epstein-Barr virus, Hepatitis viruses (including HAV, HBV, and HCV), flaviviruses (including dengue and West Nile virus), filoviruses (including Ebola), coronaviruses (including SARS and MERS), *Plasmodium* species, *Trichomonas* species, *Leishmania* species, *Neisseria meningitides*, sexually transmitted disease agents, viral encephalitis agents, protozoan disease agents, fungal disease agents, and bacterial disease agents. A subject may be treated for any infectious pathogen, including those listed herein.

In some embodiments, the antigen is derived from cancer cells. The vaccine may be used against any cancer or with any other therapy or intervention for cancer. Examples of cancers include HPV-induced cervical cancers (e.g., E7/E7 tumor associated antigens (TAA)), glioma, human melanoma (e.g., TRP-1, TRP-2, gp-100, MAGE-1, MAGE-3 and/or p53), breast cancer, and prostate cancer (e.g., TSA). Similarly for lung tumors, breast tumors, and leukemia, any suitable tumor associated antigen can be used, and many have been described. Many such TAA are common between various cancers (e.g., CEA, MUC-1, Her2, CD20). In addition, tumor cells may have uncategorized antigens such as those created by gene mutations (e.g., BRAF V600E in melanoma), gene transpositions (e.g., BCR-abl in chronic myelogenous leukemia), or simply tumor rejection antigens caused by overexpression of normal genes (e.g., telomerase).

The compositions, cells, kits, vaccines, vaccine adjuvants, and methods described herein solve the problem of properly activating and maturing DCs for therapeutic vaccination of DCs into patients as a treatment for cancer or chronic infections. They may also be used to develop prophylactic vaccines and other immune therapies dependent on immune activation.

In some embodiments, prior to or after administration of a composition or transduced immune cells as described herein to a subject, the subject's immune response is analyzed or measured. Any suitable biological sample can be tested for analyzing or measuring a subject's immune response. Examples of biological samples include blood, serum, plasma, urine, saliva and tissue. The sample may be tested using any suitable protocol or assay. Examples of suitable assays include enzyme-linked immunosorbent assays (ELISAs), Western blots, flow cytometry assays, immunofluorescence assays, qPCR, microarray analysis, etc.

Dendritic Cell Therapy

Immune cells such as dendritic cells transduced with nucleic acids encoding LMP1 fusion proteins can be used as an effective reagent for cell therapy for a subject in need thereof (e.g., a human subject having cancer or chronic infection). Immune cells (e.g., human dendritic cells) transduced with a nucleic acid or composition as described herein are encompassed within the invention. LMP1 fusion proteins can costimulate the activation of the transduced DC while allowing the transduced DC to induce T cell memory with secretion of IL-12 cytokine. Nucleic acids encoding LMP fusion proteins as described herein may be transfected into immune cells such as DCs. Alternatively, a viral vector may be used to introduce such a nucleic acid into immune cells (e.g., infection of the cells by a recombinant virus). The DCs may also be transduced with an antigen (e.g., an antigen encoded by the nucleic acid encoding an LMP1 fusion protein, an antigen encoded by a separate nucleic acid).

Administration of the DCs transduced with one or more nucleic acids encoding one or more LMP1 fusion proteins to a subject can induce an immune response against cancer or infection including secretion of IL-12 by the DCs and activation of Th1 cells. An example is provided in FIG. 7.

Given that DC therapy often uses RNA encoding the antigen or immune stimulatory proteins for transfection, LMP1 fusion proteins can also be transfected as RNA. RNA is a safer method of transfection compared to DNA or viral vectors, given that RNA cannot integrate into the genome or be maintained. The RNA is degraded over time, and therefore LMP1 encoded as RNA would not persist in the patient after treatment.

The compositions, nucleic acids, and cells described herein may be administered in combination with any other standard cell (e.g., DC) therapy; such methods are known to the skilled artisan and described in Remington's Pharmaceutical Sciences by E. W. Martin.

Kits for Inducing an Immune Response in a Subject

Described herein are kits for inducing an immune response and preventing or treating a disease or condition in a subject and for preparing a vaccine formulation. In one embodiment, a kit for inducing an immune response in a subject includes a composition including at least a first nucleic acid encoding at least a first fusion protein, the at least first fusion protein including a transmembrane domain of LMP1 and at least one signaling domain from at least one of: an immune activating receptor and/or an adaptor protein. In the composition, the at least first nucleic acid is in an amount sufficient to induce an immune response in a subject. In another embodiment, the composition includes a second nucleic acid encoding a second fusion protein, the second fusion protein including a transmembrane domain of LMP1 and at least one signaling domain from at least one of: an immune activating receptor and/or an adaptor protein. In some embodiments, the at least first nucleic acid also encodes an antigen. A kit as described herein can include a vaccine formulation that includes one or more nucleic acids encoding one or more LMP fusion proteins or a formulation that includes the proteins themselves. Similarly, a kit can include a vaccine adjuvant as described herein. In a kit, the instructions generally include one or more of: a description of the composition; dosage schedule and administration for prevention or treatment (e.g., vaccination) of cancer or infectious disease; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container. Generally, a kit as described herein also includes packaging. In some embodiments, the kit includes a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding cells or medicaments.

Effective Doses

The compositions, vaccines and cells described above are preferably administered to a mammal (e.g., non-human primate, bovine, canine, rodent, human) in an effective amount, that is, an amount capable of producing a desirable result in a treated subject (e.g., delaying or preventing onset of a disease or disorder in the subject). Toxicity and therapeutic efficacy of the compositions utilized in methods described herein can be determined by standard pharmaceutical procedures. As is well known in the medical and veterinary arts, dosage for any one animal depends on many factors, including the subject's size, body surface area, age, the particular composition to be administered, time and route of administration, general health, and other drugs being administered concurrently.

The amount of the therapeutic agent to be administered varies depending upon the manner of administration, the age and body weight of the patient, and with the pathology of the disease. A composition as described herein is typically administered at a dosage that activates and matures dendritic cells, as assayed using any assay that measures activation or maturation of dendritic cells, such as analyzing expression of one or more of: IL-1α, IL-1β, IFN-α, IFN-β, IFN-γ, IL-2, IL-4, IL-6, IL-10, IL-12, IL-15, IL-16, IL-17, IL-18, and TNF-alpha.

Therapeutic compositions described herein can be administered to a subject by any suitable delivery vehicle (e.g., DNA plasmid, RNA, viral vector, recombinant virions, or purified protein) and route. The administration of a composition may include a therapeutically effective amount of a vaccine formulation or vaccine adjuvant. The composition may be provided in a dosage form that is suitable for local or systemic administration (e.g., parenterally, subcutaneously, intravenously, intramuscularly, intraperitoneally, intracranially). In various embodiments, the composition may be provided in a dosage form that is suitable for oral administration or intranasal administration. The compositions and vaccines may be formulated according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999)).

Compositions, vaccines, vaccine adjuvants, and cells as described herein may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. Apart from the agent that activates immune cells (e.g., activates and matures dendritic cells), the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Formulations for oral use include a liquid containing the active ingredient(s) (e.g., a nucleic acid encoding an LMP1 fusion protein) in a mixture with non-toxic pharmaceutically acceptable excipients.

EXAMPLES

The present invention is further illustrated by the following specific examples. The examples are provided for illustration only and should not be construed as limiting the scope of the invention in any way.

Example 1

Constitutively active gene-encoded combinations of cell receptor signaling domains and signaling adapter molecules.

The current technology uses TLR agonist chemicals and CD40 stimulation with agonistic antibodies. These methods rely on the presence of TLR and TNRSFR on the surface of immune cells. If those receptors are not present, or are downregulated, activation will be reduced. It would be preferable to have constitutive activation of the receptors independent of native expression by the cell. In the experiments described herein, combinations of LMP1-TLRs, LMP1 fused to intracellular signaling adapter molecules, and LMP1-TNFSFR were shown to induce activation of the immune response.

A model of LMP1 fusion protein technology is illustrated in FIG. 1. In FIG. 1(A), the structure of LMP1 is shown. LMP1 contains a cytoplasmic signaling domain connected to a 6-segment transmembrane domain that aggregates the protein and anchors it in the cell membrane. The compositions, cells, vaccines, kits and methods described herein are based on the demonstration that LMP1 is immunostimulatory and the cytoplasmic domain can be replaced by any immune signaling domain to create novel chimeras of LMP1 fusion proteins. In FIG. 1(B), the LMP1 fusion protein concept is shown on the right. The LMP1 transmembrane/aggregation domain can be linked to multiple intracellular signaling domains from immune activating receptors (e.g., TLR3), from adapter proteins that interact with immune activating receptors (e.g., MyD88), and/or adaptor proteins further downstream in both adaptive and innate immune activation signaling (e.g., IPS-1). In FIG. 1(C), a model of a DNA or viral vector vaccine using LMP1 fusion proteins is shown. Antigen and LMP1 fusion proteins are encoded within the same polypeptide strand encoded by a nucleic acid (DNA, RNA, or viral vector genome) and directed to an immune cell. Following the introduction of the LMP1 fusion protein, the cell produces antigen protein that is cleaved into antigenic peptides for presentation to T cells on MHC plus a constitutive immune activation signal from the cell signaling domains in the LMP1 fusion protein. This immune activation signal induces cell activation and/or maturation and/or release of pro-inflammatory cytokines, and results in the induction of an effective immune response against the pathogen.

Figure 2:
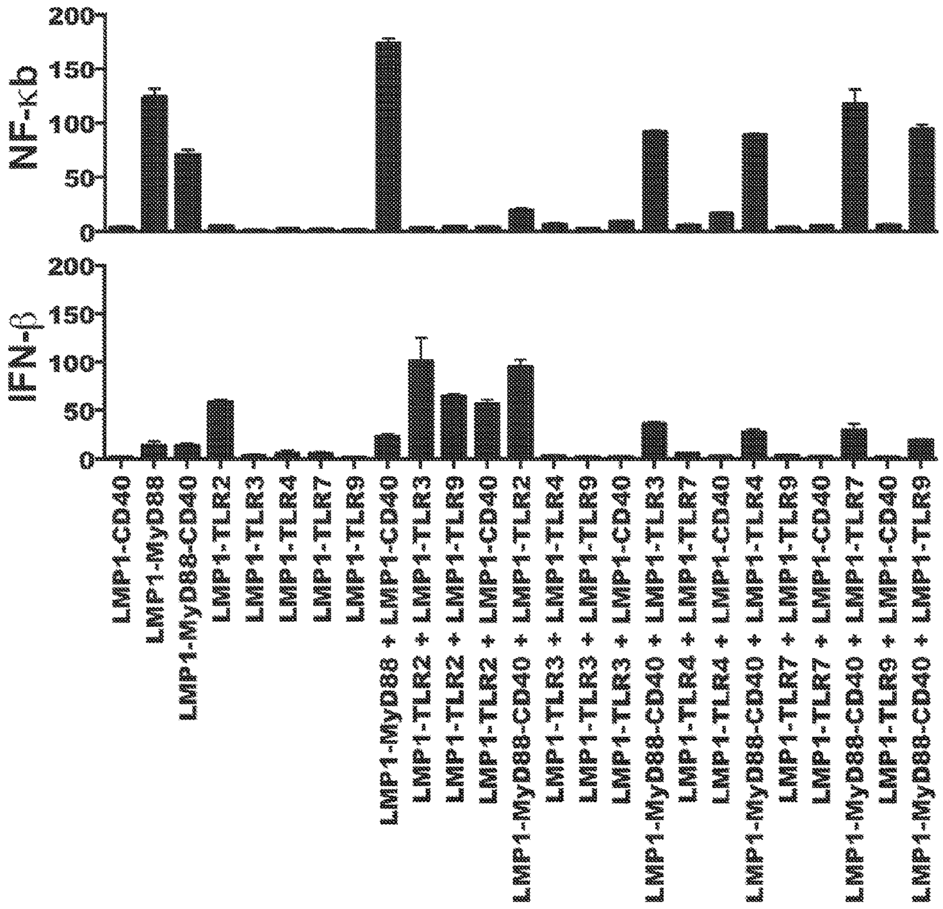
FIG. 2 is a series of graphs of results showing that LMP1 fusion proteins with TLR, PRR, CD40, and/or signaling adapter proteins are potent inducers of NF-κB and IFN-β responses.
Figure 2:
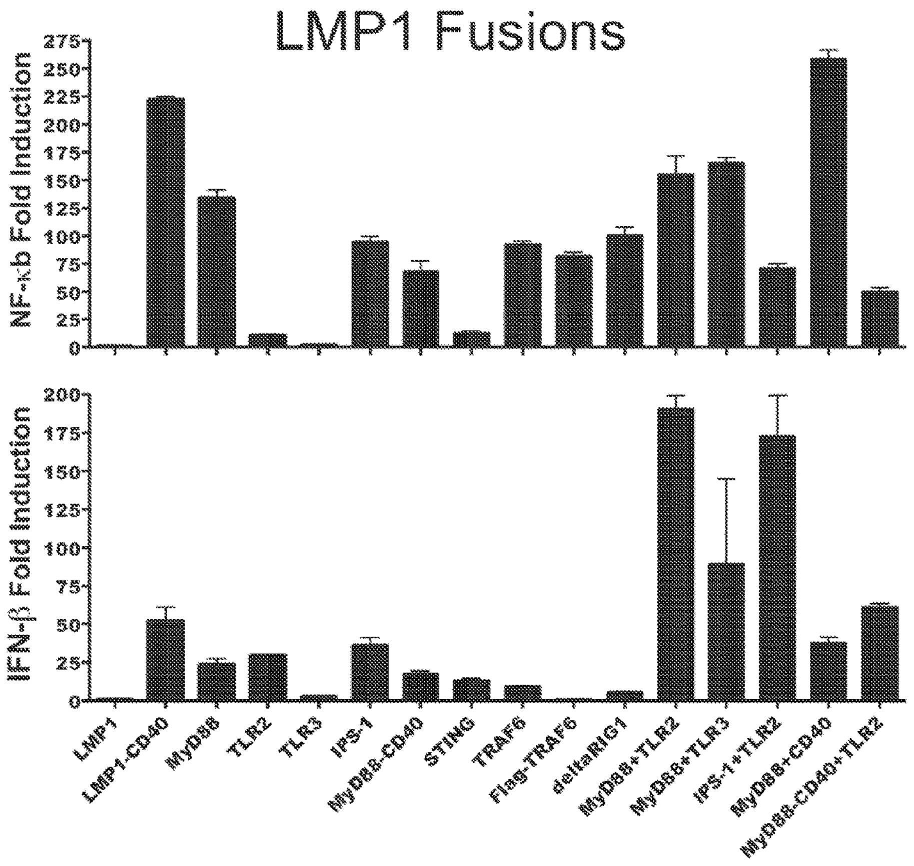
Figure 2:
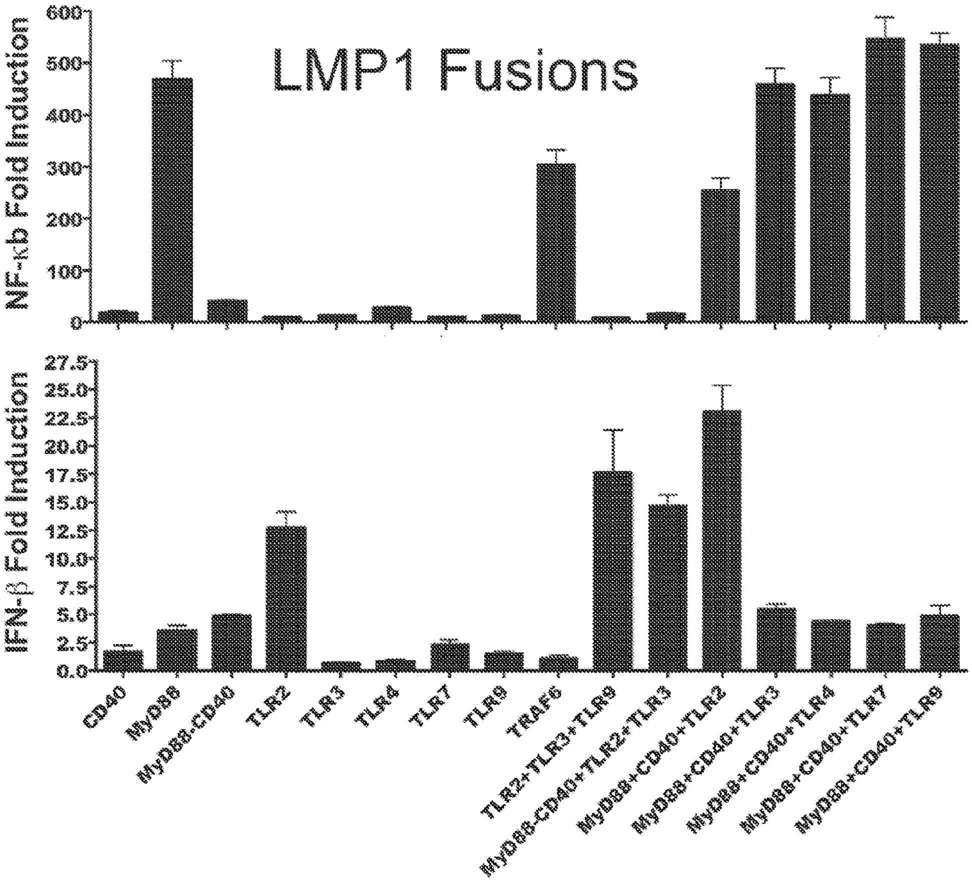

Referring to FIG. 2, LMP1 fusion proteins with TLR, PRR, CD40, and/or signaling adapter proteins are potent inducers of NF-κB and IFN-β responses. 293 cells were co-transfected with an NF-κB or IFN-β promoter Luciferase reporter construct and plasmid DNA encoding one or more human or mouse LMP1 fusion proteins. All the constructs indicated are fused to the transmembrane domain of LMP1 with the exception of Flag-TRAF6 and deltaRIG-I which do not contain LMP1 and are shown as positive controls for NF-κB and IFN-β induction. The construct labeled MyD88-CD40 contains a 3-protein fusion of LMP1, the MyD88 adapter protein, and the intracellular domain of CD40. In other samples two or more LMP1 fusion proteins were co-transfected into the 293 cells (i.e. MyD88+CD40 or TLR2+TLR3+TLR9). Certain LMP1 fusion proteins and LMP1 fusion protein combinations increased NF-κB mediated activity compared to parent LMP1. Expression was normalized to a pcDNA3.1 empty vector control.

Referring to FIG. 3, LMP1 fusions with IPS-1, TLR7, and MyD88-CD40 enhance activation and IL-6 cytokine secretion from a RAW 264.7 mouse macrophage cell line. Cells were transfected with either parent vector pcDNA3.1 or various LMP1 fusion constructs with murine proteins. LMP1-MyD88-CD40 refers to a single fusion protein containing the LMP1 transmembrane domain, MyD88, and the intracellular domain of CD40. MyD88dTIR-CD40 refers to an LMP1 fusion protein containing the LMP1 intracellular domain, MyD88 with a deletion of the TIR domain, and the CD40 intracellular domain. Cells were transfected using Lipofectamine LTX reagent. Levels of cell surface proteins were measured by Mean Fluorescence Index (MFI), and cytokines by cytometric bead array. The surprising result is that LMP1-IPS-1 fusion protein generated high levels of IL-6 and induced both maturation (CD40, CCR7) and activation (CD80, CD86) markers on the macrophage cell line. LMP1-TLR7 and LMP1-MyD88-CD40 were able to generate responses superior to wildtype LMP1, suggesting these fusion proteins are particularly potent immune activators. Dashed line denotes MFI of the pcDNA3.1 control. * $p<0.05$,  $p<0.01$, * $p<0.001$.

Figure 4:
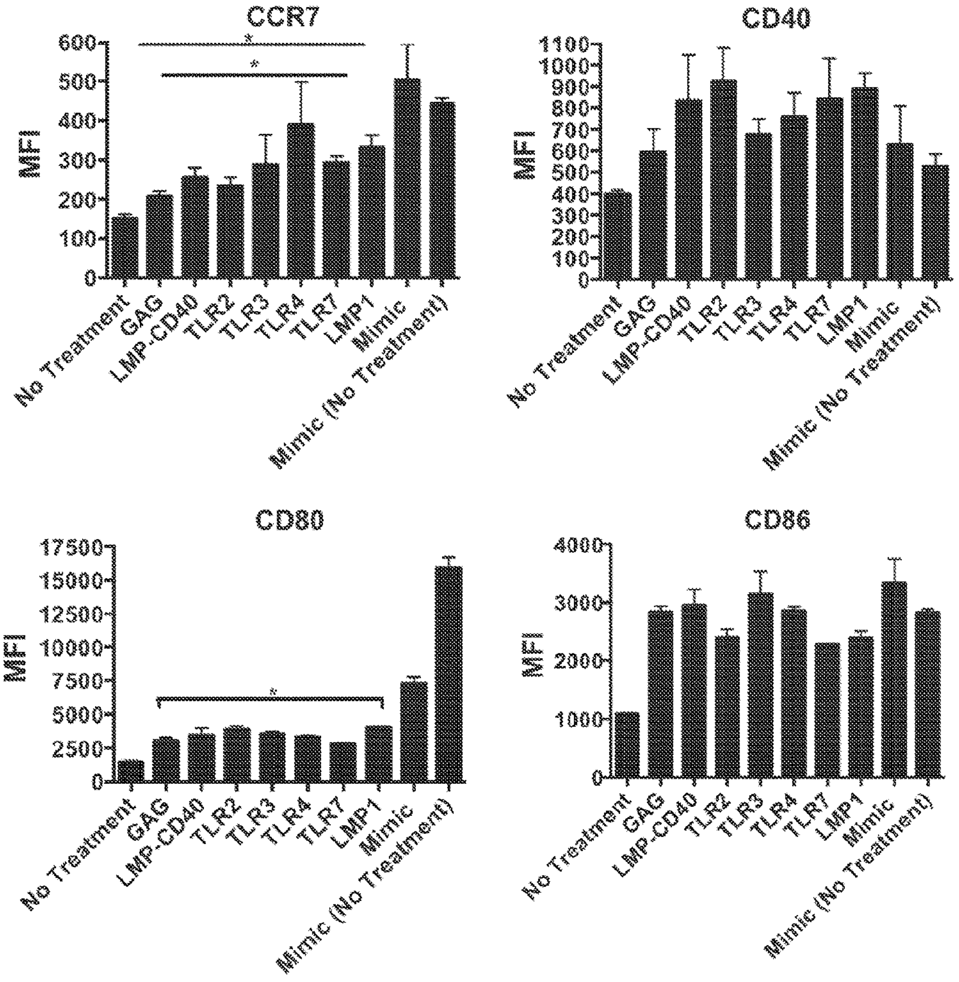
FIG. 4 is a series of graphs of results showing that human monocyte derived DCs transfected with LMP1-TLR fusion constructs induce activation, maturation, and cytokine secretion.
Figure 4:
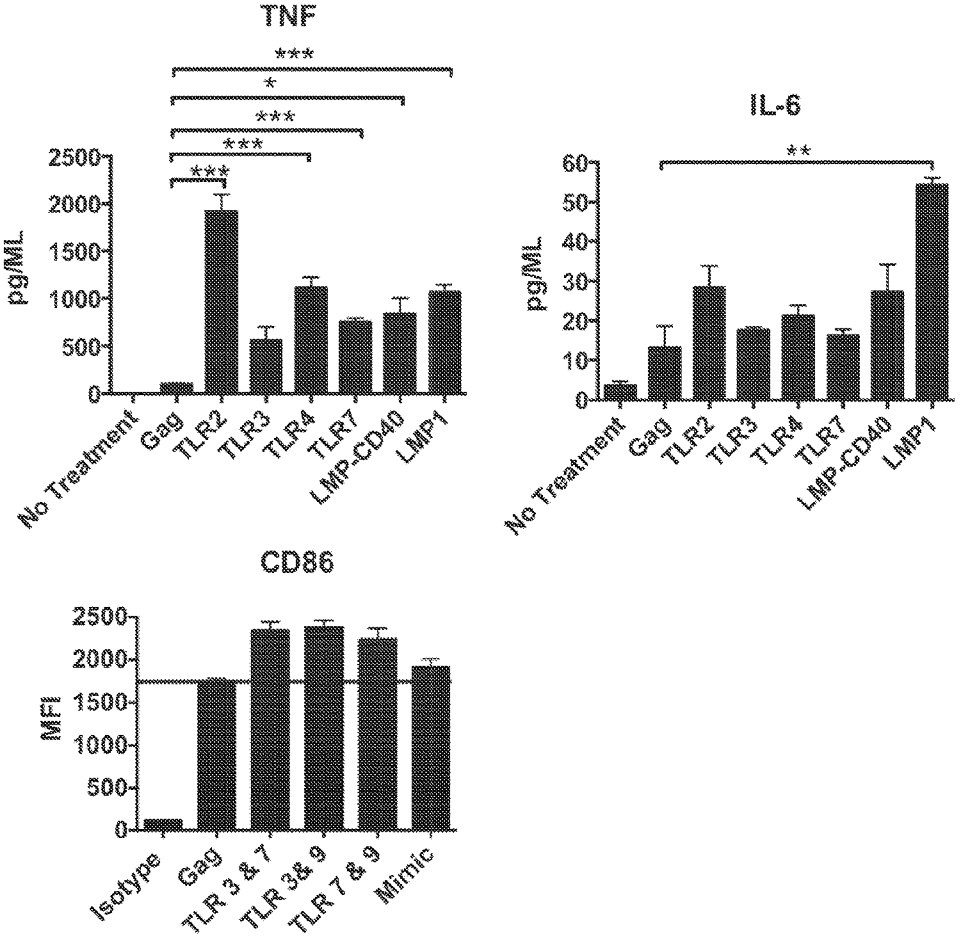

Referring to FIG. 4, human monocyte derived DCs transfected with LMP1-TLR fusion protein constructs induce activation, maturation, and cytokine secretion. All TLR and CD40 constructs refer to LMP1 fusion proteins (i.e. TLR2 refers to LMP1-TLR2 fusion). Human DCs were electroporated with RNA encoding either control Gag protein or LMP1 fusions with human TLR and CD40 genes. The "Mimic" cytokine mix (consisting of a mixture of TNF, IL-1-beta, IL-6, and PGE2) was used as a positive control (with or without electroporation with Gag RNA). LMP1 and LMP1-TLR7 fusions induced a significant increase in CCR7 expression as measured by mean fluorescence index. All LMP1 fusions had a trend toward increased expression of the maturation marker CD40 and the activation marker CD80. All LMP1 fusion protein constructs increased secretion of the pro-inflammatory cytokine TNF-alpha and had a trend toward increased secretion of IL-6. Combinations of LMP1-TLR3, LMP1-TLR7, and LMP1-TLR9 were able to induce DC maturation compared to antigen alone or Mimic cytokine mix stimulation. * $p<0.05$,  $p<0.01$, * $p<0.001$.

Figure 5:
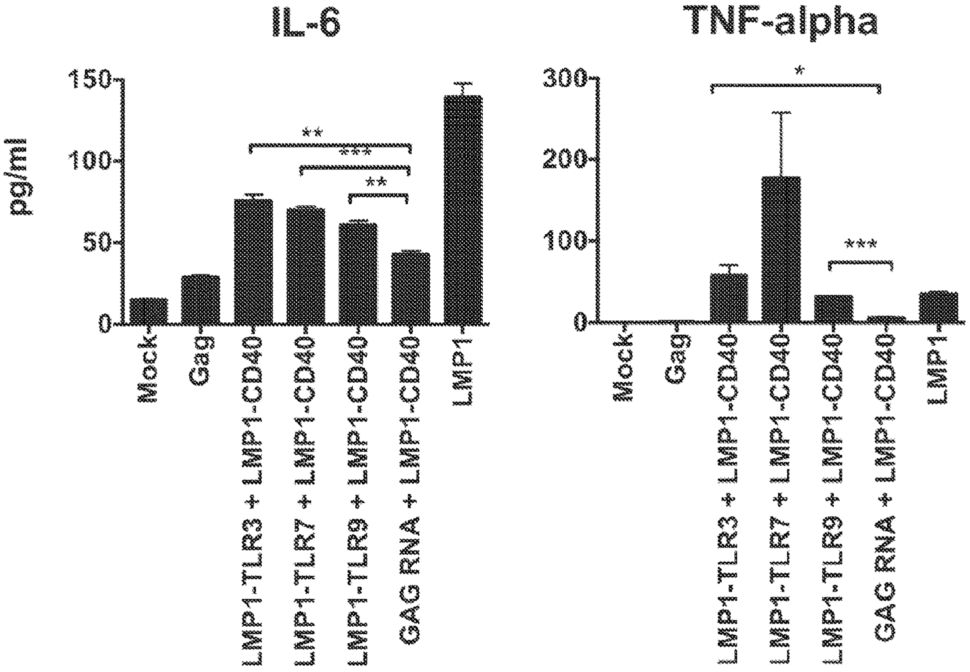
FIG. 5 is a pair of graphs of results showing that combinations of LMP1-CD40 with LMP1-TLR fusions enhanced maturation, activation, and secretion of pro-inflammatory cytokines from human DC.

Referring to FIG. 5, DCs transfected with combinations of LMP1-CD40 with LMP1-TLR fusion protein RNAs enhanced maturation, activation, and secretion of pro-inflammatory cytokines from human DC. Monocyte derived DC were electroporated with control (Gag) RNA or equal mixtures of LMP1-CD40 RNA with either Gag (a non-activating protein from HIV-1) or LMP1-TLR fusions. Combinations of LMP1-TLR fusions with LMP1-CD40 significantly increased secretion of the pro-inflammatory cytokines IL-6 (LMP1-TLR3, LMP1-TLR7, LMP1-TLR9 fusions) and TNF-alpha (LMP1-TLR3 and LMP1-TLR9 fusions) compared to LMP1-CD40 plus irrelevant control RNA (Gag). These data show for the first time that fusion of a TLR cell signaling domain to the LMP1 N-terminal transmembrane domain is sufficient to engage the TLR signaling pathway to activate cells.

Figure 6:
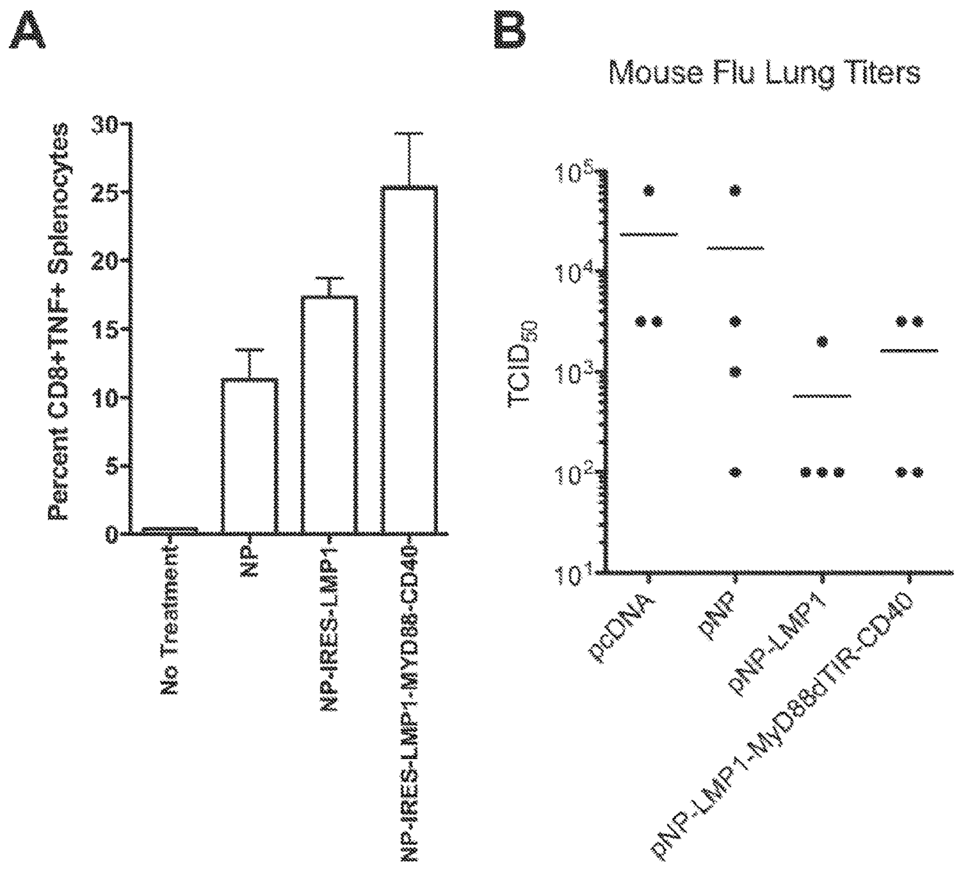
FIG. 6 is a series of graphs of results showing that LMP1-MyD88-CD40 fusion enhances immune responses and control of viral infection in a mouse influenza DNA vaccine model.
Figure 6:
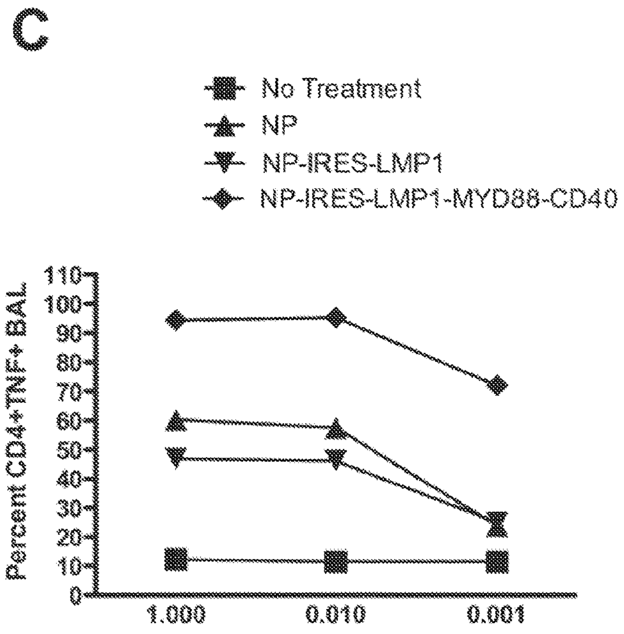

Referring to FIG. 6, antigen-LMP1-MyD88-CD40 fusion protein enhances immune responses and control of viral infection in a mouse influenza DNA vaccine model. C57BL/6 mice were vaccinated with 100 ug of plasmid DNA by intramuscular injection into the quadriceps muscles of both hindlimbs every two weeks for a total of 3 vaccinations. Seven days following the final vaccination, some of the mice were sacrificed and immune cells were harvested from their spleens or collected from their lungs by bronchoalveolar lavage (BAL). In parallel to this study, other mice were given an intranasal challenge with a standardized dose of live influenza A PR8 virus two weeks after the last vaccination and then sacrificed 4 days later to determine the amount of influenza viruses in lung tissue as determined by tissue culture 50% infectious dose (TCID50) units. The vaccinations used plasmids expressing the nucleoprotein (NP) antigen from Influenza A PR8 strain alone, or the NP antigen plus either full-length LMP1 (which includes its cell signaling domain) or NP antigen plus LMP1-MyD88-CD40 fusion protein. For the fusions with NP antigen, the nucleic acid sequences included an internal ribosome entry sequence (IRES) placed between the NP antigen coding sequence and the LMP1 or LMP1-MyD88-CD40 fusion sequence. This results in a single mRNA strand that is read by ribosomes from its 5' cap to translate the NP antigen until the ribosome reaches the in-frame stop codon after which the mRNA is released from the ribosome but is then available via the IRES to commence translation from at an internal ATG start codon for the translation of LMP1 or LMP1-MyD88-CD40 as a polypeptide that is separate from the NP antigen. As indicated schematically in FIG. 1C using a DC as an exemplary immune cell, the NP antigen polypeptide is available for proteolytic processing into peptides presented to T cells on MHC-I or MHC-II. At the same time, the separate LMP1 or LMP1-MyD88-CD40 polypeptide is available to anchor into the membrane and activate cell signaling pathways. As shown in FIG. 6, this design resulted in a superior vaccine response to this DNA vaccine. In the upper panels, splenocytes were exposed to NP antigen, incubated overnight, and then surface stained for either CD8 or CD4 and intracellularly stained for TNF using fluorochrome-labeled antibodies, and then analyzed for CD4, CD8, and TNF production by flow cytometry. When compared to DNA vaccination a plasmid for NP antigen alone, vaccination with plasmids for NP-IRES-LMP1 or especially vaccination with NP-IRES-MyD88-CD40 elicited significantly higher levels of NP-specific CD8+ T cells in the spleen and NP-specific CD4+ T cells in the lung BAL samples. For the CD8+ T cell response, as little as 0.001 ug/ml of NP peptide could stimulate these cells, a very low amount that indicates these CD8+ T cells have very high avidity for antigen, which is recognized in the art to be an in vitro correlate of strong protective function in vivo. These ex vivo measures of immune responses were confirmed in vivo by showing (bottom panel) that DNA vaccination with NP-IRES-LMP1 or NP-IRES-MyD88-CD40 protected mice from challenge by live influenza virus (where the horizontal line indicated the geometric mean of the lung viral loads in 3-4 mice).

Figure 7:
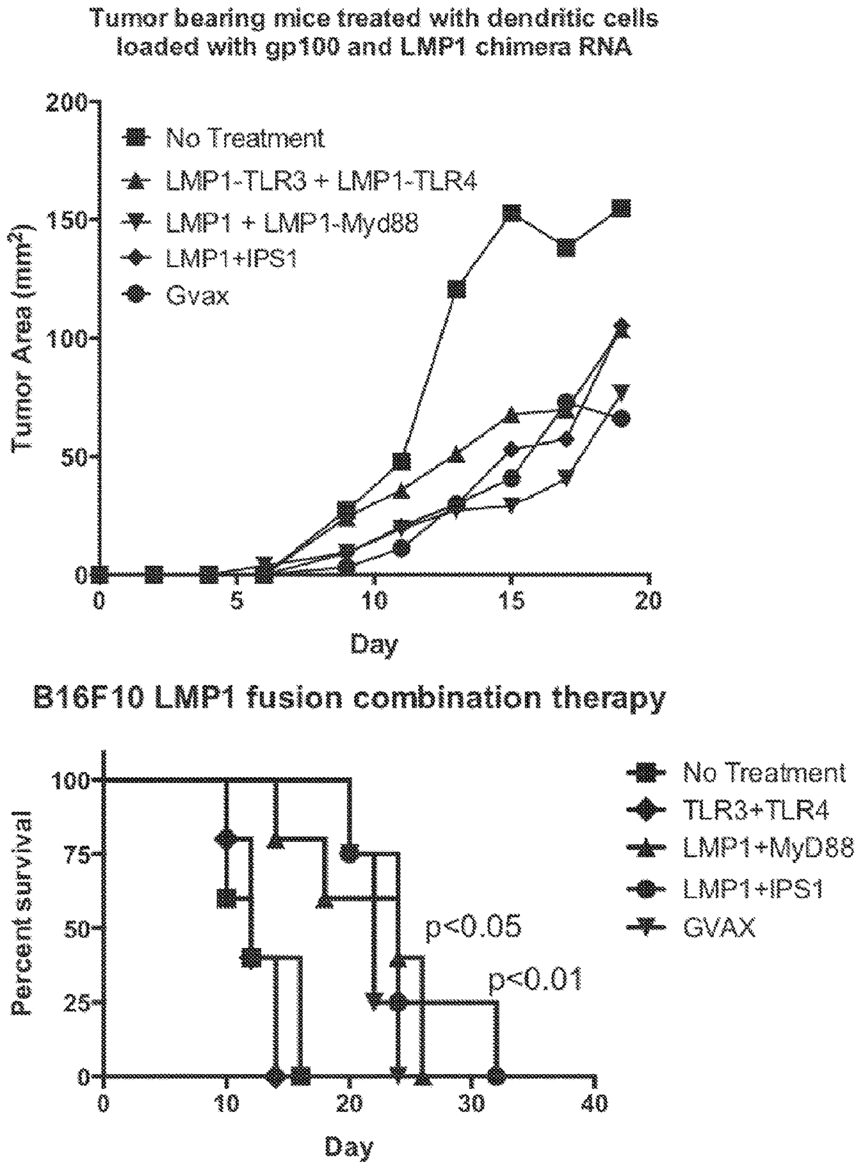
FIG. 7 is a pair of graphs of results showing enhanced survival and reduced tumor growth using LMP1 fusion combinations as a dendritic cell cancer therapy.

Referring to FIG. 7, enhanced survival and reduced tumor growth using LMP1 fusion combinations as a dendritic cell cancer therapy was demonstrated. C57BL/6 mice were injected subcutaneously on the flank with 50,000 B16-F10 melanoma cells and tumors size measured every other day. Three days post-tumor injection, mice were given a total of 1 million C57BL/6 bone marrow derived dendritic cells subcutaneously into the flank opposite the tumor. 24 hours prior to injection these dendritic cells were electroporated with RNA encoding gp100 melanoma antigen plus a combination of RNAs encoding LMP1 and/or LMP1 fusion proteins, including LMP1, LMP1-TLR3, LMP1-TLR4, LMP1-MyD88, and LMP1-IPS1. Dendritic cells were given to mice every 3 days for a total of three treatments. As a control, mice were treated with GVAX therapy (irradiated B16-F10 cells expressing GM-CSF injected intradermally on the opposite flank every 3 days for a total of 3 treatments). Dendritic cells expressing a combination of gp100 tumor antigen plus LMP1 and LMP1-MyD88 or gp100 tumor antigen plus LMP1 and LMP1-IPS-1 were able to enhance survival ($p<0.05$ and $p<0.01$ respectively) when compared to untreated tumors. Overall tumor growth was slowed in mice treated with these LMP1 fusion combinations.

Example 2

Control of HIV replication by a novel constitutively active "Super-PRR"

Innate immune responses are key determinants of the outcome of HIV infection, influencing critical events in the earliest stages of infection. Innate antiviral immune defenses are triggered through the recognition of conserved pathogen associated molecular pattern (PAMP) motifs within viral products by intracellular pattern recognition receptor (PRR) proteins in infected cells. Type I interferons (IFN$\alpha$ and $\beta$) are induced directly in response to viral infection, resulting in an antiviral state for the cell. IFN-$\beta$ promoter stimulator (IPS-1), also known as mitochondrial antiviral signaling protein (MAVS), virus-induced signaling adaptor (VISA), and CARD adaptor inducing IFN-$\beta$ (Cardif), was recently identified as an adaptor linking RIG-I and Mda5 to the downstream signaling molecules, which has been found to have roles in anti-viral immune responses. LMP1 and chimeric LMP1-CD40 has been shown to increase maturation and activation of dendritic cells and macrophages and induce strong TH1 cytokine responses. In this study, the role of chimeric LMP1-IPS-1 fusion molecule in immune activation and anti-viral immune response was examined for the prevention of HIV-1 replication.

Results

Figure 8:
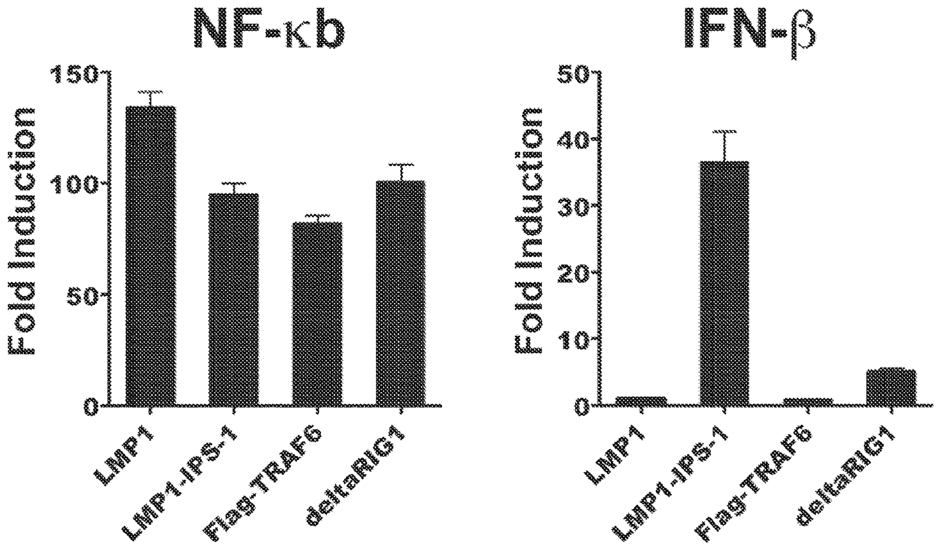
FIG. 8 is a pair of graphs of results showing that LMP1-IPS-1 is a potent inducer of NF-κB and IFN-β responses.

Referring to FIG. 8, LMP1-IPS-1 is a potent inducer of NF-κB and IFN-β responses. 293 cells were co-transfected with an NF-κB or IFN-β promoter luciferase reporter construct and LMP1-IPS-1 along with controls LMP1, Flag-TRAF6 and deltaRIG-I. LMP1-IPS-1 increased IFN-β mediated activity compared to parent LMP1. Expression was normalized to a pcDNA3.1 empty vector control.

Figure 9:
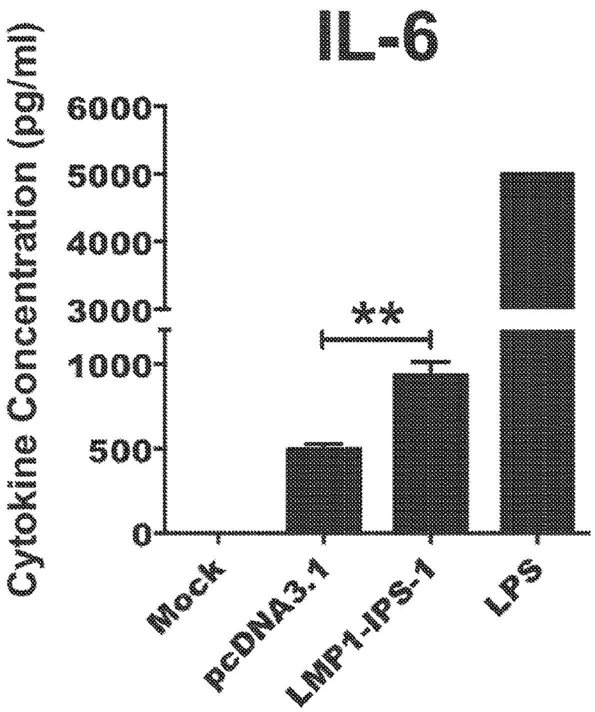
FIG. 9 is a graph of results showing that LMP1-IPS-1 enhances IL-6 secretion from RAW 264.7 mouse macrophage cell line.

Referring to FIG. 9, LMP1-IPS-1 induces high IL-6 levels from RAW 264.7 mouse macrophage cell line. Cells were transfected with either parent vector pcDNA3.1 or LMP1-IPS-1 construct. Cells were transfected using Lipofectamine LTX reagent. Levels of cytokines were measured by cytometric bead array (CBA). The LMP1-IPS-1 fusion protein generated high levels of IL-6 from the macrophage cell line suggesting that LMP1-IPS-1 as potent immune activator. ** $p<0.01$.

Figure 10:
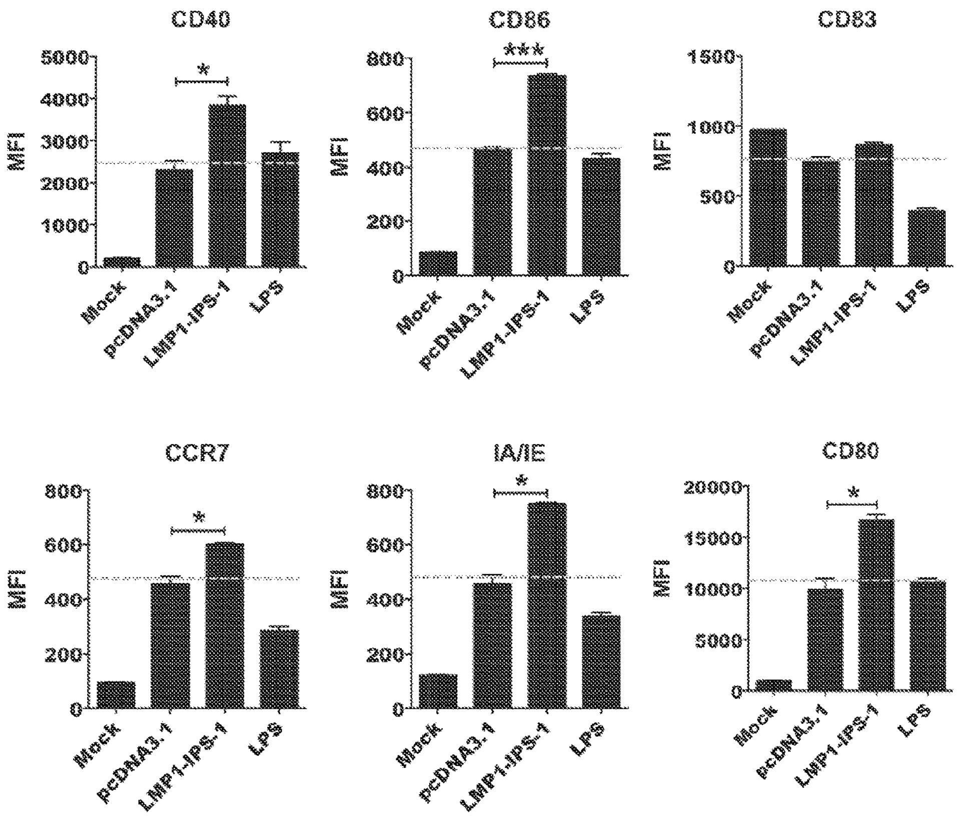
FIG. 10 is a series of graphs showing that LMP1-IPS-1 enhances activation of RAW 264.7 mouse macrophage cell line.

Referring to FIG. 10, LMP1-IPS-1 causes activation of a RAW 264.7 mouse macrophage cell line. Cells were transfected with either parent vector pcDNA3.1 or LMP1-IPS-1 construct. Cells were transfected using Lipofectamine LTX reagent. Levels of cell surface proteins was measured by Mean Fluorescence Index (MFI). The LMP1-IPS-1 fusion protein generated both maturation (CD40, CCR7) and activation (CD80, CD86) markers on the macrophage cell line suggesting that LMP1-IPS-1 is potent immune activator. Dashed line denotes MFI of the pcDNA3.1 control. * $p<0.05$,  $p<0.01$, * $p<0.001$.

Figure 11:
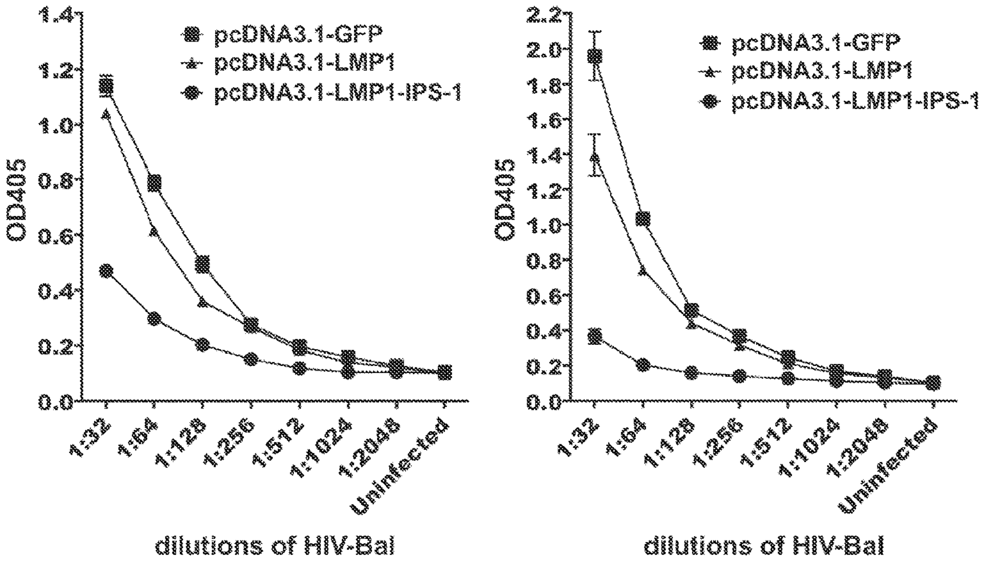
FIG. 11 is a pair of graphs of results showing that a LMP1-IPS-1 fusion protein is able to protect cells from HIV-1 infection and/or replication.

Referring to FIG. 11, LMP1-IPS-1 prevents the replication of HIV-1 in TZM-bl cells in cis as well as in trans. In FIG. 11(A), TZM-bl cells, a HeLa cell line expressing CD4, CCR5, and a HIV-1 promoter β-galactosidase reporter gene, were transfected with plasmids expressing either EGFP (control), LMP1, or LMP1-IPS-1. Cells were then infected with serial dilutions of HIV-1 BaL strain. The level of HIV-1 infection was measured by β-galactosidase ELISA assay. The LMP1-IPS-1 fusion was able to protect TZM-bl cells from infection, providing evidence that LMP1-IPS-1 is able to induce cytokines and other innate antiviral mechanisms in this cell line. In FIG. 11(B), TZM-bl cells were cultured in a transwell assay with 293T cells that were transfected with LMP1-IPS1 expressing or control plasmids suggesting that soluble factors produced by LMP1-IPS1 expressing cells can effectively inhibit HIV-1 replication in TZM-bl cells.

Figure 12:
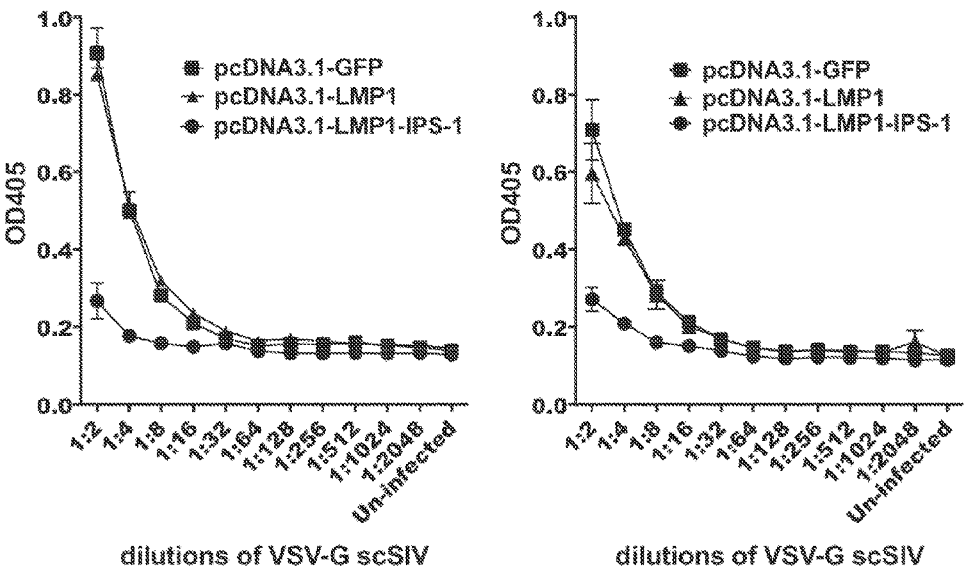
FIG. 12 is a pair of graphs of results showing that LMP1-IPS-1 fusion protein is able to protect cells from single cycle SIV infection and/or replication.

Referring to FIG. 12, LMP1-IPS-1 prevents the replication of VSV-G pseudotyped scSIV in TZM-bl cells in cis as well as in trans. In FIG. 12(A), TZM-bl cells, a HeLa cell line expressing CD4, CCR5, and a HIV-1 promoter β-galactosidase reporter gene, were transfected with plasmids expressing either EGFP (control), LMP1, or LMP1-IPS-1. Cells were then infected with serial dilutions of VSV-G pseudotyped scSIV. The level of SIV infection was measured by β-galactosidase ELISA assay. The LMP1-IPS-1 fusion was able to protect TZM-bl cells from infection, providing evidence that LMP1-IPS-1 is able to induce cytokines and other innate antiviral mechanisms in this cell line independent of Env mediated fusion. In FIG. 12(B), TZM-bl cells were cultured in a transwell assay with 293T cells that were transfected with LMP1-IPS1 expressing or control plasmids suggesting that soluble factors produced by LMP1-IPS1 expressing cells can effectively inhibit SIV replication in TZM-bl cells.

Figure 13:
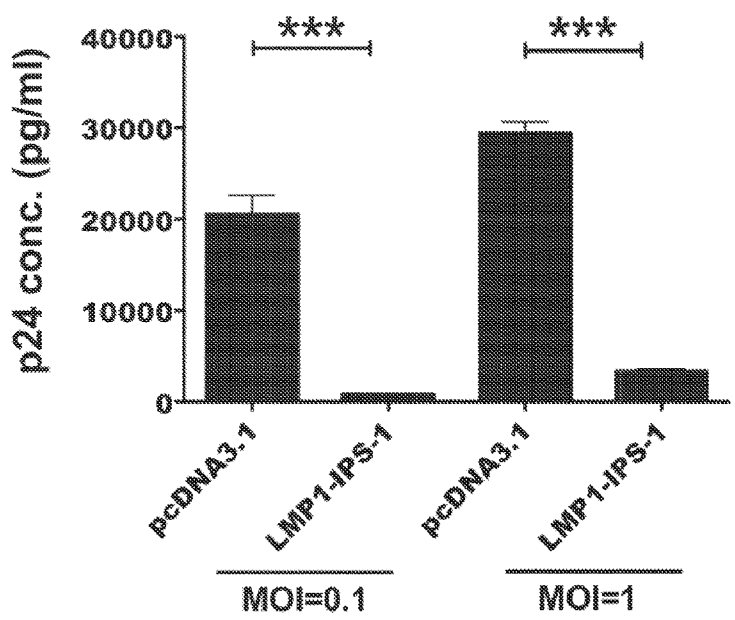
FIG. 13 is a graph of results showing that soluble factors produced by LMP1-IPS1 expressing cells can effectively inhibit HIV-1 in primary CD4+ human T cells.
Figure 14:
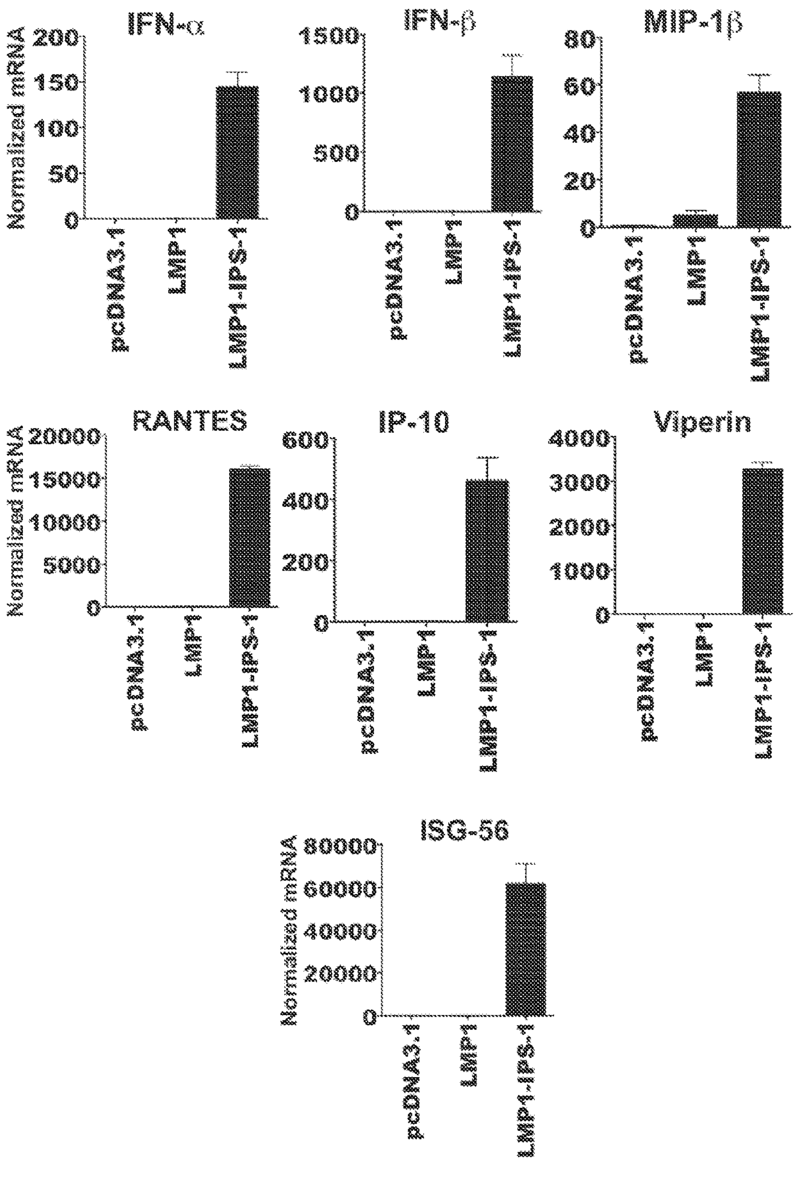
FIG. 14 is a series of graphs of results showing that LMP1-IPS1 induces type I interferons as well as interferon stimulated genes implicated in the inhibition of HIV-1 replication.

Referring to FIG. 13, LMP1-IPS-1 prevents HIV replication in primary CD4+ T cells. Primary human CD4+ T cells from a healthy donor were infected with HIV-BaL at MOI of 0.1 and 1, cultured in a transwell assay with 293 cells that had been previously transfected with either empty plasmid (pcDNA3.1) or LMP1-IPS1. Again, LMP1-IPS1 was able to inhibit HIV-1 replication in CD4+ T cells via one or more soluble factors. * $p<0.001$ Referring to FIG. 14**, LMP1-IPS1 induces type I Interferons as well as interferon stimulated genes (ISGs). IPS-1 is involved in the induction of type I interferon, which is known to inhibit HIV-1 replication at high concentrations. Interferon alpha and beta mRNA levels were evaluated by qPCR. We also evaluated genes involved in CCR5 blockade (MIP-1b, RANTES, IP-10) and interferon stimulated genes that are known to restrict HIV and other viruses (Viperin, ISG56). All of these genes were upregulated in 293T cells transfected with plasmid DNA encoding LMP1-IPS1, but not plasmid DNA for LMP1 or empty plasmid control (pcDNA3.1).

Figure 15:
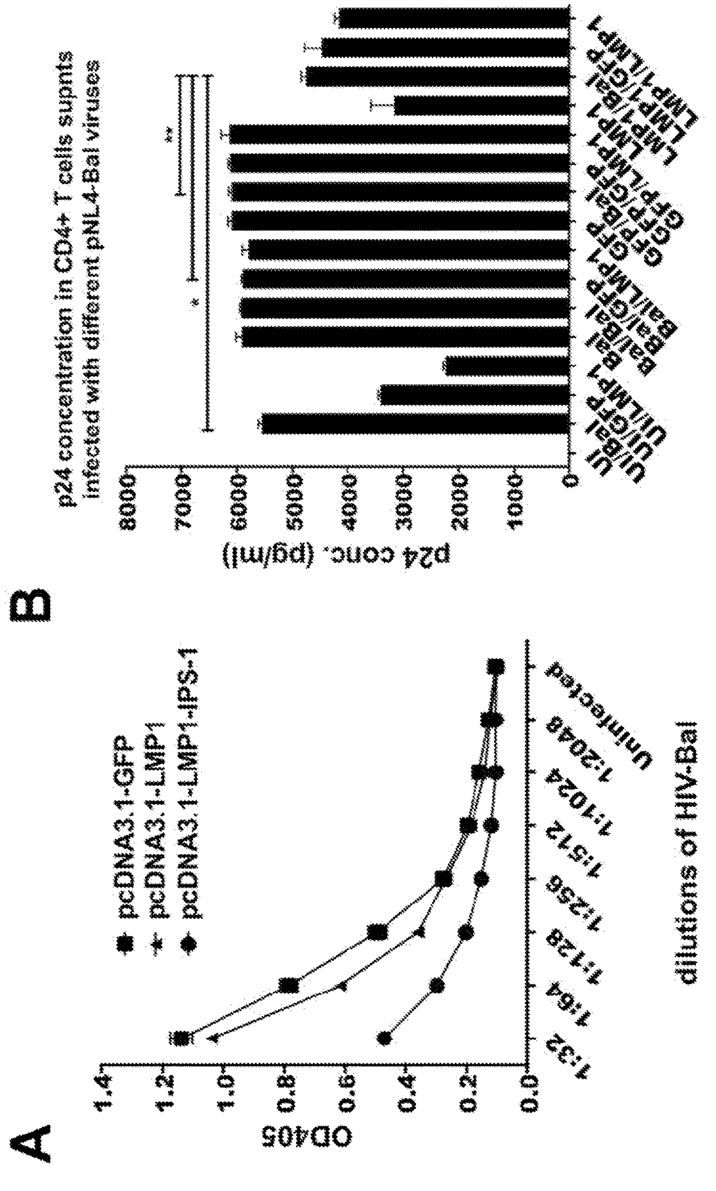
FIG. 15 is a pair of graphs of results showing that full length LMP1 and a LMP1-IPS-1 fusion protein are able to protect cells from HIV-1 infection, with superior protection by LMP1-IPS-1.

Referring to FIG. 15, LMP1 and LMP1-IPS-1 fusion protein are able to protect cells from HIV-1 infection. In FIG. 15(A), TZM-bl cells, a HeLa cell line expressing CD4, CCR5, and a HIV-1 promoter β-galactosidase reporter gene, were transfected with plasmids expressing either EGFP (control), LMP1, or LMP1-IPS-1. Cells were then infected with serial dilutions of HIV-1 BaL strain virus. The level of HIV-1 infection was measured by p24 ELISA assay using β-galactosidase and OD405. Transfection with DNA for the LMP1-IPS-1 fusion protein was able to protect TZM-bl cells from infection, providing evidence that LMP1-IPS-1 is able to induce cytokines and/or other innate antiviral mechanisms in this cell line. In FIG. 15(B), primary human CD4+ T cells were cultured with HIV-1 recombinant virus expressing GFP or LMP1 (as described by us in S. Gupta et al., Journal of Leukocyte Biology 90:389-398, 2011). Replication as measured by p24 ELISA on day 4 was significantly reduced for HIV-LMP1 compared to BaL (wildtype) and GFP viral constructs. Other cells were infected with one virus for 2 days, washed, and then superinfected with a second viral construct. Initial infection with HIV-LMP1 was able to significantly reduce replication following BaL or GFP viral construct superinfection. These data suggest that LMP1 is able to induce an innate immune response capable of protecting primary CD4+ T cells from HIV-1 infection. Similar data was observed with unfractionated PBMC.

Figure 16:
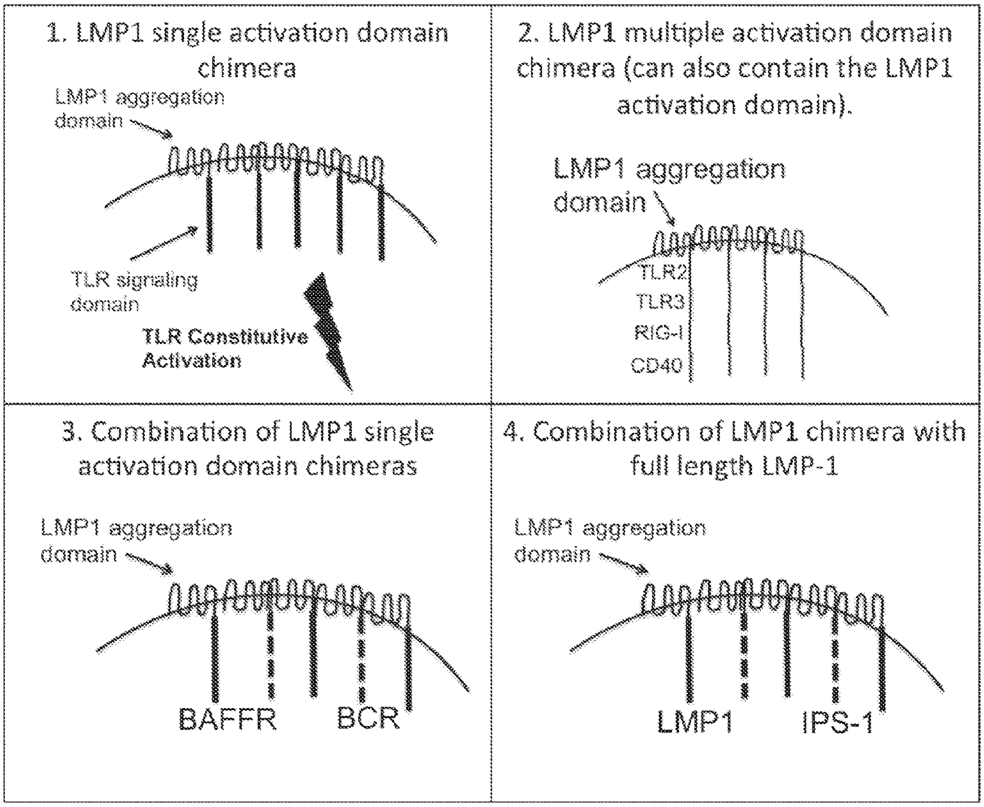
FIG. 16 is a schematic illustration of examples of different LMP1 fusion protein construct formulations.

Referring to FIG. 16, four examples of formulations of LMP1 fusion proteins are described. Example 1 is the fusion of the LMP1 transmembrane and aggregation domain to a single TLR signaling domain, TNF receptor, cytokine receptor, or adapter protein. Example 2 is the direct fusion of LMP1 transmembrane domain with two or more signaling domains, including the use of the LMP1 signaling domain itself. Example 3 describes the co-expression of two or more LMP1 fusion proteins each encoding a different signaling domain. The example is given of LMP1-BAFFR fusion protein combined with an LMP1 fusion to the B cell receptor signaling domain (LMP1-BCR). Example 4 describes the combination of full-length LMP1 with LMP1 fusion proteins, for example LMP1+LMP1-IPS-1.

Conclusions

LMP1-IPS-1 is a potent inducer of NF-κB and IFN-β responses. LMP1-IPS-1 causes activation and maturation of the RAW 264.7 macrophage cell line by increasing expression of surface markers such as CD80, CD86, CD40, IA/IE and CCR7. LMP1-IPS-1 induces very high levels of IL-6 from transfected RAW 264.7 cells. LMP1-IPS-1 prevents the replication of both HIV and VSV-G pseudotyped scSIV in TZM-bl cells as well as primary CD4+ T cells both in cis and in trans. LMP1-IPS-1 induces type 1 interferons, interferons stimulated genes (ISGs) and chemokines genes implicated in inhibition of HIV replication. In conclusion, these studies suggest that LMP1-IPS-1 is immunostimulatory and induces a strong anti-viral immune response for the prevention of HIV-1 infection of primary CD4+ T cells.

Example 3

DNA and amino acid sequences for LMP1 fusion constructs: LMP1 fusions to TLR, TNFSFR or other immune activating receptors.

SEQ ID NO:1 is Epstein Barr Virus latent membrane protein 1 (without the cytoplasmic domain) fused to the cytoplasmic domain of murine TLR7.

LMP1-muTLR7

Italicized/bolded sequence: LMP1 sequence (Transmembrane Domain)

Non-italicized/bolded sequence: Murine TLR7 sequence (Cytoplasmic Domain)

(SEQ ID NO: 1)

*ATGGAACACGACCTTGAGAGGGGCCCACCGGGCCCGCGACGGCCC*

*CCTCGAGGACCCCCCCTCTCCTCTTCCCTAGGCCTTGCTCTCCTT*

*CTCCTCCTCTTGGCGCTACTGTTTTGGCTGTACATCGTTATGAGT*

*GACTGGACTGGAGGAGCCCTCCTTGTCCTCTATTCCTTTGCTCTC*

*ATGCTTATAATTATAATTTTGATCATCTTTATCTTCAGAAGAGAC*

*CTTCTCTGTCCACTTGGAGCCCTTTGTATACTCCTACTGATGATC*

*ACCCTCCTGCTCATCGCTCTCTGGAATTTGCACGGACAGGCATTG*

*TTCCTTGGAATTGTGCTGTTCATCTTCGGGTGCTTACTTGTCTTA*

*GGTATCTGGATCTACTTATTGGAGATGCTCTGGCGACTTGGTGCC*

*ACCATCTGGCAGCTTTTGGCCTTCTTCCTAGCCTTCTTCCTAGAC*

*CTCATCCTGCTCATTATTGCTCTCTATCTACAACAAAACTGGTGG*

*ACTCTATTGGTTGATCTCCTTTGGCTCCTCCTGTTTCTGGCGATT*

*TTAATCTGGATGTATTACCATGGACAACGA*ACAACAAGTCACCTC

TTTTTCTGGGATATGTGGTACATTTATTATTTTTGGAAAGCAAAG

ATAAAGGGGTATCAGCATCTGCAATCCATGGAGTCTTGTTATGAT

GCTTTTATTGTGTATGACACTAAAAACTCAGCTGTGACAGAATGG

GTTTTGCAGGAGCTGGTGGCAAAATTGGAAGATCCAAGAGAAAAA

CACTTCAATTTGTGTCTAGAAGAAAGAGACTGGCTACCAGGACAG

CCAGTTCTAGAAAACCTTTCCCAGAGCATACAGCTCAGCAAAAAG

ACAGTGTTTGTGATGACACAGAAATATGCTAAGACTGAGAGTTTT

AAGATGGCATTTTATTTGTCTCATCAGAGGCTCCTGGATGAAAAA

-continued

GTGGATGTGATTATCTTGATATTCTTGGAAAAGCCTCTTCAGAAG

TCTAAGTTTCTTCAGCTCAGGAAGAGACTCTGCAGGAGCTCTGTC

CTTGAGTGGCCTGCAAATCCACAGGCTCACCCATACTTCTGGCAG

TGCCTGAAAAATGCCCTGACCACAGACAATCATGTGGCTTATAGT

CAAATGTTCAAGGAAACAGTCTAG

SEQ ID NO:2 is Epstein Barr Virus latent membrane protein 1 (without the cytoplasmic domain) fused to the cytoplasmic domain of murine TLR7.

Protein:

(SEQ ID NO: 2)

MEHDLERGPPGPRRPPRGPPLSSSLGLALLLLLLALLFWLYIVMSDWTGG

ALLVLYSFALMLIIIILIIFIFRRDLLCPLGALCILLLMITLLLIALWNL

HGQALFLGIVLFIFGCLLVLGIWIYLLEMLWRLGATIWQLLAFFLAFFLD

LILLIIALYLQQNWWTLLVDLLWLLLFLAILIWMYYHGQRTTSHLFFWDM

WYIYYFWKAKIKGYQHLQSMESCYDAFIVYDTKNSAVTEWVLQELVAKLE

DPREKHFNLCLEERDWLPGQPVLENLSQSIQLSKKTVFVMTQKYAKTESF

KMAFYLSHQRLLDEKVDVIILIFLEKPLQKSKFLQLRKRLCRSSVLEWPA

NPQAHPYFWQCLKNALTTDNHVAYSQMFKETV

SEQ ID NO:3 is Epstein Barr Virus latent membrane protein 1 (without the cytoplasmic domain) fused to the cytoplasmic domain of murine BAFF receptor.

LMP1-muBAFFR

Italicized/bolded sequence: LMP1 sequence (Transmembrane Domain)

Non-italicized/bolded sequence: Murine BAFFR (Cytoplasmic Domain)

(SEQ ID NO: 3)

*ATGGAACACGACCTTGAGAGGGGCCCACCGGGCCCGCGACGGCCC*

*CCTCGAGGACCCCCCCTCTCCTCTTCCATAGGCCTTGCTCTCCTT*

*CTCCTGCTCTTGGCGCTACTGTTTTGGCTGTACATCATTATGAGT*

*AACTGGACTGGAGGAGCCCTCCTTGTCCTCTATGCCTTTGCTCTC*

*ATGCTTGTGATTATCATTTTGATCATCTTTATCTTCAGAAGAGAC*

*CTTCTCTGTCCACTTGGAGCCCTTTGTCTACTCCTACTGATGATC*

*ACCCTCCTGCTCATCGCTCTCTGGAATTTGCACGGACAGGCATTG*

*TACCTTGGAATTGTGCTGTTCATCTTCGGGTGCTTACTTGTCTTA*

*GGTCTCTGGATCTACTTATTGGAGATTCTCTGGCGACTTGGTGCC*

*ACCATCTGGCAGCTTTTGGCCTTCTTCCTAGCCTTCTTCCTAGAC*

*ATCATCCTGCTCATTATTGCTCTCTATCTACAACAAAACTGGTGG*

*ACTCTATTGGTTGATCTCCTTTGGCTCCTCCTGTTTCTGGCGATT*

-continued

*TTAATCTGGATGTATTACCATGGACAACGA*AGTCTGGTGAGCTGG

AGGTGGCGTCAACAGCTCAGGACGGCCTCCCCAGACACTTCAGAA

GGAGTCCAGCAAGAGTCCCTGGAAAATGTCTTTGTACCCTCCTCA

GAAACCCCTCATGCCTCAGCTCCTACCTGGCCTCCGCTCAAAGAA

GATGCAGACAGCGCCCTGCCACGCCACAGCGTCCCGGTGCCCGCC

ACAGAACTGGGCTCCACCGAGCTGGTGACCACCAAGACAGCTGGC

CCAGAGCAATAG

SEQ ID NO:4 is Epstein Barr Virus latent membrane protein 1 (without the cytoplasmic domain) fused to the cytoplasmic domain of murine BAFF receptor.

Protein:

(SEQ ID NO: 4)

MEHDLERGPPGPRRPPRGPPLSSSIGLALLLLLLALLFWLYIIMSNWTGG

ALLVLYAFALMLVIIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRSLVSWRWRQQ

LRTASPDTSEGVQQESLENVFVPSSETPHASAPTWPPLKEDADSALPRHS

VPVPATELGSTELVTTKTAGPEQ

SEQ ID NO:5 is Epstein Barr Virus latent membrane protein 1 (without the cytoplasmic domain) fused to the CARD domain of murine RIG-I.

LMP1-muRIG1

Italicized/bolded sequence: LMP1 sequence (Transmembrane Domain)

Non-italicized/bolded sequence: Mouse RIG1 (CARD domain)

(SEQ ID NO: 5)

*ATGGAACACGACCTTGAGAGGGGCCCACCGGGCCCGCGACGGCCC*

*CCTCGAGGACCCCCCCTCTCCTCTTCCATAGGCCTTGCTCTCCTT*

*CTCCTGCTCTTGGCGCTACTGTTTTGGCTGTACATCATTATGAGT*

*AACTGGACTGGAGGAGCCCTCCTTGTCCTCTATGCCTTTGCTCTC*

*ATGCTTGTGATTATCATTTTGATCATCTTTATCTTCAGAAGAGAC*

*CTTCTCTGTCCACTTGGAGCCCTTTGTCTACTCCTACTGATGATC*

*ACCCTCCTGCTCATCGCTCTCTGGAATTTGCACGGACAGGCATTG*

*TACCTTGGAATTGTGCTGTTCATCTTCGGGTGCTTACTTGTCTTA*

*GGTCTCTGGATCTACTTATTGGAGATTCTCTGGCGACTTGGTGCC*

-continued

*ACCATCTGGCAGCTTTTGGCCTTCTTCCTAGCCTTCTTCCTAGAC*

*ATCATCCTGCTCATTATTGCTCTCTATCTACAACAAAACTGGTGG*

*ACTCTATTGGTTGATCTCCTTTGGCTCCTCCTGTTTCTGGCGATT*

*TTAATCTGGATGTATTACCATGGACAACGA*ATGACCGCGGCGCAG

CGGCAGAATCTGCAAGCATTCAGAGACTATATCAAGAAGATTCTG

GACCCCACCTACATCCTCAGCTACATGAGTTCCTGGCTCGAGGAT

GAGGAGGTGCAGTACATTCAGGCTGAGAAGAACAACAAGGGCCCA

ATGGAAGCTGCCTCACTCTTCCTCCAGTACCTGTTGAAGCTGCAG

TCAGAGGGCTGGTTCCAGGCCTTTTTGGATGCCCTGTACCATGCA

GGTTACTGTGGACTTTGTGAAGCCATCGAAAGTTGGGACTTTCAA

AAAATTGAAAAGTTAGAGGAACACAGATTACTTTTAAGACGTTTA

GAACCAGAATTTAAGGCCACAGTTGATCCAAATGATATCCTTTCT

GAACTATCCGAATGTTTGATTAATCAGGAATGTGAAGAAATCAGA

CAGATCCGAGACACTAAAGGGAGAATGGCAGGTGCGGAGAAGATG

GCCGAATGTCTTATCAGATCCGACAAGGAAAACTGGCCAAAGGTC

TTGCAATAG

SEQ ID NO: 6 is Epstein Barr Virus latent membrane protein 1 (without the cytoplasmic domain) fused to the CARD domain of murine RIG-I Protein:

(SEQ ID NO: 6)

MEHDLERGPPGPRRPPRGPPLSSSIGLALLLLLLALLFWLYIIMSNWTGGA

LLVLYAFALMLVIIILIIFIFRRDLLCPLGALCLLLLMITLLLIALWNLHG

QALYLGIVLFIFGCLLVLGLWIYLLEILWRLGATIWQLLAFFLAFFLDIIL

LIIALYLQQNWWTLLVDLLWLLLFLAILIWMYYHGQRMTAAQRQNLQAFRD

YIKKILDPTYILSYMSSWLEDEEVQYIQAEKNNKGPMEAASLFLQYLLKLQ

SEGWFQAFLDALYHAGYCGLCEAIESWDFQKIEKLEEHRLLLRRLEPEFKA

TVDPNDILSELSECLINQECEEIRQIRDTKGRMAGAEKMAECLIRSDKENW

PKVLQ

Example 4

DNA and amino acid sequences for LMP1 fusion constructs: LMP1 fusions to immune activation adapter proteins.

SEQ ID NO:7 is Epstein Barr Virus latent membrane protein 1 (without the cytoplasmic domain) fused to human MyD88.

LMP1-huMyD88

Italicized/bolded sequence: LMP1 sequence (Transmembrane Domain)

Non-italicized/bolded sequence: human MyD88

(SEQ ID NO: 7)

*ATGGAACACGACCTTGAGAGGGGCCCACCGGGCCCGCGACGGCCC*

*CCTCGAGGACCCCCCCTCTCCTCTTCCATAGGCCTTGCTCTCCTT*

*CTCCTGCTCTTGGCGCTACTGTTTTGGCTGTACATCATTATGAGT*

*AACTGGACTGGAGGAGCCCTCCTTGTCCTCTATGCCTTTGCTCTC*

*ATGCTTGTGATTATCATTTTGATCATCTTTATCTTCAGAAGAGAC*

*CTTCTCTGTCCACTTGGAGCCCTTTGTCTACTCCTACTGATGATC*

*ACCCTCCTGCTCATCGCTCTCTGGAATTTGCACGGACAGGCATTG*

*TACCTTGGAATTGTGCTGTTCATCTTCGGGTGCTTACTTGTCTTA*

*GGTCTCTGGATCTACTTATTGGAGATTCTCTGGCGACTTGGTGCC*

*ACCATCTGGCAGCTTTTGGCCTTCTTCCTAGCCTTCTTCCTAGAC*

*ATCATCCTGCTCATTATTGCTCTCTATCTACAACAAAACTGGTGG*

*ACTCTATTGGTTGATCTCCTTTGGCTCCTCCTGTTTCTGGCGATT*

*TTAATCTGGATGTATTACCATGGACAACGA*ATGGCTGCAGGAGGT

CCCGGCGCGGGGTCTGCGGCCCCGGTCTCCTCCACATCCTCCCTT

CCCCTGGCTGCTCTCAACATGCGAGTGCGGCGCCGCCTGTCTCTG

TTCTTGAACGTGCGGACACAGGTGGCGGCCGACTGGACCGCGCTG

GCGGAGGAGATGGACTTTGAGTACTTGGAGATCCGGCAACTGGAG

ACACAAGCGGACCCCACTGGCAGGCTGCTGGACGCCTGGCAGGGA

CGCCCTGGCGCCTCTGTAGGCCGACTGCTCGAGCTGCTTACCAAG

CTGGGCCGCGACGACGTGCTGCTGGAGCTGGGACCCAGCATTGAG

GAGGATTGCCAAAAGTATATCTTGAAGCAGCAGCAGGAGGAGGCT

GAGAAGCCTTTACAGGTGGCCGCTGTAGACAGCAGTGTCCCACGG

ACAGCAGAGCTGGCGGGCATCACCACACTTGATGACCCCCTGGGG

CATATGCCTGAGCGTTTCGATGCCTTCATCTGCTATTGCCCCAGC

GACATCCAGTTTGTGCAGGAGATGATCCGGCAACTGGAACAGACA

AACTATCGACTGAAGTTGTGTGTGTCTGACCGCGATGTCCTGCCT

GGCACCTGTGTCTGGTCTATTGCTAGTGAGCTCATCGAAAAGAGG

TGCCGCCGGATGGTGGTGGTTGTCTCTGATGATTACCTGCAGAGC

AAGGAATGTGACTTCCAGACCAAATTTGCACTCAGCCTCTCTCCA

GGTGCCCATCAGAAGCGACTGATCCCCATCAAGTACAAGGCAATG

AAGAAAGAGTTCCCCAGCATCCTGAGGTTCATCACTGTCTGCGAC

TACACCAACCCCTGCACCAAATCTTGGTTCTGGACTCGCCTTGCC

AAGGCCTTGTCCCTGTGA

SEQ ID NO:8 is Epstein Barr Virus latent membrane protein 1 (without the cytoplasmic domain) fused to human MyD88.

Protein:

(SEQ ID NO: 8)

MEHDLERGPPGPRRPPRGPPLSSSIGLALLLLLLALLFWLYIIMSNWTGGA

LLVLYAFALMLVIIILIIFIFRRDLLCPLGALCLLLLMITLLLIALWNLHG

QALYLGIVLFIFGCLLVLGLWIYLLEILWRLGATIWQLLAFFLAFFLDIIL

LIIALYLQQNWWTLLVDLLWLLLFLAILIWMYYHGQRMAAGGPGAGSAAPV

SSTSSLPLAALNMRVRRRLSLFLNVRTQVAADWTALAEEMDFEYLEIRQLE

TQADPTGRLLDAWQGRPGASVGRLLELLTKLGRDDVLLELGPSIEEDCQKY

ILKQQQEEAEKPLQVAAVDSSVPRTAELAGITTLDDPLGHMPERFDAFICY

CPSDIQFVQEMIRQLEQTNYRLKLCVSDRDVLPGTCVWSIASELIEKRCRR

MVVVVSDDYLQSKECDFQTKFALSLSPGAHQKRLIPIKYKAMKKEFPSILR

FITVCDYTNPCTKSWFWTRLAKALSL

SEQ ID NO:9 is Epstein Barr Virus latent membrane protein 1 (without the cytoplasmic domain) fused to murine IPS-1.

LMP1-muIPS-1

Italicized/bolded sequence: LMP1 sequence (Transmembrane Domain)

Non-italicized/bolded sequence: Murine IPS-1

(SEQ ID NO: 9)

*ATGGAACACGACCTTGAGAGGGGCCCACCGGGCCCGCGACGGCCC*

*CCTCGAGGACCCCCCCTCTCCTCTTCCATAGGCCTTGCTCTCCTT*

*CTCCTGCTCTTGGCGCTACTGTTTTGGCTGTACATCATTATGAGT*

*AACTGGACTGGAGGAGCCCTCCTTGTCCTCTATGCCTTTGCTCTC*

*ATGCTTGTGATTATCATTTTGATCATCTTTATCTTCAGAAGAGAC*

*CTTCTCTGTCCACTTGGAGCCCTTTGTCTACTCCTACTGATGATC*

*ACCCTCCTGCTCATCGCTCTCTGGAATTTGCACGGACAGGCATTG*

*TACCTTGGAATTGTGCTGTTCATCTTCGGGTGCTTACTTGTCTTA*

*GGTCTCTGGATCTACTTATTGGAGATTCTCTGGCGACTTGGTGCC*

*ACCATCTGGCAGCTTTTGGCCTTCTTCCTAGCCTTCTTCCTAGAC*

*ATCATCCTGCTCATTATTGCTCTCTATCTACAACAAAACTGGTGG*

*ACTCTATTGGTTGATCTCCTTTGGCTCCTCCTGTTTCTGGCGATT*

*TTAATCTGGATGTATTACCATGGACAACGA*ATGACATTTGCTGAG

GACAAGACCTATAAGTATATCCGAGACAACCACAGCAAGTTTTGC

-continued

TGTGTTGACGTTCTGGAGATCCTGCCTTACCTGTCCTGCCTCACA

GCTAGTGACCAGGATCGACTGCGGGCTTCCTACAGGCAGATCGGG

AACCGGGACACACTCTGGGGACTCTTCAATAATCTCCAGCGCCGG

CCTGGCTGGGTGGAGGTCTTCATCCGGGCACTGCAGATCTGTGAG

CTGCCTGGGCTGGCTGATCAAGTGACTCGAGTTTATCAGAGCTAC

CTGCCTCCGGGGACCTCACTCCGCTCCCTAGAGCCACTGCAGTTA

CCAGACTTTCCTGCTGCGGTTTCTGGACCCTCTGCATTTGCGCCA

GGTCACAACATCCCTGACCATGGCTTACGAGAGACACCAAGTTGC

CCCAAGCCTGTCCAGGACACCCAGCCACCAGAGTCCCCAGTAGAG

AATTCAGAGCAACTCCTCCAGACCAACTCCGGGGCCGTCGCGAGG

ATGTCTGGTGGCTCTTTGATACCCTCTCCTAACCAGCAGGCTCTC

AGCCCTCAGCCCTCCAGAGAGCATCAAGAGCAAGAACCAGAACTG

GGTGGCGCCCACGCAGCAAATGTTGCCTCTGTTCCCATAGCAACC

TATGGACCTGTGTCTCCAACCGTTTCCTTCCAGCCCCTTCCACGT

ACTGCCCTGAGGACAAACCTCTTGTCTGGGGTCACAGTATCAGCC

CTATCTGCTGATACCTCTTTGTCCTCCTCGTCCACTGGATCAGCT

TTTGCAAAGGGAGCTGGTGACCAGGCCAAAGCTGCCACCTGTTTC

AGTACTACACTCACCAATTCTGTGACTACCAGCTCAGTGCCTTCT

CCCAGATTGGTCCCAGTAAAAACCATGTCTTCCAAGTTGCCCCTC

AGTTCAAAGTCCACTGCTGCGATGACGTCTACTGTGCTCACCAAT

ACAGCGCCATCAAAATTACCCAGCAACTCAGTGTATGCGGGCACA

GTGCCATCCAGAGTGCCTGCTAGTGTGGCCAAAGCACCTGCCAAC

ACAATACCACCTGAGAGGAACAGCAAGCAAGCCAAGGAGACCCCG

GAGGGTCCAGCAACCAAAGTCACCACTGGAGGCAACCAGACTGGA

CCAAATAGCAGTATCAGGAGCTTGCACTCTGGACCAGAGATGAGC

AAGCCAGGTGTGCTGGTATCCCAGTTGGACGAGCCATTCTCAGCC

TGCTCTGTGGACCTTGCCATTAGCCCTAGCAGCTCCTTGGTCTCA

GAACCCAACCATGGTCCAGAGGAGAATGAGTATTCGTCCTTTAGA

ATCCAGGTAGACGAAAGCCCCAGTGCTGATCTATTAGGAAGCCCT

GAGCCACTAGCCACCCAGCAGCCCCAAGAAGAGGAAGAACATTGT

GCCAGTTCAATGCCCTGGGCTAAGTGGCTTGGGGCCACCAGTGCA

CTCTTGGCTGTATTCCTGGCAGTGATGCTGTACCGTAGTAGGCGC

CTGGCCCAGTGA

SEQ ID NO:10 is Epstein Barr Virus latent membrane protein 1 (without the cytoplasmic domain) fused to murine IPS-1.

Protein:

(SEQ ID NO: 10)

MEHDLERGPPGPRRPPRGPPLSSSIGLALLLLLLALLFWLYIIMSNWTGGA

LLVLYAFALMLVIIILIIFIFRRDLLCPLGALCLLLLMITLLLIALWNLHG

QALYLGIVLFIFGCLLVLGLWIYLLEILWRLGATIVVQLLAFFLAFFLDII

LLIIALYLQQNWVVTLLVDLLWLLLFLAILIVVMYYHGQRMTFAEDKTYKY

RDNHSKFCCVDVLEILPYLSCLTASDQDRLRASYRQIGNRDTLWGLFNNLQ

RRPGWVEVFIRALQICELPGLADQVTRVYQSYLPPGTSLRSLEPLQLPDFP

AAVSGPSAFAPGHNIPDHGLRETPSCPKPVQDTQPPESPVENSEQLLQTNS

GAVARMSGGSLIPSPNQQALSPQPSREHQEQEPELGGAHAANVASVPIATY

GPVSPTVSFQPLPRTALRTNLLSGVTVSALSADTSLSSSSTGSAFAKGAGD

QAKAATCFSTTLTNSVTTSSVPSPRLVPVKTMSSKLPLSSKSTAAMTSTVL

TNTAPSKLPSNSVYAGTVPSRVPASVAKAPANTIPPERNSKQAKETPEGPA

TKVTTGGNQTGPNSSIRSLHSGPEMSKPGVLVSQLDEPFSACSVDLAISPS

SSLVSEPNHGPEENEYSSFRIQVDESPSADLLGSPEPLATQQPQEEEEHCA

SSMPWAKWLGATSALLAVFLAVMLYRSRRLAQ

SEQ ID NO: 11 is Epstein Barr Virus latent membrane protein 1 (without the cytoplasmic domain) fused to the cytoplasmic domain of human CD3 zeta chain.

LMP1-huCD3 Zeta Chain

Italicized/bolded sequence: LMP1 sequence (Transmembrane Domain)

Non-italicized/bolded sequence: huCD3 zeta chain (Cytoplasmic Domain)

(SEQ ID NO: 11)

*ATGGAACACGACCTTGAGAGGGGCCCACCGGGCCCGCGACGGCCC*

*CCTCGAGGACCCCCCCTCTCCTCTTCCCTAGGCCTTGCTCTCCTT*

*CTCCTCCTCTTGGCGCTACTGTTTTGGCTGTACATCGTTATGAGT*

*GACTGGACTGGAGGAGCCCTCCTTGTCCTCTATTCCTTTGCTCTC*

*ATGCTTATAATTATAATTTTGATCATCTTTATCTTCAGAAGAGAC*

*CTTCTCTGTCCACTTGGAGCCCTTTGTATACTCCTACTGATGATC*

*ACCCTCCTGCTCATCGCTCTCTGGAATTTGCACGGACAGGCATTG*

*TTCCTTGGAATTGTGCTGTTCATCTTCGGGTGCTTACTTGTCTTA*

*GGTATCTGGATCTACTTATTGGAGATGCTCTGGCGACTTGGTGCC*

*ACCATCTGGCAGCTTTTGGCCTTCTTCCTAGCCTTCTTCCTAGAC*

*CTCATCCTGCTCATTATTGCTCTCTATCTACAACAAAACTGGTGG*

*ACTCTATTGGTTGATCTCCTTTGGCTCCTCCTGTTTCTGGCGATT*

*TTAATCTGGATGTATTACCATGGACAACGA*AGAGTGAAGTTCAGC

AGGAGCGCAGACGCCCCCGCGTACCAGCAGGGCCAGAACCAGCTC

TATAACGAGCTCAATCTAGGACGAAGAGAGGAGTACGATGTTTTG

GACAAGAGACGTGGCCGGGACCCTGAGATGGGGGGAAAGCCGCAG

AGAAGGAAGAACCCTCAGGAAGGCCTGTACAATGAACTGCAGAAA

GATAAGATGGCGGAGGCCTACAGTGAGATTGGGATGAAAGGCGAG

CGCCGGAGGGGCAAGGGGCACGATGGCCTTTACCAGGGTCTCAGT

ACAGCCACCAAGGACACCTACGACGCCCTTCACATGCAGGCCCTG

CCCCCTCGCTAA

SEQ ID NO:12 is Epstein Barr Virus latent membrane protein 1 (without the cytoplasmic domain) fused to the cytoplasmic domain of human CD3 zeta chain.
Protein:

(SEQ ID NO: 12)

MEHDLERGPPGPRRPPRGPPLSSSLGLALLLLLLALLFWLYIVMSDWTGGA

LLVLYSFALMLIIIILIIFIFRRDLLCPLGALCILLLMITLLLIALWNLHG

QALFLGIVLFIFGCLLVLGIWIYLLEMLWRLGATIWQLLAFFLAFFLDLIL

LIIALYLQQNWWTLLVDLLWLLLFLAILIWMYYHGQRRVKFSRSADAPAYQ

QGQNQLYNELNLGRREEYDVLDKRRGRDPEMGGKPQRRKNPQEGLYNELQK

DKMAEAYSEIGMKGERRRGKGHDGLYQGLSTATKDTYDALHMQALPPR

SEQ ID NO:13 is Influenza NP protein co-expressed by use of an IRES sequence with Epstein Barr Virus latent membrane protein 1 (without the cytoplasmic domain) fused to murine MyD88 and the cytoplasmic domain of murine CD40 as a single 3-protein chimera.

NP-IRES-LMP1-muMyD88-muCD40

Italicized sequence: Influenza NP sequence
Non-italicized sequence: IRES

Italicized/bolded sequence: LMP1 sequence (Transmembrane Domain)

Non-italicized/bolded sequence: Murine MyD88 sequence

Underlined sequence: Linker

Bolded sequence: Murine CD40 sequence (cytoplasmic domain)

(SEQ ID NO: 13)

*ATGGCGTCTCAAGGCACCAAACGATCTTACGAACAGATGGAGACT*

*GATGGAGAACGCCAGAATGCCACTGAAATCAGAGCATCCGTCGGA*

*AAAATGATTGGTGGAATTGGACGATTCTACATCCAAATGTGCACC*

*GAACTCAAACTCAGTGATTATGAGGGACGGTTGATCCAAAACAGC*

*TTAACAATAGAGAGAATGGTGCTCTCTGCTTTTGACGAAAGGAGA*

*AATAAATACCTTGAAGAACATCCCAGTGCGGGGAAAGATCCTAAG*

*AAAACTGGAGGACCTATATACAGGAGAGTAAACGGAAAGTGGATG*

*AGAGAACTCATCCTTTATGACAAAGAAGAAATAAGGCGAATCTGG*

*CGCCAAGCTAATAATGGTGACGATGCAACGGCTGGTCTGACTCAC*

*ATGATGATCTGGCATTCCAATTTGAATGATGCAACTTATCAGAGG*

*ACAAGAGCTCTTGTTCGCACCGGAATGGATCCCAGGATGTGCTCT*

*CTGATGCAAGGTTCAACTCTCCCTAGGAGGTCTGGAGCCGCAGGT*

*GCTGCAGTCAAAGGAGTTGGAACAATGGTGATGGAATTGGTCAGA*

*ATGATCAAACGTGGGATCAATGATCGGAACTTCTGGAGGGGTGAG*

*AATGGACGAAAAACAAGAATTGCTTATGAAAGAATGTGCAACATT*

*CTCAAAGGGAAATTTCAAACTGCTGCACAAAAAGCAATGATGGAT*

*CAAGTGAGAGAGAGCCGGAACCCAGGGAATGCTGAGTTCGAAGAT*

*CTCACTTTTCTAGCACGGTCTGCACTCATATTGAGAGGGTCGGTT*

*GCTCACAAGTCCTGCCTGCCTGCCTGTGTGTATGGACCTGCCGTA*

*GCCAGTGGGTACGACTTTGAAAGGGAGGGATACTCTCTAGTCGGA*

*ATAGACCCTTTCAGACTGCTTCAAAACAGCCAAGTGTACAGCCTA*

*ATCAGACCAAATGAGAATCCAGCACACAAGAGTCAACTGGTGTGG*

*ATGGCATGCCATTCTGCCGCATTTGAAGATCTAAGAGTATTAAGC*

*TTCATCAAAGGGACGAAGGTGCTCCCAAGAGGGAAGCTTTCCACT*

*AGAGGAGTTCAAATTGCTTCCAATGAAAATATGGAGACTATGGAA*

*TCAAGTACACTTGAACTGAGAAGCAGGTACTGGGCCATAAGGACC*

*AGAAGTGGAGGAAACACCAATCAACAGAGGGCATCTGCGGGCCAA*

*ATCAGCATACAACCTACGTTCTCAGTACAGAGAAATCTCCCTTTT*

*GACAGAACAACCATTATGGCAGCATTCAATGGGAATACAGAGGGG*

-continued

AGAACATCTGACATGAGGACCGAAATCATAAGGATGATGGAAAGT

GCAAGACCAGAAGATGTGTCTTTCCAGGGGCGGGGAGTCTTCGAG

CTCTCGGACGAAAAGGCAGCGAGCCCGATCGTGCCTTCCTTTGAC

ATGAGTAATGAAGGATCTTATTTCTTCGGAGACAATGCAGAGGAG

TACGACAATTAAGCCCCTCTCCCTCCCCCCCCCCTAACGTTACTG

GCCGAAGCCGCTTGGAATAAGGCCGGTGTGTGTTTGTCTATATGT

GATTTTCCACCATATTGCCGTCTTTTGGCAATGTGAGGGCCCGGA

AACCTGGCCCTGTCTTCTTGACGAGCATTCCTAGGGGTCTTTCCC

CTCTCGCCAAAGGAATGCAAGGTCTGTTGAATGTCGTGAAGGAAG

CAGTTCCTCTGGAAGCTTCTTGAAGACAAACAACGTCTGTAGCGA

CCCTTTGCAGGCAGCGGAACCCCCCACCTGGCGACAGGTGCCTCT

GCGGCCAAAAGCCACGTGTATAAGATACACCTGCAAAGGCGGCAC

AACCCCAGTGCCACGTTGTGAGTTGGATAGTTGTGGAAAGAGTCA

AATGGCTCTCCTCAAGCGTAGTCAACAAGGGGCTGAAGGATGCCC

AGAAGGTACCCCATTGTATGGGAATCTGATCTGGGGCCTCGGTGC

ACATGCTTTACATGTGTTTAGTCGAGGTTAAAAAAGCTCTAGGCC

CCCCGAACCACGGGGACGTGGTTTTCCTTTGAAAAACACGATGAT

AAGCTTGCCACAAATGGAACACGACCTTGAGAGGGGCCCACCGGG

CCCGCGACGGCCCCCTCGAGGACCCCCCCTCTCCTCTTCCCTAGG

CCTTGCTCTCCTTCTCCTCCTCTTGGCGCTACTGTTTTGGCTGTA

CATCGTTATGAGTGACTGGACTGGAGGAGCCCTCCTTGTCCTCTA

TTCCTTTGCTCTCATGCTTATAATTATAATTTTGATCATCTTTAT

CTTCAGAAGAGACCTTCTCTGTCCACTTGGAGCCCTTTGTATACT

CCTACTGATGATCACCCTCCTGCTCATCGCTCTCTGGAATTTGCA

CGGACAGGCATTGTTCCTTGGAATTGTGCTGTTCATCTTCGGGTG

CTTACTTGTCTTAGGTATCTGGATCTACTTATTGGAGATGCTCTG

GCGACTTGGTGCCACCATCTGGCAGCTTTTGGCCTTCTTCCTAGC

CTTCTTCCTAGACCTCATCCTGCTCATTATTGCTCTCTATCTACA

ACAAAACTGGTGGACTCTATTGGTTGATCTCCTTTGGCTCCTCCT

GTTTCTGGCGATTTTAATCTGGATGTATTACCATGGACAACGAAT

GTCTGCGGGAGACCCCCGCGTGGGATCCGGGTCCCTGGACTCCTT

CATGTTCTCCATACCCTTGGTCGCGCTTAACGTGGGAGTGAGGCG

CCGCCTATCGCTGTTCTTGAACCCTCGGACGCCCGTGGCGGCCGA

CTGGACCTTGCTGGCGGAGGAGATGGGCTTCGAGTACTTGGAGAT

CCGAGAGCTGGAAACGCGCCCTGACCCCACTCGCAGTTTGTTGGA

-continued

TGCCTGGCAGGGGCGCTCTGGCGCGTCTGTCGGCAGGCTGCTAGA

GCTGCTGGCCTTGTTAGACCGTGAGGATATACTGAAGGAGCTGAA

GTCGCGCATCGAGGAGGACTGCCAGAAATACTTAGGTAAGCAGCA

GAACCAGGAGTCCGAGAAGCCTTTACAGGTGGCCAGAGTGGAAAC

CAGTGTCCCACAAACAAAGGAACTGGGAGGCATCACCACCCTTGA

TGACCCCCTAGGACAAACGCCGGAACTTTTCGATGCCTTTATCTG

CTACTGCCCCAACGATATCGAGTTTGTGCAGGAGATGATCCGGCA

ACTAGAACAGACAGACTATCGGCTTAAGTTGTGTGTGTCCGACCG

TGACGTCCTGCCGGGCACCTGTGTCTGGTCCATTGCCAGCGAGCT

AATTGAGAAAAGGTGTCGCCGCATGGTGGTGGTTGTTTCTGACGA

TTATCTACAGAGCAAGGAATGTGACTTCCAGACCAAGTTTGCACT

CAGCCTGTCTCCAGGTGTCCAACAGAAGCGACTGATTCCTATTAA

ATACAAGGCGATGAAGAAGGACTTTCCCAGTATCCTGCGGTTCAT

CACTATATGCGACTATACCAACCCTTGCACCAAGTCCTGGTTCTG

GACCCGCCTTGCCAAGGCTTTGTCCCTGGTCGAGTATATCAAAAA

GGTGGTCAAGAAACCAAAGGATAATGAGATCTTACCCCCTGCGGC

TCGACGGCAAGATCCCCAGGAGATGGAAGATTATCCCGGTCATAA

CACCGCTGCTCCAGTGCAGGAGACGCTGCACGGGTGTCAGCCTGT

CACACAGGAGGATGGTAAAGAGAGTCGCATCTCAGTGCAGGAGCG

GCAGGTGACAGACAGCATAGCCTTGAGGCCCCTGGTCTGA

SEQ ID NO:14 is Nuclear Protein (NP).

Protein:

(SEQ ID NO: 14)

MASQGTKRSYEQMETDGERQNATEIRASVGKMIGGIGRFYIQMCTELKLS

DYEGRLIQNSLTIERMVLSAFDERRNKYLEEHPSAGKDPKKTGGPIYRRV

NGKWMRELILYDKEEIRRIWRQANNGDDATAGLTHMMIWHSNLNDATYQR

TRALVRTGMDPRMCSLMQGSTLPRRSGAAGAAVKGVGTMVMELVRMIKRG

INDRNFWRGENGRKTRIAYERMCNILKGKFQTAAQKAMMDQVRESRNPGN

AEFEDLTFLARSALILRGSVAHKSCLPACVYGPAVASGYDFEREGYSLVG

IDPFRLLQNSQVYSLIRPNENPAHKSQLVWMACHSAAFEDLRVLSFIKGT

KVLPRGKLSTRGVQIASNENMETMESSTLELRSRYWAIRTRSGGNTNQQR

ASAGQISIQPTFSVQRNLPFDRTTIMAAFNGNTEGRTSDMRTEIIRMMES

ARPEDVSFQGRGVFELSDEKAASPIVPSFDMSNEGSYFFGDNAEEYDN

SEQ ID NO:15 is Epstein Barr Virus latent membrane protein 1 (without the cytoplasmic domain) fused to the murine protein MyD88 fused to the cytoplasmic domain of murine CD40.

Protein:

(SEQ ID NO: 15)
MEHDLERGPPGPRRPPRGPPLSSSLGLALLLLLLALLFWLYIVMSDWTGGA
LLVLYSFALMLIIIILIIFIFRRDLLCPLGALCILLLMITLLLIALWNLHG
QALFLGIVLFIFGCLLVLGIVVIYLLEMLWRLGATIWQLLAFFLAFFLDLI
LLIIALYLQQNWWTLLVDLLWLLLFLAILIWMYYHGQRMSAGDPRVGSGSL
DSFMFSIPLVALNVGVRRRLSLFLNPRTPVAADWTLLAEEMGFEYLEIREL
ETRPDPTRSLLDAWQGRSGASVGRLLELLALLDREDILKELKSRIEEDCQK
YLGKQQNQESEKPLQVARVESSVPQTKELGGITTLDDPLGQTPELFDAFIC
YCPNDIEFVQEMIRQLEQTDYRLKLCVSDRDVLPGTCVWSIASELIEKRCR
RMVVVVSDDYLQSKECDFQTKFALSLSPGVQQKRLIPIKYKAMKKDFPSIL
RFITICDYTNPCTKSWFWTRLAKALSLVEYIKKVVKKPKDNEILPPAARRQ
DPQEMEDYPGHNTAAPVQETLHGCQPVTQEDGKESRISVQERQVTD-
SIALR
PLV

SEQ ID NO:16 is Epstein Barr Virus latent membrane protein 1 (without the cytoplasmic domain) fused to murine MyD88 and the cytoplasmic domain of murine CD40 as a single 3-protein chimera.

LMP1-muMyD88-muCD40

Italicized/bolded sequence: LMP1 sequence (Transmembrane Domain)
Non-italicized/bolded sequence: Murine MyD88 sequence
Underlined sequence: Linker
Bolded sequence: Murine CD40 sequence (cytoplasmic domain)

(SEQ ID NO: 16)
*ATGGAACACGACCTTGAGAGGGGCCCACCGGGCCCGCGACGGCCC*
*CCTCGAGGACCCCCCCTCTCCTCTTCCCTAGGCCTTGCTCTCCTT*
*CTCCTCCTCTTGGCGCTACTGTTTTGGCTGTACATCGTTATGAGT*
*GACTGGACTGGAGGAGCCCTCCTTGTCCTCTATTCCTTTGCTCTC*
*ATGCTTATAATTATAATTTTGATCATCTTTATCTTCAGAAGAGAC*
*CTTCTCTGTCCACTTGGAGCCCTTTGTATACTCCTACTGATGATC*
*ACCCTCCTGCTCATCGCTCTCTGGAATTTGCACGGACAGGCATTG*
*TTCCTTGGAATTGTGCTGTTCATCTTCGGGTGCTTACTTGTCTTA*
*GGTATCTGGATCTACTTATTGGAGATGCTCTGGCGACTTGGTGCC*
*ACCATCTGGCAGCTTTTGGCCTTCTTCCTAGCCTTCTTCCTAGAC*
*CTCATCCTGCTCATTATTGCTCTCTATCTACAACAAAACTGGTGG*
*ACTCTATTGGTTGATCTCCTTTGGCTCCTCCTGTTTCTGGCGATT*
*TTAATCTGGATGTATTACCATGGACAACGA*ATGTCTGCGGGAGAC
CCCCGCGTGGGATCCGGGTCCCTGGACTCCTTCATGTTCTCCATA
CCCTTGGTCGCGCTTAACGTGGGAGTGAGGCGCCGCCTATCGCTG

-continued

TTCTTGAACCCTCGGACGCCCGTGGCGGCCGACTGGACCTTGCTG
GCGGAGGAGATGGGCTTCGAGTACTTGGAGATCCGAGAGCTGGAA
ACGCGCCCTGACCCCACTCGCAGTTTGTTGGATGCCTGGCAGGGG
CGCTCTGGCGCGTCTGTCGGCAGGCTGCTAGAGCTGCTGGCCTTG
TTAGACCGTGAGGATATACTGAAGGAGCTGAAGTCGCGCATCGAG
GAGGACTGCCAGAAATACTTAGGTAAGCAGCAGAACCAGGAGTCC
GAGAAGCCTTTACAGGTGGCCAGAGTGGAAAGCAGTGTCCCACAA
ACAAAGGAACTGGGAGGCATCACCACCCTTGATGACCCCCTAGGA
CAAACGCCGGAACTTTTCGATGCCTTTATCTGCTACTGCCCCAAC
GATATCGAGTTTGTGCAGGAGATGATCCGGCAACTAGAACAGACA
GACTATCGGCTTAAGTTGTGTGTGTCCGACCGTGACGTCCTGCCG
GGCACCTGTGTCTGGTCCATTGCCAGCGAGCTAATTGAGAAAAGG
TGTCGCCGCATGGTGGTGGTTGTTTCTGACGATTATCTACAGAGC
AAGGAATGTGACTTCCAGACCAAGTTTGCACTCAGCCTGTCTCCA
GGTGTCCAACAGAAGCGACTGATTCCTATTAAATACAAGGCGATG
AAGAAGGACTTTCCCAGTATCCTGCGGTTCATCACTATATGCGAC
TATACCAACCCTTGCACCAAGTCCTGGTTCTGGACCCGCCTTGCC
AAGGCTTTGTCCCTGGTCGAGTATATCAAAAAGGTGGTCAAGAAA
CCAAAGGATAATGAGATCTTACCCCCTGCGGCTCGACGGCAAGAT
CCCCAGGAGATGGAAGATTATCCCGGTCATAACACCGCTGCTCCA
GTGCAGGAGACGCTGCACGGGTGTCAGCCTGTCACACAGGAGGAT
GGTAAAGAGAGTCGCATCTCAGTGCAGGAGCGGCAGGTGACAGAC
AGCATAGCCTTGAGGCCCCTGGTCTGA

SEQ ID NO:17 is Epstein Barr Virus latent membrane protein 1 (without the cytoplasmic domain) fused to the murine protein MyD88 fused to the cytoplasmic domain of murine CD40.

Protein:

(SEQ ID NO: 17)
MEHDLERGPPGPRRPPRGPPLSSSLGLALLLLLLALLFWLYIVMSDWTGG
ALLVLYSFALMLIIIILIIFIFRRDLLCPLGALCILLLMITLLLIALWNL
HGQALFLGIVLFIFGCLLVLGIWIYLLEMLWRLGATIVVQLLAFFLAFFL
DLILLIIALYLQQNWWTLLVDLLWLLLFLAILIWMYYHGQRMSAGDPRVG
SGSLDSFMFSIPLVALNVGVRRRLSLFLNPRTPVAADWTLLAEEMGFEYL
EIRELETRPDPTRSLLDAWQGRSGASVGRLLELLALLDREDILKELKSRI
EEDCQKYLGKQQNQESEKPLQVARVESSVPQTKELGGITTLDDPLGQTPE
LFDAFICYCPNDIEFVQEMIRQLEQTDYRLKLCVSDRDVLPGTCVWSIAS
ELIEKRCRRMVVVVSDDYLQSKECDFQTKFALSLSPGVQQKRLIPIKYKA

-continued

MKKDFPSILRFITICDYTNPCTKSWFWTRLAKALSLVEYIKKVVKKPKDN

EILPPAARRQDPQEMEDYPGHNTAAPVQETLHGCQPVTQEDGKESRISVQ

ERQVTDSIALRPLV

SEQ ID NO:18 is Epstein Barr Virus latent membrane protein 1 (without the cytoplasmic domain) fused to human IPS-1, the cytoplasmic domain of human TLR7, and the cytoplasmic domain (CD) of Epstein Barr Virus LMP1 as a single chimera.

LMP1-huIPS-1-huTLR7-LMP1(CD)

Italicized/bolded sequence: LMP1 sequence (Transmembrane Domain)

Non-italicized/bolded sequence: Human IPS-1 sequence

Underlined sequence: Human TLR7 sequence (cytoplasmic domain)

Bolded sequence: LMP1 sequence (cytoplasmic domain)

(SEQ ID NO: 18)

*ATGGAACACGACCTTGAGAGGGGCCCACCGGGCCCGCGACGGCCC*

*CCTCGAGGACCCCCCCTCTCCTCTTCCCTAGGCCTTGCTCTCCTT*

*CTCCTCCTCTTGGCGCTACTGTTTTGGCTGTACATCGTTATGAGT*

*GACTGGACTGGAGGAGCCCTCCTTGTCCTCTATTCCTTTGCTCTC*

*ATGCTTATAATTATAATTTTGATCATCTTTATCTTCAGAAGAGAC*

*CTTCTCTGTCCACTTGGAGCCCTTTGTATACTCCTACTGATGATC*

*ACCCTCCTGCTCATCGCTCTCTGGAATTTGCACGGACAGGCATTG*

*TTCCTTGGAATTGTGCTGTTCATCTTCGGGTGCTTACTTGTCTTA*

*GGTATCTGGATCTACTTATTGGAGATGCTCTGGCGACTTGGTGCC*

*ACCATCTGGCAGCTTTTGGCCTTCTTCCTAGCCTTCTTCCTAGAC*

*CTCATCCTGCTCATTATTGCTCTCTATCTACAACAAAACTGGTGG*

*ACTCTATTGGTTGATCTCCTTTGGCTCCTCCTGTTTCTGGCGATT*

*TTAATCTGGATGTATTACCATGGACAACGA*ATGCCGTTTGCTGAA

GACAAGACCTATAAGTATATCTGCCGCAATTTCAGCAATTTTTGC

AATGTGGATGTTGTAGAGATTCTGCCTTACCTGCCCTGCCTCACA

GCAAGAGACCAGGATCGACTGCGGGCCACCTGCACACTCTCAGGG

AACCGGGACACCCTCTGGCATCTCTTCAATACCCTTCAGCGGCGG

CCCGGCTGGGTGGAGTACTTCATTGCGGCACTGAGGGGCTGTGAG

CTAGTTGATCTCGCGGACGAAGTGGCCTCTGTCTACCAGAGCTAC

CAGCCTCGGACCTCGGACCGTCCCCCAGACCCACTGGAGCCACCG

TCACTTCCTGCTGAGAGGCCAGGGCCCCCCACACCTGCTGCGGCC

CACAGCATCCCCTACAACAGCTGCAGAGAGAAGGAGCCAAGTTAC

-continued

CCCATGCCTGTCCAGGAGACCCAGGCGCCAGAGTCCCCAGGAGAG

AATTCAGAGCAAGCCCTGCAGACGCTCAGCCCCAGAGCCATCCCA

AGGAATCCAGATGGTGGCCCCCTGGAGTCCTCCTCTGATCTGGCA

GCCCTCAGCCCTCTGACCTCCAGCGGGCATCAGGAGCAGGACACA

GAACTGGGCAGTACCCACACAGCAGGTGCGACCTCCAGCCTCACA

CCATCCCGTGGGCCTGTGTCTCCATCTGTCTCCTTCCAGCCCCTG

GCCCGTTCCACCCCCAGGGCAAGCCGCTTGCCTGGACCCACAGGG

TCAGTTGTATCTACTGGCACCTCCTTCTCCTCCTCATCCCCTGGC

TTGGCCTCTGCAGGGGCTGCAGAGGGTAAACAGGGTGCAGAGAGT

GACCAGGCCGAGCCTATCATCTGCTCCAGTGGGGCAGAGGCACCT

GCCAACTCTCTGCCCTCCAAAGTGCCTACCACCTTGATGCCTGTG

AACACAGTGGCCCTGAAAGTGCCTGCCAACCCAGCATCTGTCAGC

ACAGTGCCCTCCAAGTTGCCAACTAGCTCAAAGCCCCCTGGTGCA

GTGCCTTCTAATGCGCTCACCAATCCAGCACCATCCAAATTGCCC

ATCAACTCAACCCGTGCTGGCATGGTGCCATCCAAAGTGCCTACT

AGCATGGTGCTCACCAAGGTGTCTGCCAGCACAGTCCCCACTGAC

GGGAGCAGCAGAAATGAGGAGACCCCAGCAGCTCCAACACCCGCC

GGCGCCACTGGAGGCAGCTCAGCCTGGCTAGACAGCAGCTCTGAG

AATAGGGGCCTTGGGTCGGAGCTGAGTAAGCCTGGCGTGCTGGCA

TCCCAGGTAGACAGCCCGTTCTCGGGCTGCTTCGAGGATCTTGCC

ATCAGTGCCAGCACCTCCTTGGGCATGGGGCCCTGCCATGGCCCA

GAGGAGAATGAGTATAAGTCCGAGGGCACCTTTGGGATCCACGTG

GCTGAGAACCCCAGCATCCAGCTCCTGGAGGGCAACCCTGGGCCA

CCTGCGGACCCGGATGGCGGCCCCAGGCCACAAGCCGACCGGAAG

TTCCAGGAGAGGGAGGTGCCATGCCACAGGCCCTCACCTGGGGCT

CTGTGGCTCCAGGTGGCTGTGACAGGGGTGCTGGTAGTCACACTC

CTGGTGGTGCTGTACCGGCGGCGTCTGCACCACCTCTATTTCTGG

GATGTGTGGTATATTTACCATTTCTGTAAGGCCAAGATAAAGGGG

TATCAGCGTCTAATATCACCAGACTGTTGCTATGATGCTTTTATT

GTGTATGACACTAAAGACCCAGCTGTGACCGAGTGGGTTTTGGCT

GAGCTGGTGGCCAAACTGGAAGACCCAAGAGAGAAACATTTTAAT

TTATGTCTCGAGGAAAGGGACTGGTTACCAGGGCAGCCAGTTCTG

GAAAACCTTTCCCAGAGCATACAGCTTAGCAAAAAGACAGTGTTT

GTGATGACAGACAAGTATGCAAAGACTGAAAATTTTAAGATAGCA

TTTTACTTGTCCCATCAGAGGCTCATGGATGAAAAAGTTGATGTG

-continued

ATTATCTTGATATTTCTTGAGAAGCCCTTTCAGAAGTCCAAGTTC

CTCCAGCTCCGGAAAAGGCTCTGTGGGAGTTCTGTCCTTGAGTGG

CCAACAAACCCGCAAGCTCACCCATACTTCTGGCAGTGTCTAAAG

AACGCCCTGGCCACAGACAATCATGTGGCCTATAGTCAGGTGTTC

AAGGAAACGGTCCACAGTGATGAACACCACCACGATGACTCCCTC

CCGCACCCTCAACAAGCTACCGATGATTCTGGCCATGAATCTGAC

TCTAACTCCAACGAGGGCAGACACCACCTGCTCGTGAGTGGAGCC

GGCGACGGACCCCCACTCTGCTCTCAAAACCTAGGCGCACCTGGA

GGTGGTCCTGACAATGGCCCACAGGACCCTGACAACACTGATGAC

AATGGCCCACAGGACCCTGACAACACTGATGACAATGGCCCACAT

GACCCGCTGCCTCAGGACCCTGACAACACTGATGACAATGGCCCA

CAGGACCCTGACAACACTGATGACAATGGCCCACATGACCCGCTG

CCTCATAGCCCTAGCGACTCTGCTGGAAATGATGGAGGCCCTCCA

CAATTGACGGAAGAGGTTGAAAACAAAGGAGGTGACCAGGGCCCG

CCTTTGATGACAGACGGAGGCGGCGGTCATAGTCATGATTCCGGC

CATGGCGGCGGTGATCCACACCTTCCTACGCTGCTTTTGGGTTCT

TCTGGTTCCGGTGGAGATGATGACGACCCCCACGGCCCAGTTCAG

CTAAGCTACTATGACTAA

SEQ ID NO:19 is Epstein Barr Virus latent membrane protein 1 (without the cytoplasmic domain) fused to the human IPS-1 fused to the cytoplasmic domain of human TLR7 fused to the cytoplasmic domain of Epstein Barr Virus latent membrane protein 1.

Protein:

(SEQ ID NO: 19)

MEHDLERGPPGPRRPPRGPPLSSSLGLALLLLLLALLFWLYIVMSDWTGGA

LLVLYSFALMLIIIILIIFIFRRDLLCPLGALCILLLMITLLLIALWNLHG

QALFLGIVLFIFGCLLVLGIWIYLLEMLWRLGATIVVQLLAFFLAFFLDLI

LLIIALYLQQNWVVTLLVDLLWLLLFLAILIWMYYHGQRMPFAEDKTYKYI

CRNFSNFCNVDVVEILPYLPCLTARDQDRLRATCTLSGNRDTLWHLFNTLQ

-continued

RRPGWVEYFIAALRGCELVDLADEVASVYQSYQPRTSDRPPDPLEPPSLPA

ERPGPPTPAAAHSIPYNSCREKEPSYPMPVQETQAPESPGENSEQALQTLS

PRAIPRNPDGGPLESSSDLAALSPLTSSGHQEQDTELGSTHTAGATSSLTP

SRGPVSPSVSFQPLARSTPRASRLPGPTGSVVSTGTSFSSSSPGLASAGAA

EGKQGAESDQAEPIICSSGAEAPANSLPSKVPTTLMPVNTVALKVPANPAS

VSTVPSKLPTSSKPPGAVPSNALTNPAPSKLPINSTRAGMVPSKVPTSMVL

TKVSASTVPTDGSSRNEETPAAPTPAGATGGSSAWLDSSSENRGLGSELSK

PGVLASQVDSPFSGCFEDLAISASTSLGMGPCHGPEENEYKSEGTFGIHVA

ENPSIQLLEGNPGPPADPDGGPRPQADRKFQEREVPCHRPSPGALWLQVAV

TGVLVVTLLVVLYRRRLHHLYFWDVWYIYHFCKAKIKGYQRLISPDCCYDA

FIVYDTKDPAVTEWVLAELVAKLEDPREKHFNLCLEERDWLPGQPVLENLS

QSIQLSKKTVFVMTDKYAKTENFKIAFYLSHQRLMDEKVDVIILIFLEKPF

QKSKFLQLRKRLCGSSVLEWPTNPQAHPYFWQCLKNALATDNHVAYSQVFK

ETVHSDEHHHDDSLPHPQQATDDSGHESDSNSNEGRHHLLVSGAGDGPPLC

SQNLGAPGGGPDNGPQDPDNTDDNGPQDPDNTDDNGPHDPLPQDPDNTDDN

GPQDPDNTDDNGPHDPLPHSPSDSAGNDGGPPQLTEEVENKGGDQGPPLMT

DGGGGHSHDSGHGGGDPHLPTLLLGSSGSGGDDDDPHGPVQLSYYD

OTHER EMBODIMENTS

Any improvement may be made in part or all of the compositions, cells, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A vector comprising a nucleic acid encoding a fusion protein, the fusion protein comprising a transmembrane domain of LMP1 and an amino acid sequence comprising one or more signaling motifs from immune activating receptors and/or adaptor proteins, where the immune activating receptor is not a TNF Receptor Superfamily (TNFRSF) protein.

2. The vector of claim 1, wherein the vector is a plasmid, a virus, a prokaryotic chromosome or a eukaryotic chromosome.

3. The vector of claim 1, wherein the vector is a viral vector.

4. The vector of claim 3, wherein the viral vector is a lentivirus, an adenovirus, an adeno-associated virus, a retrovirus, a rhabdovirus, a poxvirus, an alphavirus, or a Herpesvirus.

5. The vector of claim 4, wherein the viral vector is an MMLV, an HIV-1, an ALV, a vesicular stomatitis virus, a vaccinia virus, a Venezuelan equine encephalitis virus, a Semliki Forest virus, a Sindbis virus, or a cytomegalovirus virus.

6. The vector of claim 1, wherein the vector is an RNA vector.

7. The vector of claim 1, wherein the nucleic acid is a cDNA, a polymerase chain reaction extension product, a recombinant nucleic acid or a synthetic nucleic acid.

8. The vector of claim 1, wherein the immune activating receptor or adaptor protein is an integrin, FcγRIII, Dectin1, Dectin2, NOD1, NOD2, CD16, IL-2R, Type 1 interferon receptor, Type 2 interferon receptor, a chemokine receptor, a G-protein coupled receptor (GPCR), TREM1, or a member of the B cell receptor (BCR) complex.

9. The vector of claim 8, wherein the chemokine receptor is CCR5 or CCR7.

10. The vector of claim 8, wherein the member of the B cell receptor complex is CD79A, CD79B, or Immunoglobulin-alpha.

11. The vector of claim 1, wherein the adaptor protein is IPS-1, MyD88, RIG-1, MDA5, CD3 zeta chain, MyD88ΔTIR, TRIF, TRAM, TIRAP, MAL, BTK, RTK, RAC1, SYK, NALP3 (NLRP3), NALP3ΔLRR, NALP1, CARD9, DAI, IPAG, STING, Zap70, or LAT.

12. The vector of claim 1, wherein the nucleic acid further encodes an antigen.

13. The vector of claim 1, wherein the nucleic acid comprises a first nucleic acid, the vector further comprising a second nucleic acid encoding a second fusion protein, the second fusion protein comprising a transmembrane domain of LMP1 and at least one signaling domain from an immune activating receptor or an adaptor protein.

14. The vector of claim 1, wherein the nucleic acid is present in an amount effective for inducing expression of cytokines that protect CD4+ T cells from infection by a virus.

15. The vector of claim 14, wherein the virus is human immunodeficiency virus (HIV), and the subject is a human.

16. The vector of claim 14, wherein the fusion protein comprises a transmembrane domain of LMP1 and a signaling domain from IPS-1.

17. The vector of claim 1, wherein the vector is pcDNA3.1.

18. The vector of claim 1, wherein the nucleic acid encodes a fusion protein comprising a transmembrane domain of LMP1 and an amino acid sequence comprising two or more signaling motifs from immune activating receptors and/or adaptor proteins, and wherein the nucleic acid is present in an amount sufficient to induce an immune response in a subject.

19. A vaccine formulation for preventing or treating a disease or condition in a subject comprising the vector of claim 1 and a pharmaceutically acceptable excipient.

20. The vaccine formulation of claim 19, wherein the disease or condition is cancer or infection.

21. An immune cell transduced with the vector of claim 1.

22. The immune cell of claim 21, wherein the immune cell is comprised within a vaccine formulation for preventing or treating a disease or condition in a subject.

23. The immune cell of claim 22, wherein the vaccine formulation further comprises an antigen or a nucleic acid encoding an antigen in an amount effective for enhancing an immune response and a pharmaceutically acceptable excipient.

* * * * *

SEQUENCE LISTING

<160> NUMBER OF SEQ ID NOS: 19

<210> SEQ ID NO 1
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: Misc_feature
<223> OTHER INFORMATION: Epstein Barr Virus latent membrane protein 1

(without the cytoplasmic domain) fused to the cytoplasmic domain of murine TLR7

<400> SEQUENCE: 1

```
atggaacacg accttgagag gggcccaccg ggcccgcgac ggcccccctcg aggaccccccc     60

ctctcctctt ccctaggcct tgctctcctt ctcctcctct tggcgctact gttttggctg    120

tacatcgtta tgagtgactg gactggagga gccctccttg tcctctattc ctttgctctc    180

atgcttataa ttataatttt gatcatcttt atcttcagaa gagaccttct ctgtccactt    240

ggagcccttt gtatactcct actgatgatc accctcctgc tcatcgctct ctggaatttg    300

cacggacagg cattgttcct tggaattgtg ctgttcatct tcgggtgctt acttgtctta    360

ggtatctgga tctacttatt ggagatgctc tggcgacttg gtgccaccat ctggcagctt    420

ttggccttct tcctagcctt cttcctagac ctcatcctgc tcattattgc tctctatcta    480

caacaaaact ggtggactct attggttgat ctcctttggc tcctcctgtt tctggcgatt    540

ttaatctgga tgtattacca tggacaacga acaacaagtc acctcttttt ctgggatatg    600

tggtacattt attatttttg gaaagcaaag ataaaggggt atcagcatct gcaatccatg    660

gagtcttgtt atgatgcttt tattgtgtat gacactaaaa actcagctgt gacagaatgg    720

gttttgcagg agctggtggc aaaattggaa gatccaagag aaaaacactt caatttgtgt    780

ctagaagaaa gagactggct accaggacag ccagttctag aaaacctttc ccagagcata    840

cagctcagca aaaagacagt gtttgtgatg acacagaaat atgctaagac tgagagtttt    900

aagatggcat tttatttgtc tcatcagagg ctcctggatg aaaaagtgga tgtgattatc    960

ttgatattct tggaaaagcc tcttcagaag tctaagtttc ttcagctcag gaagagactc   1020

tgcaggagct ctgtccttga gtggcctgca aatccacagg ctcacccata cttctggcag   1080

tgcctgaaaa atgccctgac cacagacaat catgtggctt atagtcaaat gttcaaggaa   1140

acagtctag                                                           1149
```

<210> SEQ ID NO 2
<211> LENGTH: 382
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1 (without the cytoplasmic domain) fused to the cytoplasmic domain of murine TLR7

<400> SEQUENCE: 2

```
Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
            20                  25                  30

Leu Leu Ala Leu Leu Phe Trp Leu Tyr Ile Val Met Ser Asp Trp Thr
        35                  40                  45

Gly Gly Ala Leu Leu Val Leu Tyr Ser Phe Ala Leu Met Leu Ile Ile
    50                  55                  60

Ile Ile Leu Ile Ile Phe Ile Phe Arg Arg Asp Leu Leu Cys Pro Leu
65                  70                  75                  80

Gly Ala Leu Cys Ile Leu Leu Leu Met Ile Thr Leu Leu Leu Ile Ala
                85                  90                  95

Leu Trp Asn Leu His Gly Gln Ala Leu Phe Leu Gly Ile Val Leu Phe
```

```
            100                 105                 110

Ile Phe Gly Cys Leu Leu Val Leu Gly Ile Trp Ile Tyr Leu Leu Glu
        115                 120                 125

Met Leu Trp Arg Leu Gly Ala Thr Ile Trp Gln Leu Leu Ala Phe Phe
    130                 135                 140

Leu Ala Phe Phe Leu Asp Leu Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Thr Thr
            180                 185                 190

Ser His Leu Phe Phe Trp Asp Met Trp Tyr Ile Tyr Tyr Phe Trp Lys
        195                 200                 205

Ala Lys Ile Lys Gly Tyr Gln His Leu Gln Ser Met Glu Ser Cys Tyr
    210                 215                 220

Asp Ala Phe Ile Val Tyr Asp Thr Lys Asn Ser Ala Val Thr Glu Trp
225                 230                 235                 240

Val Leu Gln Glu Leu Val Ala Lys Leu Glu Asp Pro Arg Glu Lys His
                245                 250                 255

Phe Asn Leu Cys Leu Glu Glu Arg Asp Trp Leu Pro Gly Gln Pro Val
            260                 265                 270

Leu Glu Asn Leu Ser Gln Ser Ile Gln Leu Ser Lys Lys Thr Val Phe
        275                 280                 285

Val Met Thr Gln Lys Tyr Ala Lys Thr Glu Ser Phe Lys Met Ala Phe
    290                 295                 300

Tyr Leu Ser His Gln Arg Leu Leu Asp Glu Lys Val Asp Val Ile Ile
305                 310                 315                 320

Leu Ile Phe Leu Glu Lys Pro Leu Gln Lys Ser Lys Phe Leu Gln Leu
                325                 330                 335

Arg Lys Arg Leu Cys Arg Ser Ser Val Leu Glu Trp Pro Ala Asn Pro
            340                 345                 350

Gln Ala His Pro Tyr Phe Trp Gln Cys Leu Lys Asn Ala Leu Thr Thr
        355                 360                 365

Asp Asn His Val Ala Tyr Ser Gln Met Phe Lys Glu Thr Val
    370                 375                 380
```

<210> SEQ ID NO 3
<211> LENGTH: 822
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Epstein Barr Virus latent membrane protein 1 (without the cytoplasmic domain) fused to the cytoplasmic domain of murine BAFF receptor

<400> SEQUENCE: 3

```
atggaacacg accttgagag gggcccaccg ggcccgcgac ggcccccctcg aggaccccccc      60

ctctcctctt ccataggcct tgctctcctt ctcctgctct tggcgctact gttttggctg     120

tacatcatta tgagtaactg gactggagga gccctccttg tcctctatgc ctttgctctc     180

atgcttgtga ttatcatttt gatcatcttt atcttcagaa gagaccttct ctgtccactt     240

ggagcccttt gtctactcct actgatgatc accctcctgc tcatcgctct ctggaatttg     300

cacggacagg cattgtacct tggaattgtg ctgttcatct tcgggtgctt acttgtctta     360
```

-continued

```
ggtctctgga tctacttatt ggagattctc tggcgacttg gtgccaccat ctggcagctt    420

ttggccttct tcctagcctt cttcctagac atcatcctgc tcattattgc tctctatcta    480

caacaaaact ggtggactct attggttgat ctcctttggc tcctcctgtt tctggcgatt    540

ttaatctgga tgtattacca tggacaacga agtctggtga gctggaggtg gcgtcaacag    600

ctcaggacgg cctccccaga cacttcagaa ggagtccagc aagagtccct ggaaaatgtc    660

tttgtaccct cctcagaaac ccctcatgcc tcagctccta cctggcctcc gctcaaagaa    720

gatgcagaca gcgccctgcc acgccacagc gtcccggtgc ccgccacaga actgggctcc    780

accgagctgg tgaccaccaa gacagctggc ccagagcaat ag                       822


<210> SEQ ID NO 4
<211> LENGTH: 273
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1
      (without the cytoplasmic domain) fused to the cytoplasmic domain
      of murine BAFF receptor

<400> SEQUENCE: 4

Met Glu His Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Ser Leu
            180                 185                 190

Val Ser Trp Arg Trp Arg Gln Gln Leu Arg Thr Ala Ser Pro Asp Thr
        195                 200                 205

Ser Glu Gly Val Gln Gln Glu Ser Leu Glu Asn Val Phe Val Pro Ser
    210                 215                 220

Ser Glu Thr Pro His Ala Ser Ala Pro Thr Trp Pro Pro Leu Lys Glu
225                 230                 235                 240

Asp Ala Asp Ser Ala Leu Pro Arg His Ser Val Pro Val Pro Ala Thr
                245                 250                 255
```

Glu Leu Gly Ser Thr Glu Leu Val Thr Thr Lys Thr Ala Gly Pro Glu
260 265 270

Gln

<210> SEQ ID NO 5
<211> LENGTH: 1089
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Epstein Barr Virus latent membrane protein 1 (without the cytoplasmic domain) fused to the CARD domain of murine RIG-I

<400> SEQUENCE: 5
atggaacacg accttgagag gggcccaccg ggcccgcgac ggcccccctcg aggaccccc 60 ctctcctctt ccataggcct tgctctcctt ctcctgctct tggcgctact gttttggctg 120
tacatcatta tgagtaactg gactggagga gccctccttg tcctctatgc ctttgctctc 180
atgcttgtga ttatcatttt gatcatcttt atcttcagaa gagaccttct ctgtccactt 240
ggagcccttt gtctactcct actgatgatc accctcctgc tcatcgctct ctggaatttg 300
cacggacagg cattgtacct tggaattgtg ctgttcatct tcgggtgctt acttgtctta 360
ggtctctgga tctacttatt ggagattctc tggcgacttg gtgccaccat ctggcagctt 420
ttggccttct tcctagcctt cttcctagac atcatcctgc tcattattgc tctctatcta 480
caacaaaact ggtggactct attggttgat ctcctttggc tcctcctgtt tctggcgatt 540
ttaatctgga tgtattacca tggacaacga atgaccgcgg cgcagcggca gaatctgcaa 600
gcattcagag actatatcaa gaagattctg gaccccacct acatcctcag ctacatgagt 660
tcctggctcg aggatgagga ggtgcagtac attcaggctg agaagaacaa caagggccca 720
atggaagctg cctcactctt cctccagtac ctgttgaagc tgcagtcaga gggctggttc 780
caggcctttt tggatgccct gtaccatgca ggttactgtg gactttgtga agccatcgaa 840
agttgggact ttcaaaaaat tgaaaagtta gaggaacaca gattactttt aagacgttta 900
gaaccagaat ttaaggccac agttgatcca aatgatatcc tttctgaact atccgaatgt 960
ttgattaatc aggaatgtga agaaatcaga cagatccgag acactaaagg gagaatggca 1020
ggtgcggaga agatggccga atgtcttatc agatccgaca aggaaaactg gccaaaggtc 1080
ttgcaatag 1089

<210> SEQ ID NO 6
<211> LENGTH: 362
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1 (without the cytoplasmic domain) fused to the CARD domain of murine RIG-I

<400> SEQUENCE: 6

Met Glu His Asp Leu Glu Arg Gly Pro Pro Gly Pro Arg Arg Pro Pro
1 5 10 15

Arg Gly Pro Pro Leu Ser Ser Ser Ile Gly Leu Ala Leu Leu Leu Leu
20 25 30

```
Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Met Thr
            180                 185                 190

Ala Ala Gln Arg Gln Asn Leu Gln Ala Phe Arg Asp Tyr Ile Lys Lys
        195                 200                 205

Ile Leu Asp Pro Thr Tyr Ile Leu Ser Tyr Met Ser Ser Trp Leu Glu
    210                 215                 220

Asp Glu Glu Val Gln Tyr Ile Gln Ala Glu Lys Asn Asn Lys Gly Pro
225                 230                 235                 240

Met Glu Ala Ala Ser Leu Phe Leu Gln Tyr Leu Leu Lys Leu Gln Ser
                245                 250                 255

Glu Gly Trp Phe Gln Ala Phe Leu Asp Ala Leu Tyr His Ala Gly Tyr
            260                 265                 270

Cys Gly Leu Cys Glu Ala Ile Glu Ser Trp Asp Phe Gln Lys Ile Glu
        275                 280                 285

Lys Leu Glu Glu His Arg Leu Leu Leu Arg Arg Leu Glu Pro Glu Phe
    290                 295                 300

Lys Ala Thr Val Asp Pro Asn Asp Ile Leu Ser Glu Leu Ser Glu Cys
305                 310                 315                 320

Leu Ile Asn Gln Glu Cys Glu Glu Ile Arg Gln Ile Arg Asp Thr Lys
                325                 330                 335

Gly Arg Met Ala Gly Ala Glu Lys Met Ala Glu Cys Leu Ile Arg Ser
            340                 345                 350

Asp Lys Glu Asn Trp Pro Lys Val Leu Gln
        355                 360
```

<210> SEQ ID NO 7
<211> LENGTH: 1458
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Epstein Barr Virus latent membrane protein 1
(without the cytoplasmic domain) fused to human MyD88

<400> SEQUENCE: 7

```
atggaacacg accttgagag gggcccaccg ggcccgcgac ggccccctcg aggaccccc      60
```

```
ctctcctctt ccataggcct tgctctcctt ctcctgctct tggcgctact gttttggctg    120
tacatcatta tgagtaactg gactggagga gccctccttg tcctctatgc ctttgctctc    180
atgcttgtga ttatcatttt gatcatcttt atcttcagaa gagaccttct ctgtccactt    240
ggagcccttt gtctactcct actgatgatc accctcctgc tcatcgctct ctggaatttg    300
cacggacagg cattgtacct tggaattgtg ctgttcatct tcgggtgctt acttgtctta    360
ggtctctgga tctacttatt ggagattctc tggcgacttg gtgccaccat ctggcagctt    420
ttggccttct tcctagcctt cttcctagac atcatcctgc tcattattgc tctctatcta    480
caacaaaact ggtggactct attggttgat ctcctttggc tcctcctgtt tctggcgatt    540
ttaatctgga tgtattacca tggacaacga atggctgcag gaggtcccgg cgcggggtct    600
gcggccccgg tctcctccac atcctccctt cccctggctg ctctcaacat gcgagtgcgg    660
cgccgcctgt ctctgttctt gaacgtgcgg acacaggtgg cggccgactg gaccgcgctg    720
gcggaggaga tggactttga gtacttggag atccggcaac tggagacaca agcggacccc    780
actggcaggc tgctggacgc ctggcaggga cgccctggcg cctctgtagg ccgactgctc    840
gagctgctta ccaagctggg ccgcgacgac gtgctgctgg agctgggacc cagcattgag    900
gaggattgcc aaaagtatat cttgaagcag cagcaggagg aggctgagaa gcctttacag    960
gtggccgctg tagacagcag tgtcccacgg acagcagagc tggcgggcat caccacactt   1020
gatgaccccc tggggcatat gcctgagcgt ttcgatgcct tcatctgcta ttgccccagc   1080
gacatccagt ttgtgcagga gatgatccgg caactggaac agacaaacta tcgactgaag   1140
ttgtgtgtgt ctgaccgcga tgtcctgcct ggcacctgtg tctggtctat tgctagtgag   1200
ctcatcgaaa agaggtgccg ccggatggtg gtggttgtct ctgatgatta cctgcagagc   1260
aaggaatgtg acttccagac caaatttgca ctcagcctct ctccaggtgc ccatcagaag   1320
cgactgatcc ccatcaagta caaggcaatg aagaaagagt tccccagcat cctgaggttc   1380
atcactgtct gcgactacac caacccctgc accaaatctt ggttctggac tcgccttgcc   1440
aaggccttgt ccctgtga                                                 1458
```

<210> SEQ ID NO 8
<211> LENGTH: 485
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1 (without the cytoplasmic domain) fused to human MyD88

<400> SEQUENCE: 8

```
Met Glu His Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Leu Met Ile Thr Leu Leu Leu Ile Ala
```

-continued

```
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Met Ala
            180                 185                 190

Ala Gly Gly Pro Gly Ala Gly Ser Ala Ala Pro Val Ser Ser Thr Ser
        195                 200                 205

Ser Leu Pro Leu Ala Ala Leu Asn Met Arg Val Arg Arg Arg Leu Ser
    210                 215                 220

Leu Phe Leu Asn Val Arg Thr Gln Val Ala Ala Asp Trp Thr Ala Leu
225                 230                 235                 240

Ala Glu Glu Met Asp Phe Glu Tyr Leu Glu Ile Arg Gln Leu Glu Thr
                245                 250                 255

Gln Ala Asp Pro Thr Gly Arg Leu Leu Asp Ala Trp Gln Gly Arg Pro
            260                 265                 270

Gly Ala Ser Val Gly Arg Leu Leu Glu Leu Leu Thr Lys Leu Gly Arg
        275                 280                 285

Asp Asp Val Leu Leu Glu Leu Gly Pro Ser Ile Glu Glu Asp Cys Gln
    290                 295                 300

Lys Tyr Ile Leu Lys Gln Gln Gln Glu Glu Ala Glu Lys Pro Leu Gln
305                 310                 315                 320

Val Ala Ala Val Asp Ser Ser Val Pro Arg Thr Ala Glu Leu Ala Gly
                325                 330                 335

Ile Thr Thr Leu Asp Asp Pro Leu Gly His Met Pro Glu Arg Phe Asp
            340                 345                 350

Ala Phe Ile Cys Tyr Cys Pro Ser Asp Ile Gln Phe Val Gln Glu Met
        355                 360                 365

Ile Arg Gln Leu Glu Gln Thr Asn Tyr Arg Leu Lys Leu Cys Val Ser
    370                 375                 380

Asp Arg Asp Val Leu Pro Gly Thr Cys Val Trp Ser Ile Ala Ser Glu
385                 390                 395                 400

Leu Ile Glu Lys Arg Cys Arg Arg Met Val Val Val Val Ser Asp Asp
                405                 410                 415

Tyr Leu Gln Ser Lys Glu Cys Asp Phe Gln Thr Lys Phe Ala Leu Ser
            420                 425                 430

Leu Ser Pro Gly Ala His Gln Lys Arg Leu Ile Pro Ile Lys Tyr Lys
        435                 440                 445

Ala Met Lys Lys Glu Phe Pro Ser Ile Leu Arg Phe Ile Thr Val Cys
    450                 455                 460

Asp Tyr Thr Asn Pro Cys Thr Lys Ser Trp Phe Trp Thr Arg Leu Ala
465                 470                 475                 480

Lys Ala Leu Ser Leu
                485
```

<210> SEQ ID NO 9

-continued

<211> LENGTH: 2082
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Epstein Barr Virus latent membrane protein 1
(without the cytoplasmic domain) fused to murine IPS-1

<400> SEQUENCE: 9

```
atggaacacg accttgagag gggcccaccg ggcccgcgac ggcccccctcg aggacccccc     60

ctctcctctt ccataggcct tgctctcctt ctcctgctct tggcgctact gttttggctg    120

tacatcatta tgagtaactg gactggagga gccctccttg tcctctatgc ctttgctctc    180

atgcttgtga ttatcatttt gatcatcttt atcttcagaa gagaccttct ctgtccactt    240

ggagcccttt gtctactcct actgatgatc accctcctgc tcatcgctct ctggaatttg    300

cacggacagg cattgtacct tggaattgtg ctgttcatct tcgggtgctt acttgtctta    360

ggtctctgga tctacttatt ggagattctc tggcgacttg gtgccaccat ctggcagctt    420

ttggccttct tcctagcctt cttcctagac atcatcctgc tcattattgc tctctatcta    480

caacaaaact ggtggactct attggttgat ctcctttggc tcctcctgtt tctggcgatt    540

ttaatctgga tgtattacca tggacaacga atgacatttg ctgaggacaa gacctataag    600

tatatccgag acaaccacag caagttttgc tgtgttgacg ttctggagat cctgccttac    660

ctgtcctgcc tcacagctag tgaccaggat cgactgcggg cttcctacag gcagatcggg    720

aaccgggaca cactctgggg actcttcaat aatctccagc gccggcctgg ctgggtggag    780

gtcttcatcc gggcactgca gatctgtgag ctgcctgggc tggctgatca agtgactcga    840

gtttatcaga gctacctgcc tccgggggacc tcactccgct ccctagagcc actgcagtta    900

ccagactttc ctgctgcggt ttctggaccc tctgcatttg cgccaggtca caacatccct    960

gaccatggct tacgagagac accaagttgc cccaagcctg tccaggacac ccagccacca   1020

gagtccccag tagagaattc agagcaactc ctccagacca actccggggc cgtcgcgagg   1080

atgtctggtg gctctttgat accctctcct aaccagcagg ctctcagccc tcagccctcc   1140

agagagcatc aagagcaaga accagaactg ggtggcgccc acgcagcaaa tgttgcctct   1200

gttcccatag caacctatgg acctgtgtct ccaaccgttt ccttccagcc ccttccacgt   1260

actgccctga ggacaaacct cttgtctggg gtcacagtat cagccctatc tgctgatacc   1320

tctttgtcct cctcgtccac tggatcagct tttgcaaagg gagctggtga ccaggccaaa   1380

gctgccacct gtttcagtac tacactcacc aattctgtga ctaccagctc agtgccttct   1440

cccagattgg tcccagtaaa aaccatgtct tccaagttgc cctcagttc aaagtccact    1500

gctgcgatga cgtctactgt gctcaccaat acagcgccat caaaattacc cagcaactca   1560

gtgtatgcgg gcacagtgcc atccagagtg cctgctagtg tggccaaagc acctgccaac   1620

acaataccac ctgagaggaa cagcaagcaa gccaaggaga ccccggaggg tccagcaacc   1680

aaagtcacca ctggaggcaa ccagactgga ccaaatagca gtatcaggag cttgcactct   1740

ggaccagaga tgagcaagcc aggtgtgctg gtatcccagt tggacgagcc attctcagcc   1800

tgctctgtgg accttgccat tagccctagc agctccttgg tctcagaacc caaccatggt   1860

ccagaggaga atgagtattc gtcctttaga atccaggtag acgaaagccc cagtgctgat   1920

ctattaggaa gccctgagcc actagccacc cagcagcccc aagaagagga agaacattgt   1980

gccagttcaa tgccctgggc taagtggctt ggggccacca gtgcactctt ggctgtattc   2040
```

ctggcagtga tgctgtaccg tagtaggcgc ctggcccagt ga 2082

<210> SEQ ID NO 10
<211> LENGTH: 693
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1 (without the cytoplasmic domain) fused to murine IPS-1

<400> SEQUENCE: 10

Met Glu His Asp Leu Glu Arg Gly Pro Pro Gly Pro Arg Arg Pro Pro
1 5 10 15

Arg Gly Pro Pro Leu Ser Ser Ser Ile Gly Leu Ala Leu Leu Leu Leu
20 25 30

Leu Leu Ala Leu Leu Phe Trp Leu Tyr Ile Ile Met Ser Asn Trp Thr
35 40 45

Gly Gly Ala Leu Leu Val Leu Tyr Ala Phe Ala Leu Met Leu Val Ile
50 55 60

Ile Ile Leu Ile Ile Phe Ile Phe Arg Arg Asp Leu Leu Cys Pro Leu
65 70 75 80

Gly Ala Leu Cys Leu Leu Leu Leu Met Ile Thr Leu Leu Leu Ile Ala
85 90 95

Leu Trp Asn Leu His Gly Gln Ala Leu Tyr Leu Gly Ile Val Leu Phe
100 105 110

Ile Phe Gly Cys Leu Leu Val Leu Gly Leu Trp Ile Tyr Leu Leu Glu
115 120 125

Ile Leu Trp Arg Leu Gly Ala Thr Ile Trp Gln Leu Leu Ala Phe Phe
130 135 140

Leu Ala Phe Phe Leu Asp Ile Ile Leu Leu Ile Ile Ala Leu Tyr Leu
145 150 155 160

Gln Gln Asn Trp Trp Thr Leu Leu Val Asp Leu Leu Trp Leu Leu Leu
165 170 175

Phe Leu Ala Ile Leu Ile Trp Met Tyr Tyr His Gly Gln Arg Met Thr
180 185 190

Phe Ala Glu Asp Lys Thr Tyr Lys Tyr Ile Arg Asp Asn His Ser Lys
195 200 205

Phe Cys Cys Val Asp Val Leu Glu Ile Leu Pro Tyr Leu Ser Cys Leu
210 215 220

Thr Ala Ser Asp Gln Asp Arg Leu Arg Ala Ser Tyr Arg Gln Ile Gly
225 230 235 240

Asn Arg Asp Thr Leu Trp Gly Leu Phe Asn Asn Leu Gln Arg Arg Pro
245 250 255

Gly Trp Val Glu Val Phe Ile Arg Ala Leu Gln Ile Cys Glu Leu Pro
260 265 270

Gly Leu Ala Asp Gln Val Thr Arg Val Tyr Gln Ser Tyr Leu Pro Pro
275 280 285

Gly Thr Ser Leu Arg Ser Leu Glu Pro Leu Gln Leu Pro Asp Phe Pro
290 295 300

Ala Ala Val Ser Gly Pro Ser Ala Phe Ala Pro Gly His Asn Ile Pro
305 310 315 320

Asp His Gly Leu Arg Glu Thr Pro Ser Cys Pro Lys Pro Val Gln Asp
325 330 335

```
Thr Gln Pro Pro Glu Ser Pro Val Glu Asn Ser Glu Gln Leu Leu Gln
            340                 345                 350

Thr Asn Ser Gly Ala Val Ala Arg Met Ser Gly Gly Ser Leu Ile Pro
        355                 360                 365

Ser Pro Asn Gln Gln Ala Leu Ser Pro Gln Pro Ser Arg Glu His Gln
    370                 375                 380

Glu Gln Glu Pro Glu Leu Gly Gly Ala His Ala Ala Asn Val Ala Ser
385                 390                 395                 400

Val Pro Ile Ala Thr Tyr Gly Pro Val Ser Pro Thr Val Ser Phe Gln
                405                 410                 415

Pro Leu Pro Arg Thr Ala Leu Arg Thr Asn Leu Leu Ser Gly Val Thr
            420                 425                 430

Val Ser Ala Leu Ser Ala Asp Thr Ser Leu Ser Ser Ser Ser Thr Gly
        435                 440                 445

Ser Ala Phe Ala Lys Gly Ala Gly Asp Gln Ala Lys Ala Ala Thr Cys
    450                 455                 460

Phe Ser Thr Thr Leu Thr Asn Ser Val Thr Thr Ser Ser Val Pro Ser
465                 470                 475                 480

Pro Arg Leu Val Pro Val Lys Thr Met Ser Ser Lys Leu Pro Leu Ser
                485                 490                 495

Ser Lys Ser Thr Ala Ala Met Thr Ser Thr Val Leu Thr Asn Thr Ala
            500                 505                 510

Pro Ser Lys Leu Pro Ser Asn Ser Val Tyr Ala Gly Thr Val Pro Ser
        515                 520                 525

Arg Val Pro Ala Ser Val Ala Lys Ala Pro Ala Asn Thr Ile Pro Pro
    530                 535                 540

Glu Arg Asn Ser Lys Gln Ala Lys Glu Thr Pro Glu Gly Pro Ala Thr
545                 550                 555                 560

Lys Val Thr Thr Gly Gly Asn Gln Thr Gly Pro Asn Ser Ser Ile Arg
                565                 570                 575

Ser Leu His Ser Gly Pro Glu Met Ser Lys Pro Gly Val Leu Val Ser
            580                 585                 590

Gln Leu Asp Glu Pro Phe Ser Ala Cys Ser Val Asp Leu Ala Ile Ser
        595                 600                 605

Pro Ser Ser Ser Leu Val Ser Glu Pro Asn His Gly Pro Glu Glu Asn
    610                 615                 620

Glu Tyr Ser Ser Phe Arg Ile Gln Val Asp Glu Ser Pro Ser Ala Asp
625                 630                 635                 640

Leu Leu Gly Ser Pro Glu Pro Leu Ala Thr Gln Gln Pro Gln Glu Glu
                645                 650                 655

Glu Glu His Cys Ala Ser Ser Met Pro Trp Ala Lys Trp Leu Gly Ala
            660                 665                 670

Thr Ser Ala Leu Leu Ala Val Phe Leu Ala Val Met Leu Tyr Arg Ser
        675                 680                 685

Arg Arg Leu Ala Gln
    690
```

<210> SEQ ID NO 11
<211> LENGTH: 912
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature -continued
<223> OTHER INFORMATION: Epstein Barr Virus latent membrane protein 1
(without the cytoplasmic domain) fused to the cytoplasmic domain
of human CD3 zeta chain

<400> SEQUENCE: 11

```
atggaacacg accttgagag gggcccaccg ggcccgcgac ggcccccctcg aggacccccc     60

ctctcctctt ccctaggcct tgctctcctt ctcctcctct tggcgctact gttttggctg    120

tacatcgtta tgagtgactg gactggagga gccctccttg tcctctattc ctttgctctc    180

atgcttataa ttataatttt gatcatcttt atcttcagaa gagaccttct ctgtccactt    240

ggagcccttt gtatactcct actgatgatc accctcctgc tcatcgctct ctggaatttg    300

cacggacagg cattgttcct tggaattgtg ctgttcatct tcgggtgctt acttgtctta    360

ggtatctgga tctacttatt ggagatgctc tggcgacttg gtgccaccat ctggcagctt    420

ttggccttct tcctagcctt cttcctagac ctcatcctgc tcattattgc tctctatcta    480

caacaaaact ggtggactct attggttgat ctcctttggc tcctcctgtt tctggcgatt    540

ttaatctgga tgtattacca tggacaacga agagtgaagt tcagcaggag cgcagacgcc    600

cccgcgtacc agcagggcca gaaccagctc tataacgagc tcaatctagg acgaagagag    660

gagtacgatg ttttggacaa gagacgtggc cgggaccctg agatgggggg aaagccgcag    720

agaaggaaga accctcagga aggcctgtac aatgaactgc agaaagataa gatggcggag    780

gcctacagtg agattgggat gaaaggcgag cgccggaggg gcaaggggca cgatggcctt    840

taccagggtc tcagtacagc caccaaggac acctacgacg cccttcacat gcaggccctg    900

ccccctcgct aa                                                        912
```

<210> SEQ ID NO 12
<211> LENGTH: 303
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1
(without the cytoplasmic domain) fused to the cytoplasmic domain
of human CD3 zeta chain

<400> SEQUENCE: 12

```
Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
            20                  25                  30

Leu Leu Ala Leu Leu Phe Trp Leu Tyr Ile Val Met Ser Asp Trp Thr
        35                  40                  45

Gly Gly Ala Leu Leu Val Leu Tyr Ser Phe Ala Leu Met Leu Ile Ile
    50                  55                  60

Ile Ile Leu Ile Ile Phe Ile Phe Arg Arg Asp Leu Leu Cys Pro Leu
65                  70                  75                  80

Gly Ala Leu Cys Ile Leu Leu Leu Met Ile Thr Leu Leu Leu Ile Ala
                85                  90                  95

Leu Trp Asn Leu His Gly Gln Ala Leu Phe Leu Gly Ile Val Leu Phe
            100                 105                 110

Ile Phe Gly Cys Leu Leu Val Leu Gly Ile Trp Ile Tyr Leu Leu Glu
        115                 120                 125

Met Leu Trp Arg Leu Gly Ala Thr Ile Trp Gln Leu Leu Ala Phe Phe
    130                 135                 140
```

```
Leu Ala Phe Phe Leu Asp Leu Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Arg Val
            180                 185                 190

Lys Phe Ser Arg Ser Ala Asp Ala Pro Ala Tyr Gln Gln Gly Gln Asn
        195                 200                 205

Gln Leu Tyr Asn Glu Leu Asn Leu Gly Arg Arg Glu Glu Tyr Asp Val
    210                 215                 220

Leu Asp Lys Arg Arg Gly Arg Asp Pro Glu Met Gly Gly Lys Pro Gln
225                 230                 235                 240

Arg Arg Lys Asn Pro Gln Glu Gly Leu Tyr Asn Glu Leu Gln Lys Asp
                245                 250                 255

Lys Met Ala Glu Ala Tyr Ser Glu Ile Gly Met Lys Gly Glu Arg Arg
            260                 265                 270

Arg Gly Lys Gly His Asp Gly Leu Tyr Gln Gly Leu Ser Thr Ala Thr
        275                 280                 285

Lys Asp Thr Tyr Asp Ala Leu His Met Gln Ala Leu Pro Pro Arg
    290                 295                 300
```

<210> SEQ ID NO 13
<211> LENGTH: 3775
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Influenza NP protein co-expressed by use of an IRES sequence with Epstein Barr Virus latent membrane protein 1 (without the cytoplasmic domain) fused to murine MyD88 and the cytoplasmic domain of murine CD40 as a single 3-protein chimera

<400> SEQUENCE: 13

```
atggcgtctc aaggcaccaa acgatcttac gaacagatgg agactgatgg agaacgccag     60

aatgccactg aaatcagagc atccgtcgga aaaatgattg gtggaattgg acgattctac    120

atccaaatgt gcaccgaact caaactcagt gattatgagg gacggttgat ccaaaacagc    180

ttaacaatag agagaatggt gctctctgct tttgacgaaa ggagaaataa ataccttgaa    240

gaacatccca gtgcggggaa agatcctaag aaaactggag gacctatata caggagagta    300

aacggaaagt ggatgagaga actcatcctt tatgacaaag aagaaataag gcgaatctgg    360

cgccaagcta ataatggtga cgatgcaacg gctggtctga ctcacatgat gatctggcat    420

tccaatttga atgatgcaac ttatcagagg acaagagctc ttgttcgcac cggaatggat    480

cccaggatgt gctctctgat gcaaggttca actctcccta ggaggtctgg agccgcaggt    540

gctgcagtca aaggagttgg aacaatggtg atggaattgg tcagaatgat caaacgtggg    600

atcaatgatc ggaacttctg gaggggtgag aatggacgaa aaacaagaat tgcttatgaa    660

agaatgtgca acattctcaa agggaaattt caaactgctg cacaaaaagc aatgatggat    720

caagtgagag agagccggaa cccagggaat gctgagttcg aagatctcac ttttctagca    780

cggtctgcac tcatattgag agggtcggtt gctcacaagt cctgcctgcc tgcctgtgtg    840

tatggacctg ccgtagccag tgggtacgac tttgaaaggg agggatactc tctagtcgga    900

atagaccctt tcagactgct tcaaaacagc caagtgtaca gcctaatcag accaaatgag    960
```

-continued aatccagcac acaagagtca actggtgtgg atggcatgcc attctgccgc atttgaagat 1020
ctaagagtat taagcttcat caaagggacg aaggtgctcc caagagggaa gctttccact 1080
agaggagttc aaattgcttc caatgaaaat atggagacta tggaatcaag tacacttgaa 1140
ctgagaagca ggtactgggc cataaggacc agaagtggag gaaacaccaa tcaacagagg 1200
gcatctgcgg gccaaatcag catacaacct acgttctcag tacagagaaa tctccctttt 1260
gacagaacaa ccattatggc agcattcaat gggaatacag aggggagaac atctgacatg 1320
aggaccgaaa tcataaggat gatggaaagt gcaagaccag aagatgtgtc tttccagggg 1380
cggggagtct tcgagctctc ggacgaaaag gcagcgagcc cgatcgtgcc ttcctttgac 1440
atgagtaatg aaggatctta tttcttcgga gacaatgcag aggagtacga caattaagcc 1500
cctctccctc cccccccct aacgttactg gccgaagccg cttggaataa ggccggtgtg 1560
tgtttgtcta tatgtgattt tccaccatat tgccgtcttt tggcaatgtg agggcccgga 1620
aacctggccc tgtcttcttg acgagcattc ctaggggtct ttcccctctc gccaaaggaa 1680
tgcaaggtct gttgaatgtc gtgaaggaag cagttcctct ggaagcttct tgaagacaaa 1740
caacgtctgt agcgaccctt tgcaggcagc ggaacccccc acctggcgac aggtgcctct 1800
gcggccaaaa gccacgtgta taagatacac ctgcaaaggc ggcacaaccc cagtgccacg 1860
ttgtgagttg gatagttgtg gaaagagtca aatggctctc ctcaagcgta gtcaacaagg 1920
ggctgaagga tgcccagaag gtaccccatt gtatgggaat ctgatctggg gcctcggtgc 1980
acatgcttta catgtgttta gtcgaggtta aaaaagctct aggccccccg aaccacgggg 2040
acgtggtttt cctttgaaaa acacgatgat aagcttgcca caaatggaac acgaccttga 2100
gaggggccca ccgggcccgc gacggccccc tcgaggaccc cccctctcct cttccctagg 2160
ccttgctctc cttctcctcc tcttggcgct actgttttgg ctgtacatcg ttatgagtga 2220
ctggactgga ggagccctcc ttgtcctcta ttcctttgct ctcatgctta taattataat 2280
tttgatcatc tttatcttca gaagagacct tctctgtcca cttggagccc tttgtatact 2340
cctactgatg atcaccctcc tgctcatcgc tctctggaat ttgcacggac aggcattgtt 2400
ccttggaatt gtgctgttca tcttcgggtg cttacttgtc ttaggtatct ggatctactt 2460
attggagatg ctctggcgac ttggtgccac catctggcag cttttggcct tcttcctagc 2520
cttcttccta gacctcatcc tgctcattat tgctctctat ctacaacaaa actggtggac 2580
tctattggtt gatctccttt ggctcctcct gtttctggcg attttaatct ggatgtatta 2640
ccatggacaa cgaatgtctg cgggagaccc ccgcgtggga tccgggtccc tggactcctt 2700
catgttctcc ataccccttgg tcgcgcttaa cgtgggagtg aggcgccgcc tatcgctgtt 2760
cttgaaccct cggacgcccg tggcggccga ctggaccttg ctggcggagg agatgggctt 2820
cgagtacttg gagatccgag agctggaaac gcgccctgac cccactcgca gtttgttgga 2880
tgcctggcag gggcgctctg gcgcgtctgt cggcaggctg ctagagctgc tggccttgtt 2940
agaccgtgag gatatactga aggagctgaa gtcgcgcatc gaggaggact gccagaaata 3000
cttaggtaag cagcagaacc aggagtccga gaagccttta caggtggcca gagtggaaag 3060
cagtgtccca caaacaaagg aactgggagg catcaccacc cttgatgacc ccctaggaca 3120
aacgccggaa cttttcgatg cctttatctg ctactgcccc aacgatatcg agtttgtgca 3180
ggagatgatc cggcaactag aacagacaga ctatcggctt aagttgtgtg tgtccgaccg 3240
tgacgtcctg ccgggcacct gtgtctggtc cattgccagc gagctaattg agaaaaggtg 3300
tcgccgcatg gtggtggttg tttctgacga ttatctacag agcaaggaat gtgacttcca 3360

-continued

```
gaccaagttt gcactcagcc tgtctccagg tgtccaacag aagcgactga ttcctattaa   3420

atacaaggcg atgaagaagg actttcccag tatcctgcgg ttcatcacta tatgcgacta   3480

taccaaccct tgcaccaagt cctggttctg gacccgcctt gccaaggctt tgtccctggt   3540

cgagtatatc aaaaaggtgg tcaagaaacc aaaggataat gagatcttac cccctgcggc   3600

tcgacggcaa gatccccagg agatggaaga ttatcccggt cataacaccg ctgctccagt   3660

gcaggagacg ctgcacgggt gtcagcctgt cacacaggag gatggtaaag agagtcgcat   3720

ctcagtgcag gagcggcagg tgacagacag catagccttg aggcccctgg tctga        3775


<210> SEQ ID NO 14
<211> LENGTH: 498
<212> TYPE: PRT
<213> ORGANISM: Influenza virus
<220> FEATURE:
<221> NAME/KEY: misc_feature
<223> OTHER INFORMATION: Nuclear Protein (NP)

<400> SEQUENCE: 14

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285
```

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 15
<211> LENGTH: 563
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1
      (without the cytoplasmic domain) fused to the murine protein MyD88
      fused to the cytoplasmic domain of murine CD40

<400> SEQUENCE: 15

Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
            20                  25                  30

Leu Leu Ala Leu Leu Phe Trp Leu Tyr Ile Val Met Ser Asp Trp Thr
        35                  40                  45

Gly Gly Ala Leu Leu Val Leu Tyr Ser Phe Ala Leu Met Leu Ile Ile
    50                  55                  60

Ile Ile Leu Ile Ile Phe Ile Phe Arg Arg Asp Leu Leu Cys Pro Leu
65                  70                  75                  80

Gly Ala Leu Cys Ile Leu Leu Leu Met Ile Thr Leu Leu Leu Ile Ala
                85                  90                  95

Leu Trp Asn Leu His Gly Gln Ala Leu Phe Leu Gly Ile Val Leu Phe
            100                 105                 110

Ile Phe Gly Cys Leu Leu Val Leu Gly Ile Trp Ile Tyr Leu Leu Glu

-continued

```
        115                 120                 125

Met Leu Trp Arg Leu Gly Ala Thr Ile Trp Gln Leu Leu Ala Phe Phe
    130                 135                 140

Leu Ala Phe Phe Leu Asp Leu Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Met Ser
            180                 185                 190

Ala Gly Asp Pro Arg Val Gly Ser Gly Ser Leu Asp Ser Phe Met Phe
        195                 200                 205

Ser Ile Pro Leu Val Ala Leu Asn Val Gly Val Arg Arg Arg Leu Ser
    210                 215                 220

Leu Phe Leu Asn Pro Arg Thr Pro Val Ala Ala Asp Trp Thr Leu Leu
225                 230                 235                 240

Ala Glu Glu Met Gly Phe Glu Tyr Leu Glu Ile Arg Glu Leu Glu Thr
                245                 250                 255

Arg Pro Asp Pro Thr Arg Ser Leu Leu Asp Ala Trp Gln Gly Arg Ser
            260                 265                 270

Gly Ala Ser Val Gly Arg Leu Leu Glu Leu Leu Ala Leu Leu Asp Arg
        275                 280                 285

Glu Asp Ile Leu Lys Glu Leu Lys Ser Arg Ile Glu Glu Asp Cys Gln
    290                 295                 300

Lys Tyr Leu Gly Lys Gln Gln Asn Gln Glu Ser Glu Lys Pro Leu Gln
305                 310                 315                 320

Val Ala Arg Val Glu Ser Ser Val Pro Gln Thr Lys Glu Leu Gly Gly
                325                 330                 335

Ile Thr Thr Leu Asp Asp Pro Leu Gly Gln Thr Pro Glu Leu Phe Asp
            340                 345                 350

Ala Phe Ile Cys Tyr Cys Pro Asn Asp Ile Glu Phe Val Gln Glu Met
        355                 360                 365

Ile Arg Gln Leu Glu Gln Thr Asp Tyr Arg Leu Lys Leu Cys Val Ser
    370                 375                 380

Asp Arg Asp Val Leu Pro Gly Thr Cys Val Trp Ser Ile Ala Ser Glu
385                 390                 395                 400

Leu Ile Glu Lys Arg Cys Arg Arg Met Val Val Val Val Ser Asp Asp
                405                 410                 415

Tyr Leu Gln Ser Lys Glu Cys Asp Phe Gln Thr Lys Phe Ala Leu Ser
            420                 425                 430

Leu Ser Pro Gly Val Gln Gln Lys Arg Leu Ile Pro Ile Lys Tyr Lys
        435                 440                 445

Ala Met Lys Lys Asp Phe Pro Ser Ile Leu Arg Phe Ile Thr Ile Cys
    450                 455                 460

Asp Tyr Thr Asn Pro Cys Thr Lys Ser Trp Phe Trp Thr Arg Leu Ala
465                 470                 475                 480

Lys Ala Leu Ser Leu Val Glu Tyr Ile Lys Lys Val Val Lys Lys Pro
                485                 490                 495

Lys Asp Asn Glu Ile Leu Pro Pro Ala Ala Arg Arg Gln Asp Pro Gln
            500                 505                 510

Glu Met Glu Asp Tyr Pro Gly His Asn Thr Ala Ala Pro Val Gln Glu
        515                 520                 525

Thr Leu His Gly Cys Gln Pro Val Thr Gln Glu Asp Gly Lys Glu Ser
    530                 535                 540
```

```
Arg Ile Ser Val Gln Glu Arg Gln Val Thr Asp Ser Ile Ala Leu Arg
545                 550                 555                 560

Pro Leu Val


<210> SEQ ID NO 16
<211> LENGTH: 1692
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Epstein Barr Virus latent membrane protein 1
      (without the cytoplasmic domain) fused to murine MyD88 and the
      cytoplasmic domain of murine CD40 as a single 3-protein chimera

<400> SEQUENCE: 16

atggaacacg accttgagag gggcccaccg ggcccgcgac ggcccccctcg aggacccccc     60

ctctcctctt ccctaggcct tgctctcctt ctcctcctct tggcgctact gttttggctg    120

tacatcgtta tgagtgactg gactggagga gccctccttg tcctctattc ctttgctctc    180

atgcttataa ttataatttt gatcatcttt atcttcagaa gagaccttct ctgtccactt    240

ggagcccttt gtatactcct actgatgatc accctcctgc tcatcgctct ctggaatttg    300

cacggacagg cattgttcct tggaattgtg ctgttcatct tcgggtgctt acttgtctta    360

ggtatctgga tctacttatt ggagatgctc tggcgacttg gtgccaccat ctggcagctt    420

ttggccttct tcctagcctt cttcctagac ctcatcctgc tcattattgc tctctatcta    480

caacaaaact ggtggactct attggttgat ctcctttggc tcctcctgtt tctggcgatt    540

ttaatctgga tgtattacca tggacaacga atgtctgcgg gagacccccg cgtgggatcc    600

gggtccctgg actccttcat gttctccata cccttggtcg cgcttaacgt gggagtgagg    660

cgccgcctat cgctgttctt gaaccctcgg acgcccgtgg cggccgactg gaccttgctg    720

gcggaggaga tgggcttcga gtacttggag atccgagagc tggaaacgcg ccctgacccc    780

actcgcagtt tgttggatgc ctggcagggg cgctctggcg cgtctgtcgg caggctgcta    840

gagctgctgg ccttgttaga ccgtgaggat atactgaagg agctgaagtc gcgcatcgag    900

gaggactgcc agaaatactt aggtaagcag cagaaccagg agtccgagaa gcctttacag    960

gtggccagag tggaaagcag tgtcccacaa acaaaggaac tgggaggcat caccaccctt   1020

gatgaccccc taggacaaac gccggaactt ttcgatgcct ttatctgcta ctgccccaac   1080

gatatcgagt ttgtgcagga gatgatccgg caactagaac agacagacta tcggcttaag   1140

ttgtgtgtgt ccgaccgtga cgtcctgccg ggcacctgtg tctggtccat tgccagcgag   1200

ctaattgaga aaaggtgtcg ccgcatggtg gtggttgttt ctgacgatta tctacagagc   1260

aaggaatgtg acttccagac caagtttgca ctcagcctgt ctccaggtgt ccaacagaag   1320

cgactgattc ctattaaata caaggcgatg aagaaggact ttcccagtat cctgcggttc   1380

atcactatat gcgactatac caacccttgc accaagtcct ggttctggac ccgccttgcc   1440

aaggctttgt ccctggtcga gtatatcaaa aaggtggtca agaaaccaaa ggataatgag   1500

atcttacccc ctgcggctcg acggcaagat ccccaggaga tggaagatta tcccggtcat   1560

aacaccgctg ctccagtgca ggagacgctg cacgggtgtc agcctgtcac acaggaggat   1620

ggtaaagaga gtcgcatctc agtgcaggag cggcaggtga cagacagcat agccttgagg   1680

cccctggtct ga                                                       1692
```

```
<210> SEQ ID NO 17
<211> LENGTH: 563
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1
      (without the cytoplasmic domain) fused to the murine protein MyD88
      fused to the cytoplasmic domain of murine CD40

<400> SEQUENCE: 17

Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
            20                  25                  30

Leu Leu Ala Leu Leu Phe Trp Leu Tyr Ile Val Met Ser Asp Trp Thr
        35                  40                  45

Gly Gly Ala Leu Leu Val Leu Tyr Ser Phe Ala Leu Met Leu Ile Ile
    50                  55                  60

Ile Ile Leu Ile Ile Phe Ile Phe Arg Arg Asp Leu Leu Cys Pro Leu
65                  70                  75                  80

Gly Ala Leu Cys Ile Leu Leu Leu Met Ile Thr Leu Leu Leu Ile Ala
                85                  90                  95

Leu Trp Asn Leu His Gly Gln Ala Leu Phe Leu Gly Ile Val Leu Phe
            100                 105                 110

Ile Phe Gly Cys Leu Leu Val Leu Gly Ile Trp Ile Tyr Leu Leu Glu
        115                 120                 125

Met Leu Trp Arg Leu Gly Ala Thr Ile Trp Gln Leu Leu Ala Phe Phe
    130                 135                 140

Leu Ala Phe Phe Leu Asp Leu Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Met Ser
            180                 185                 190

Ala Gly Asp Pro Arg Val Gly Ser Gly Ser Leu Asp Ser Phe Met Phe
        195                 200                 205

Ser Ile Pro Leu Val Ala Leu Asn Val Gly Val Arg Arg Arg Leu Ser
    210                 215                 220

Leu Phe Leu Asn Pro Arg Thr Pro Val Ala Ala Asp Trp Thr Leu Leu
225                 230                 235                 240

Ala Glu Glu Met Gly Phe Glu Tyr Leu Glu Ile Arg Glu Leu Glu Thr
                245                 250                 255

Arg Pro Asp Pro Thr Arg Ser Leu Leu Asp Ala Trp Gln Gly Arg Ser
            260                 265                 270

Gly Ala Ser Val Gly Arg Leu Leu Glu Leu Leu Ala Leu Leu Asp Arg
        275                 280                 285

Glu Asp Ile Leu Lys Glu Leu Lys Ser Arg Ile Glu Glu Asp Cys Gln
    290                 295                 300

Lys Tyr Leu Gly Lys Gln Gln Asn Gln Glu Ser Glu Lys Pro Leu Gln
305                 310                 315                 320

Val Ala Arg Val Glu Ser Ser Val Pro Gln Thr Lys Glu Leu Gly Gly
                325                 330                 335

Ile Thr Thr Leu Asp Asp Pro Leu Gly Gln Thr Pro Glu Leu Phe Asp
```

```
            340                 345                 350

Ala Phe Ile Cys Tyr Cys Pro Asn Asp Ile Glu Phe Val Gln Glu Met
        355                 360                 365

Ile Arg Gln Leu Glu Gln Thr Asp Tyr Arg Leu Lys Leu Cys Val Ser
    370                 375                 380

Asp Arg Asp Val Leu Pro Gly Thr Cys Val Trp Ser Ile Ala Ser Glu
385                 390                 395                 400

Leu Ile Glu Lys Arg Cys Arg Arg Met Val Val Val Val Ser Asp Asp
                405                 410                 415

Tyr Leu Gln Ser Lys Glu Cys Asp Phe Gln Thr Lys Phe Ala Leu Ser
            420                 425                 430

Leu Ser Pro Gly Val Gln Gln Lys Arg Leu Ile Pro Ile Lys Tyr Lys
        435                 440                 445

Ala Met Lys Lys Asp Phe Pro Ser Ile Leu Arg Phe Ile Thr Ile Cys
    450                 455                 460

Asp Tyr Thr Asn Pro Cys Thr Lys Ser Trp Phe Trp Thr Arg Leu Ala
465                 470                 475                 480

Lys Ala Leu Ser Leu Val Glu Tyr Ile Lys Lys Val Val Lys Lys Pro
                485                 490                 495

Lys Asp Asn Glu Ile Leu Pro Pro Ala Ala Arg Arg Gln Asp Pro Gln
            500                 505                 510

Glu Met Glu Asp Tyr Pro Gly His Asn Thr Ala Ala Pro Val Gln Glu
        515                 520                 525

Thr Leu His Gly Cys Gln Pro Val Thr Gln Glu Asp Gly Lys Glu Ser
    530                 535                 540

Arg Ile Ser Val Gln Glu Arg Gln Val Thr Asp Ser Ile Ala Leu Arg
545                 550                 555                 560

Pro Leu Val
```

<210> SEQ ID NO 18
<211> LENGTH: 3348
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Epstein Barr Virus latent membrane protein 1 (without the cytoplasmic domain) fused to human IPS-1, the cytoplasmic domain of human TLR7, and the cytoplasmic domain (CD) of Epstein Barr Virus LMP1 as a single chimera

<400> SEQUENCE: 18

```
atggaacacg accttgagag gggcccaccg ggcccgcgac ggccccctcg aggaccccc      60

ctctcctctt ccctaggcct tgctctcctt ctcctcctct tggcgctact gttttggctg    120

tacatcgtta tgagtgactg gactggagga gccctccttg tcctctattc ctttgctctc    180

atgcttataa ttataatttt gatcatcttt atcttcagaa gagaccttct ctgtccactt    240

ggagcccttt gtatactcct actgatgatc accctcctgc tcatcgctct ctggaatttg    300

cacggacagg cattgttcct tggaattgtg ctgttcatct tcgggtgctt acttgtctta    360

ggtatctgga tctacttatt ggagatgctc tggcgacttg gtgccaccat ctggcagctt    420

ttggccttct tcctagcctt cttcctagac ctcatcctgc tcattattgc tctctatcta    480

caacaaaact ggtggactct attggttgat ctcctttggc tcctcctgtt tctggcgatt    540

ttaatctgga tgtattacca tggacaacga atgccgtttg ctgaagacaa gacctataag    600
```

-continued

```
tatatctgcc gcaatttcag caatttttgc aatgtggatg ttgtagagat tctgccttac    660
ctgccctgcc tcacagcaag agaccaggat cgactgcggg ccacctgcac actctcaggg    720
aaccgggaca ccctctggca tctcttcaat acccttcagc ggcggcccgg ctgggtggag    780
tacttcattg cggcactgag ggctgtgag ctagttgatc tcgcggacga agtggcctct    840
gtctaccaga gctaccagcc tcggacctcg gaccgtcccc cagacccact ggagccaccg    900
tcacttcctg ctgagaggcc agggcccccc acacctgctg cggcccacag catcccctac    960
aacagctgca gagagaagga gccaagttac cccatgcctg tccaggagac ccaggcgcca   1020
gagtccccag gagagaattc agagcaagcc ctgcagacgc tcagccccag agccatccca   1080
aggaatccag atggtggccc cctggagtcc tcctctgatc tggcagccct cagccctctg   1140
acctccagcg ggcatcagga gcaggacaca gaactgggca gtacccacac agcaggtgcg   1200
acctccagcc tcacaccatc ccgtgggcct gtgtctccat ctgtctcctt ccagcccctg   1260
gcccgttcca cccccagggc aagccgcttg cctggaccca cagggtcagt tgtatctact   1320
ggcacctcct tctcctcctc atcccctggc ttggcctctg caggggctgc agagggtaaa   1380
cagggtgcag agagtgacca ggccgagcct atcatctgct ccagtggggc agaggcacct   1440
gccaactctc tgccctccaa agtgcctacc accttgatgc ctgtgaacac agtggccctg   1500
aaagtgcctg ccaacccagc atctgtcagc acagtgccct ccaagttgcc aactagctca   1560
aagcccctg gtgcagtgcc ttctaatgcg ctcaccaatc cagcaccatc caaattgccc   1620
atcaactcaa cccgtgctgg catggtgcca tccaaagtgc ctactagcat ggtgctcacc   1680
aaggtgtctg ccagcacagt ccccactgac gggagcagca gaaatgagga gaccccagca   1740
gctccaacac ccgccggcgc cactggaggc agctcagcct ggctagacag cagctctgag   1800
aataggggcc ttgggtcgga gctgagtaag cctggcgtgc tggcatccca ggtagacagc   1860
ccgttctcgg gctgcttcga ggatcttgcc atcagtgcca gcacctcctt gggcatgggg   1920
ccctgccatg gcccagagga gaatgagtat aagtccgagg gcacctttgg gatccacgtg   1980
gctgagaacc ccagcatcca gctcctggag ggcaaccctg ggccacctgc ggacccggat   2040
ggcggcccca ggccacaagc cgaccggaag ttccaggaga gggaggtgcc atgccacagg   2100
ccctcacctg gggctctgtg gctccaggtg gctgtgacag ggtgctggt agtcacactc   2160
ctggtggtgc tgtaccggcg gcgtctgcac cacctctatt tctgggatgt gtggtatatt   2220
taccatttct gtaaggccaa gataaagggg tatcagcgtc taatatcacc agactgttgc   2280
tatgatgctt ttattgtgta tgacactaaa gacccagctg tgaccgagtg ggttttggct   2340
gagctggtgg ccaaactgga agacccaaga gagaaacatt ttaatttatg tctcgaggaa   2400
agggactggt taccagggca gccagttctg gaaaaccttt cccagagcat acagcttagc   2460
aaaaagacag tgtttgtgat gacagacaag tatgcaaaga ctgaaaattt taagatagca   2520
ttttacttgt cccatcagag gctcatggat gaaaaagttg atgtgattat cttgatattt   2580
cttgagaagc cctttcagaa gtccaagttc ctccagctcc ggaaaaggct ctgtgggagt   2640
tctgtccttg agtggccaac aaacccgcaa gctcacccat acttctggca gtgtctaaag   2700
aacgccctgg ccacagacaa tcatgtggcc tatagtcagg tgttcaagga aacggtccac   2760
agtgatgaac accaccacga tgactccctc ccgcaccctc aacaagctac cgatgattct   2820
ggccatgaat ctgactctaa ctccaacgag ggcagacacc acctgctcgt gagtggagcc   2880
ggcgacggac ccccactctg ctctcaaaac ctaggcgcac ctggaggtgg tcctgacaat   2940
ggcccacagg accctgacaa cactgatgac aatggcccac aggaccctga caacactgat   3000
```

```
gacaatggcc cacatgaccc gctgcctcag gaccctgaca acactgatga caatggccca   3060

caggaccctg acaacactga tgacaatggc ccacatgacc cgctgcctca tagccctagc   3120

gactctgctg gaaatgatgg aggccctcca caattgacgg aagaggttga aaacaaagga   3180

ggtgaccagg gcccgccttt gatgacagac ggaggcggcg gtcatagtca tgattccggc   3240

catggcggcg gtgatccaca ccttcctacg ctgcttttgg gttcttctgg ttccggtgga   3300

gatgatgacg acccccacgg cccagttcag ctaagctact atgactaa                3348


<210> SEQ ID NO 19
<211> LENGTH: 1115
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Epstein Barr Virus latent membrane protein 1
      (without the cytoplasmic domain) fused to the human IPS-1 fused to
      the cytoplasmic domain of human TLR7 fused to the cytoplasmic
      domain of Epstein Barr Virus latent membrane protein 1

<400> SEQUENCE: 19

Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
            20                  25                  30

Leu Leu Ala Leu Leu Phe Trp Leu Tyr Ile Val Met Ser Asp Trp Thr
        35                  40                  45

Gly Gly Ala Leu Leu Val Leu Tyr Ser Phe Ala Leu Met Leu Ile Ile
    50                  55                  60

Ile Ile Leu Ile Ile Phe Ile Phe Arg Arg Asp Leu Leu Cys Pro Leu
65                  70                  75                  80

Gly Ala Leu Cys Ile Leu Leu Leu Met Ile Thr Leu Leu Leu Ile Ala
                85                  90                  95

Leu Trp Asn Leu His Gly Gln Ala Leu Phe Leu Gly Ile Val Leu Phe
            100                 105                 110

Ile Phe Gly Cys Leu Leu Val Leu Gly Ile Trp Ile Tyr Leu Leu Glu
        115                 120                 125

Met Leu Trp Arg Leu Gly Ala Thr Ile Trp Gln Leu Leu Ala Phe Phe
    130                 135                 140

Leu Ala Phe Phe Leu Asp Leu Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Met Pro
            180                 185                 190

Phe Ala Glu Asp Lys Thr Tyr Lys Tyr Ile Cys Arg Asn Phe Ser Asn
        195                 200                 205

Phe Cys Asn Val Asp Val Val Glu Ile Leu Pro Tyr Leu Pro Cys Leu
    210                 215                 220

Thr Ala Arg Asp Gln Asp Arg Leu Arg Ala Thr Cys Thr Leu Ser Gly
225                 230                 235                 240

Asn Arg Asp Thr Leu Trp His Leu Phe Asn Thr Leu Gln Arg Arg Pro
                245                 250                 255

Gly Trp Val Glu Tyr Phe Ile Ala Ala Leu Arg Gly Cys Glu Leu Val
            260                 265                 270
```

-continued

```
Asp Leu Ala Asp Glu Val Ala Ser Val Tyr Gln Ser Tyr Gln Pro Arg
        275                 280                 285

Thr Ser Asp Arg Pro Pro Asp Pro Leu Glu Pro Pro Ser Leu Pro Ala
    290                 295                 300

Glu Arg Pro Gly Pro Pro Thr Pro Ala Ala Ala His Ser Ile Pro Tyr
305                 310                 315                 320

Asn Ser Cys Arg Glu Lys Glu Pro Ser Tyr Pro Met Pro Val Gln Glu
                325                 330                 335

Thr Gln Ala Pro Glu Ser Pro Gly Glu Asn Ser Glu Gln Ala Leu Gln
            340                 345                 350

Thr Leu Ser Pro Arg Ala Ile Pro Arg Asn Pro Asp Gly Gly Pro Leu
        355                 360                 365

Glu Ser Ser Ser Asp Leu Ala Ala Leu Ser Pro Leu Thr Ser Ser Gly
    370                 375                 380

His Gln Glu Gln Asp Thr Glu Leu Gly Ser Thr His Thr Ala Gly Ala
385                 390                 395                 400

Thr Ser Ser Leu Thr Pro Ser Arg Gly Pro Val Ser Pro Ser Val Ser
                405                 410                 415

Phe Gln Pro Leu Ala Arg Ser Thr Pro Arg Ala Ser Arg Leu Pro Gly
            420                 425                 430

Pro Thr Gly Ser Val Val Ser Thr Gly Thr Ser Phe Ser Ser Ser Ser
        435                 440                 445

Pro Gly Leu Ala Ser Ala Gly Ala Ala Glu Gly Lys Gln Gly Ala Glu
    450                 455                 460

Ser Asp Gln Ala Glu Pro Ile Ile Cys Ser Ser Gly Ala Glu Ala Pro
465                 470                 475                 480

Ala Asn Ser Leu Pro Ser Lys Val Pro Thr Thr Leu Met Pro Val Asn
                485                 490                 495

Thr Val Ala Leu Lys Val Pro Ala Asn Pro Ala Ser Val Ser Thr Val
            500                 505                 510

Pro Ser Lys Leu Pro Thr Ser Ser Lys Pro Pro Gly Ala Val Pro Ser
        515                 520                 525

Asn Ala Leu Thr Asn Pro Ala Pro Ser Lys Leu Pro Ile Asn Ser Thr
    530                 535                 540

Arg Ala Gly Met Val Pro Ser Lys Val Pro Thr Ser Met Val Leu Thr
545                 550                 555                 560

Lys Val Ser Ala Ser Thr Val Pro Thr Asp Gly Ser Ser Arg Asn Glu
                565                 570                 575

Glu Thr Pro Ala Ala Pro Thr Pro Ala Gly Ala Thr Gly Gly Ser Ser
            580                 585                 590

Ala Trp Leu Asp Ser Ser Ser Glu Asn Arg Gly Leu Gly Ser Glu Leu
        595                 600                 605

Ser Lys Pro Gly Val Leu Ala Ser Gln Val Asp Ser Pro Phe Ser Gly
    610                 615                 620

Cys Phe Glu Asp Leu Ala Ile Ser Ala Ser Thr Ser Leu Gly Met Gly
625                 630                 635                 640

Pro Cys His Gly Pro Glu Glu Asn Glu Tyr Lys Ser Glu Gly Thr Phe
                645                 650                 655

Gly Ile His Val Ala Glu Asn Pro Ser Ile Gln Leu Leu Glu Gly Asn
            660                 665                 670

Pro Gly Pro Pro Ala Asp Pro Asp Gly Gly Pro Arg Pro Gln Ala Asp
        675                 680                 685
```

```
Arg Lys Phe Gln Glu Arg Glu Val Pro Cys His Arg Pro Ser Pro Gly
    690                 695                 700

Ala Leu Trp Leu Gln Val Ala Val Thr Gly Val Leu Val Val Thr Leu
705                 710                 715                 720

Leu Val Val Leu Tyr Arg Arg Arg Leu His His Leu Tyr Phe Trp Asp
                725                 730                 735

Val Trp Tyr Ile Tyr His Phe Cys Lys Ala Lys Ile Lys Gly Tyr Gln
            740                 745                 750

Arg Leu Ile Ser Pro Asp Cys Cys Tyr Asp Ala Phe Ile Val Tyr Asp
        755                 760                 765

Thr Lys Asp Pro Ala Val Thr Glu Trp Val Leu Ala Glu Leu Val Ala
    770                 775                 780

Lys Leu Glu Asp Pro Arg Glu Lys His Phe Asn Leu Cys Leu Glu Glu
785                 790                 795                 800

Arg Asp Trp Leu Pro Gly Gln Pro Val Leu Glu Asn Leu Ser Gln Ser
                805                 810                 815

Ile Gln Leu Ser Lys Lys Thr Val Phe Val Met Thr Asp Lys Tyr Ala
            820                 825                 830

Lys Thr Glu Asn Phe Lys Ile Ala Phe Tyr Leu Ser His Gln Arg Leu
        835                 840                 845

Met Asp Glu Lys Val Asp Val Ile Ile Leu Ile Phe Leu Glu Lys Pro
    850                 855                 860

Phe Gln Lys Ser Lys Phe Leu Gln Leu Arg Lys Arg Leu Cys Gly Ser
865                 870                 875                 880

Ser Val Leu Glu Trp Pro Thr Asn Pro Gln Ala His Pro Tyr Phe Trp
                885                 890                 895

Gln Cys Leu Lys Asn Ala Leu Ala Thr Asp Asn His Val Ala Tyr Ser
            900                 905                 910

Gln Val Phe Lys Glu Thr Val His Ser Asp Glu His His His Asp Asp
        915                 920                 925

Ser Leu Pro His Pro Gln Gln Ala Thr Asp Asp Ser Gly His Glu Ser
    930                 935                 940

Asp Ser Asn Ser Asn Glu Gly Arg His His Leu Leu Val Ser Gly Ala
945                 950                 955                 960

Gly Asp Gly Pro Pro Leu Cys Ser Gln Asn Leu Gly Ala Pro Gly Gly
                965                 970                 975

Gly Pro Asp Asn Gly Pro Gln Asp Pro Asp Asn Thr Asp Asp Asn Gly
            980                 985                 990

Pro Gln Asp Pro Asp Asn Thr Asp  Asp Asn Gly Pro His  Asp Pro Leu
        995                 1000                1005

Pro Gln  Asp Pro Asp Asn Thr  Asp Asp Asn Gly Pro  Gln Asp Pro
    1010                1015                1020

Asp Asn  Thr Asp Asp Asn Gly  Pro His Asp Pro Leu  Pro His Ser
    1025                1030                1035

Pro Ser  Asp Ser Ala Gly Asn  Asp Gly Gly Pro Pro  Gln Leu Thr
    1040                1045                1050

Glu Glu  Val Glu Asn Lys Gly  Gly Asp Gln Gly Pro  Pro Leu Met
    1055                1060                1065

Thr Asp  Gly Gly Gly Gly His  Ser His Asp Ser Gly  His Gly Gly
    1070                1075                1080

Gly Asp  Pro His Leu Pro Thr  Leu Leu Leu Gly Ser  Ser Gly Ser
    1085                1090                1095

Gly Gly  Asp Asp Asp Asp Pro  His Gly Pro Val Gln  Leu Ser Tyr
```

-continued

| | | | |
|---|---|---|---|
| 1100 | 1105 | 1110 | |
| Tyr Asp | | | |
| 1115 | | | |